(12) United States Patent
Gosney et al.

(10) Patent No.: US 12,138,377 B2
(45) Date of Patent: Nov. 12, 2024

(54) APPARATUS FOR PROCESSING OF BLOOD TO NEUTRALIZE PATHOGEN CELLS THEREIN

(71) Applicants: William M. Gosney, Lucas, TX (US); Dale B. Nixon, Dallas, TX (US)

(72) Inventors: William M. Gosney, Lucas, TX (US); Dale B. Nixon, Dallas, TX (US)

( * ) Notice: Subject to any disclaimer, the term of this patent is extended or adjusted under 35 U.S.C. 154(b) by 0 days.

(21) Appl. No.: 17/814,536

(22) Filed: Jul. 25, 2022

(65) Prior Publication Data

US 2024/0024555 A1     Jan. 25, 2024

(51) Int. Cl.
*A61M 1/36* (2006.01)

(52) U.S. Cl.
CPC ..... *A61M 1/3681* (2013.01); *A61M 2205/053* (2013.01)

(58) Field of Classification Search
CPC .............. A61M 1/3681; A61M 2205/053
USPC ........................................ 604/6.08
See application file for complete search history.

(56) References Cited

U.S. PATENT DOCUMENTS

| | | | |
|---|---|---|---|
| 4,786,812 A | 11/1988 | Humphreys | |
| 5,035,693 A | 7/1991 | Kratzer et al. | |
| 6,127,507 A | 10/2000 | Santerre | |
| 6,584,217 B1 * | 6/2003 | Lawless | G01N 21/8483 382/133 |
| 6,746,613 B2 | 6/2004 | Korenev | |
| 6,872,198 B1 | 3/2005 | Wilson et al. | |
| 6,998,076 B2 | 2/2006 | Ohshiro | |
| 7,112,916 B2 | 9/2006 | Goh et al. | |
| 7,229,427 B2 * | 6/2007 | Mallett | A61M 1/3683 604/4.01 |
| 7,346,205 B2 | 3/2008 | Walker, Jr. | |
| 7,669,980 B2 | 3/2010 | Silverbrook | |
| 7,758,208 B2 | 7/2010 | Bailey | |
| 7,837,897 B2 | 11/2010 | Zhang et al. | |
| 7,889,154 B2 | 2/2011 | Araki et al. | |
| 8,242,832 B2 | 8/2012 | Ochi et al. | |
| 8,258,899 B2 | 9/2012 | Feng et al. | |
| 8,496,606 B2 * | 7/2013 | Leonard | A61P 13/12 604/4.01 |
| 8,624,968 B1 | 1/2014 | Hersee et al. | |
| 9,141,885 B2 | 9/2015 | Yang et al. | |

(Continued)

FOREIGN PATENT DOCUMENTS

| | | |
|---|---|---|
| DE | 102018003533 A1 | 10/2019 |
| KR | 101485336 B1 | 1/2015 |

*Primary Examiner* — Andrew J Mensh

(57) ABSTRACT

An operational unit for locating and neutralizing pathogen cells in blood includes a cassette which has a plurality of thin holding chambers that are filled with blood drawn from a patient. A light source illuminates the holding chambers and passes light to an underlying sensor array such that the cells in the blood selectively block the light to produce shadow images of the cells. A processor performs pattern recognition to locate the pathogen cells by use of an image library. After the pathogen cells are located, a source of ultraviolet light is activated and UV light is passed through selectively controlled shutters to illuminate only the limited areas that have the identified pathogen cells. Sufficient ultraviolet light energy is applied to destroy the identified cells. A pump refills the cassette holding chambers, returns the neutralized-pathogen blood to the patient, and the process is repeated.

20 Claims, 39 Drawing Sheets

(56) References Cited

U.S. PATENT DOCUMENTS

| | | |
|---|---|---|
| 9,387,286 B2 | 7/2016 | Kelly et al. |
| 9,420,209 B2 | 8/2016 | Ahn et al. |
| 9,574,989 B2 | 2/2017 | Lei |
| 9,643,184 B2 | 5/2017 | Zeng et al. |
| 10,300,188 B2 | 5/2019 | Joos et al. |
| 10,641,698 B2* | 5/2020 | Shi .................... B01L 3/502738 |
| 11,253,858 B2 | 2/2022 | Sherman et al. |
| 2002/0076744 A1* | 6/2002 | Koller .................. C12N 5/0087 435/40.5 |
| 2003/0153825 A1* | 8/2003 | Mooradian .......... A61B 5/0059 600/407 |
| 2004/0022669 A1 | 2/2004 | Ruan et al. |
| 2005/0063872 A1 | 3/2005 | Foster |
| 2006/0058167 A1 | 3/2006 | Ragusa et al. |
| 2008/0099406 A1 | 5/2008 | Ruan et al. |
| 2011/0021966 A1* | 1/2011 | Leonard ................ A61M 37/00 210/748.14 |
| 2012/0223217 A1 | 9/2012 | Zheng et al. |
| 2013/0178834 A1 | 7/2013 | Greenberg et al. |
| 2015/0083596 A1 | 3/2015 | Hester |
| 2015/0293012 A1 | 10/2015 | Rapaport et al. |
| 2016/0041094 A1* | 2/2016 | Lei ..................... G01N 15/1433 250/573 |
| 2016/0058937 A1 | 3/2016 | Gaitas et al. |
| 2016/0171686 A1* | 6/2016 | Du ........................ G06T 7/0012 382/130 |
| 2017/0021042 A1 | 1/2017 | Dodd et al. |
| 2017/0049889 A1 | 2/2017 | Felder et al. |
| 2018/0078641 A1 | 3/2018 | Felder et al. |
| 2019/0099543 A1 | 4/2019 | Sasaki |
| 2020/0179929 A1* | 6/2020 | Sherman ............ G01N 33/4833 |
| 2020/0200729 A1 | 6/2020 | Sherman et al. |
| 2020/0232983 A1 | 7/2020 | Miller et al. |
| 2020/0256889 A1 | 8/2020 | Fine |
| 2020/0289819 A1 | 9/2020 | Srimathveeravalli et al. |
| 2020/0305783 A1* | 10/2020 | Baker ................ A61B 5/02007 |
| 2021/0333211 A1* | 10/2021 | Chen .................. G01N 21/6458 |
| 2021/0364511 A1* | 11/2021 | Yu ..................... B01L 3/502761 |
| 2021/0398296 A1 | 12/2021 | Fang et al. |
| 2022/0012456 A1* | 1/2022 | Knowles .............. G02B 21/008 |

* cited by examiner

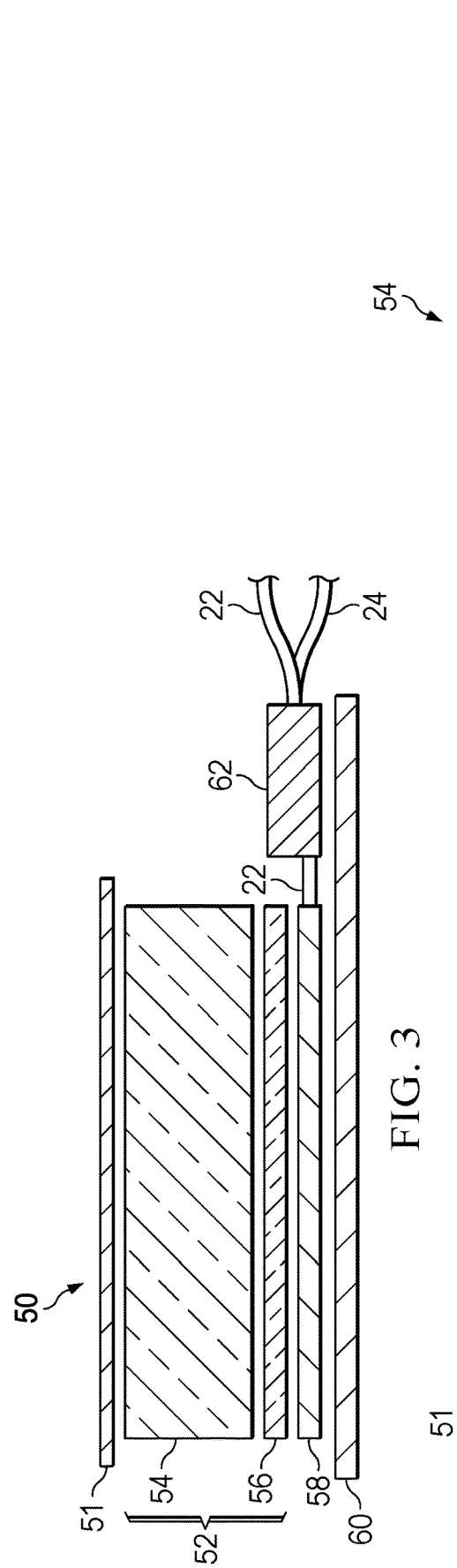
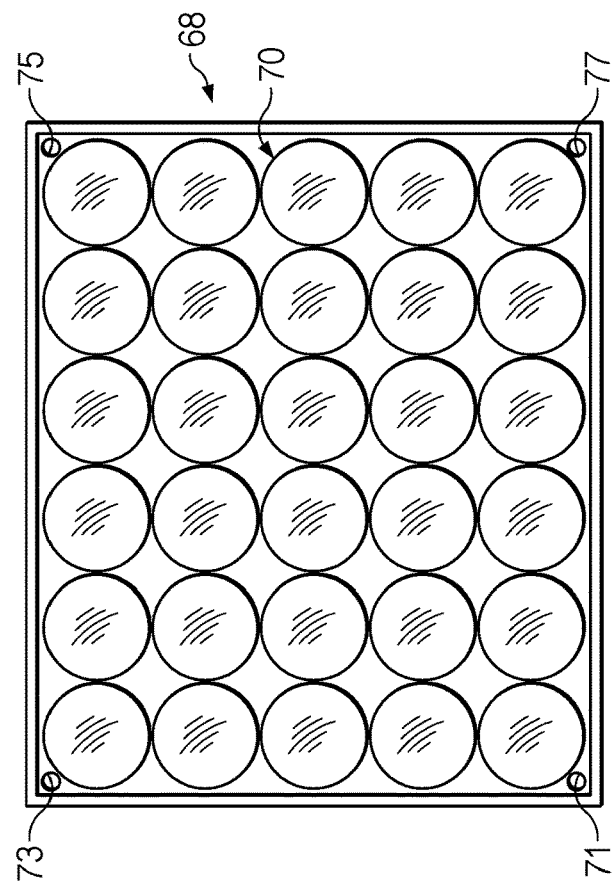
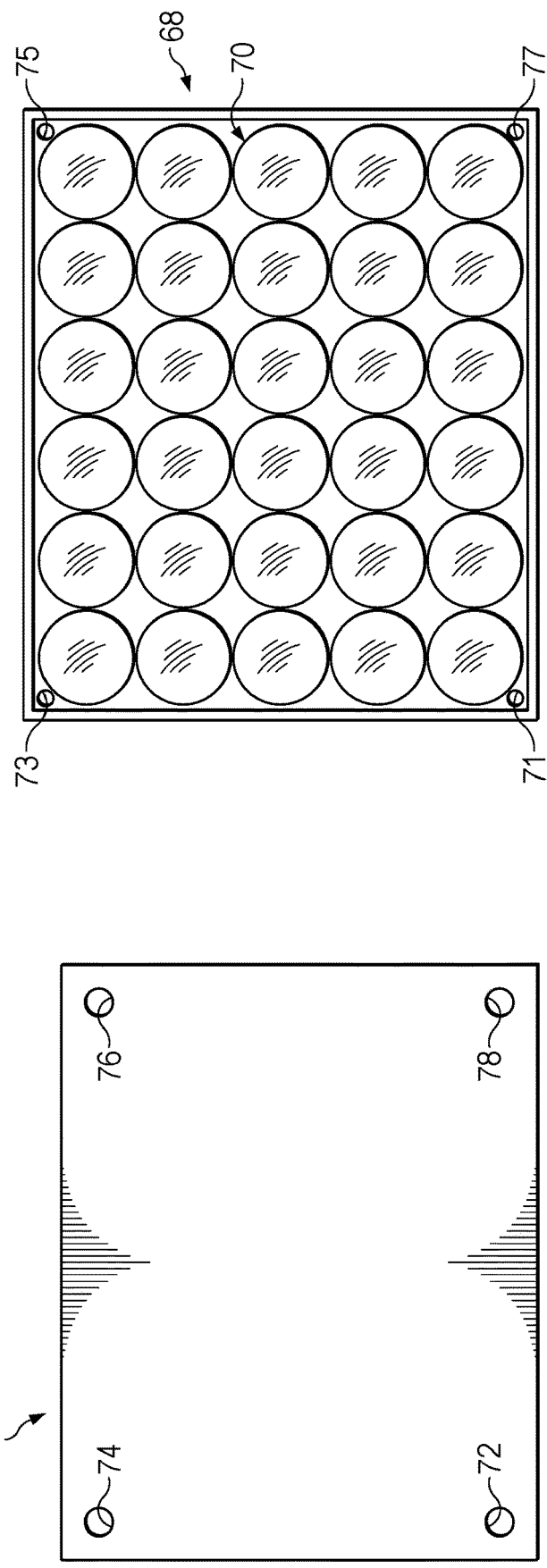
FIG. 3
FIG. 5
FIG. 4

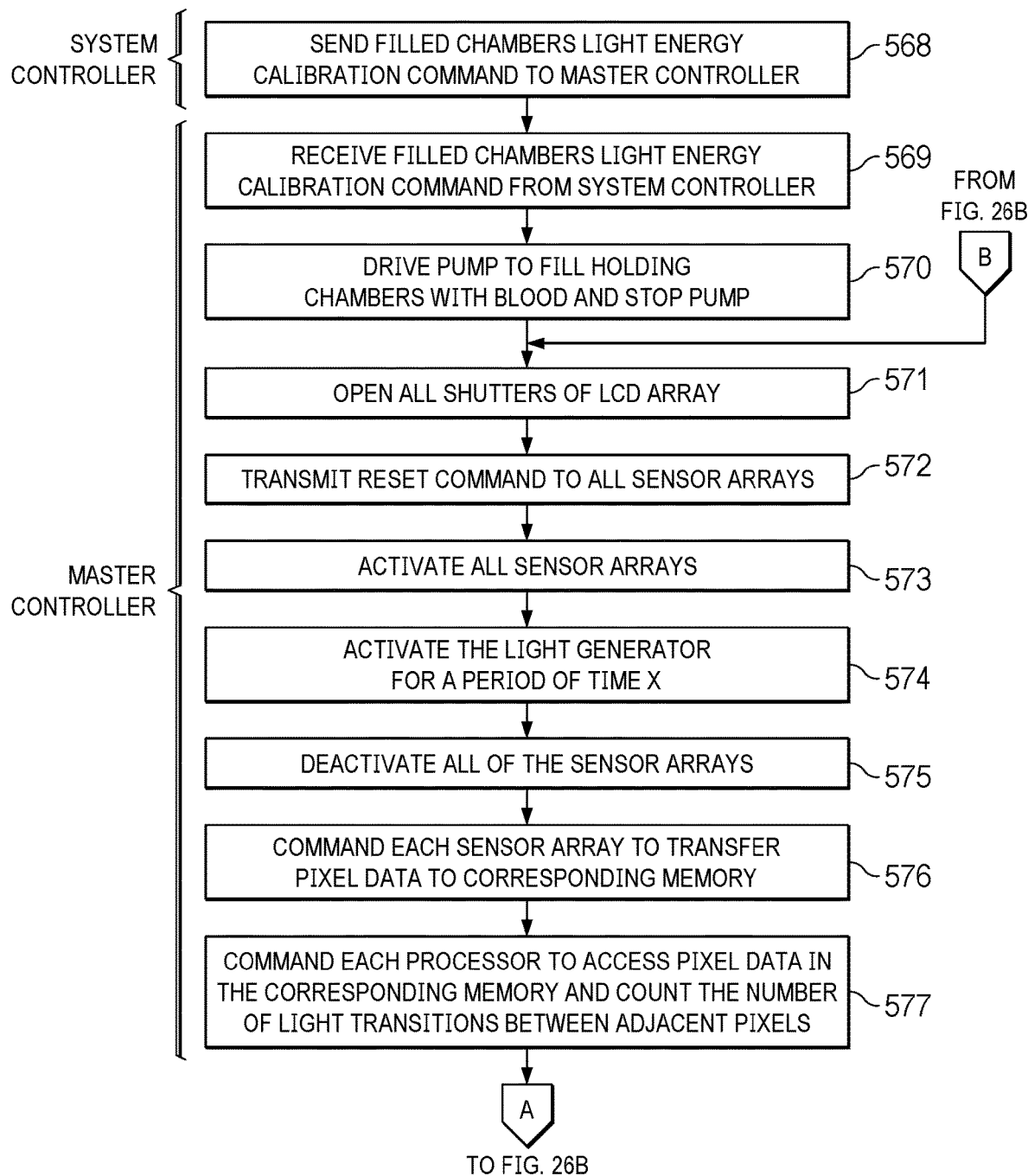

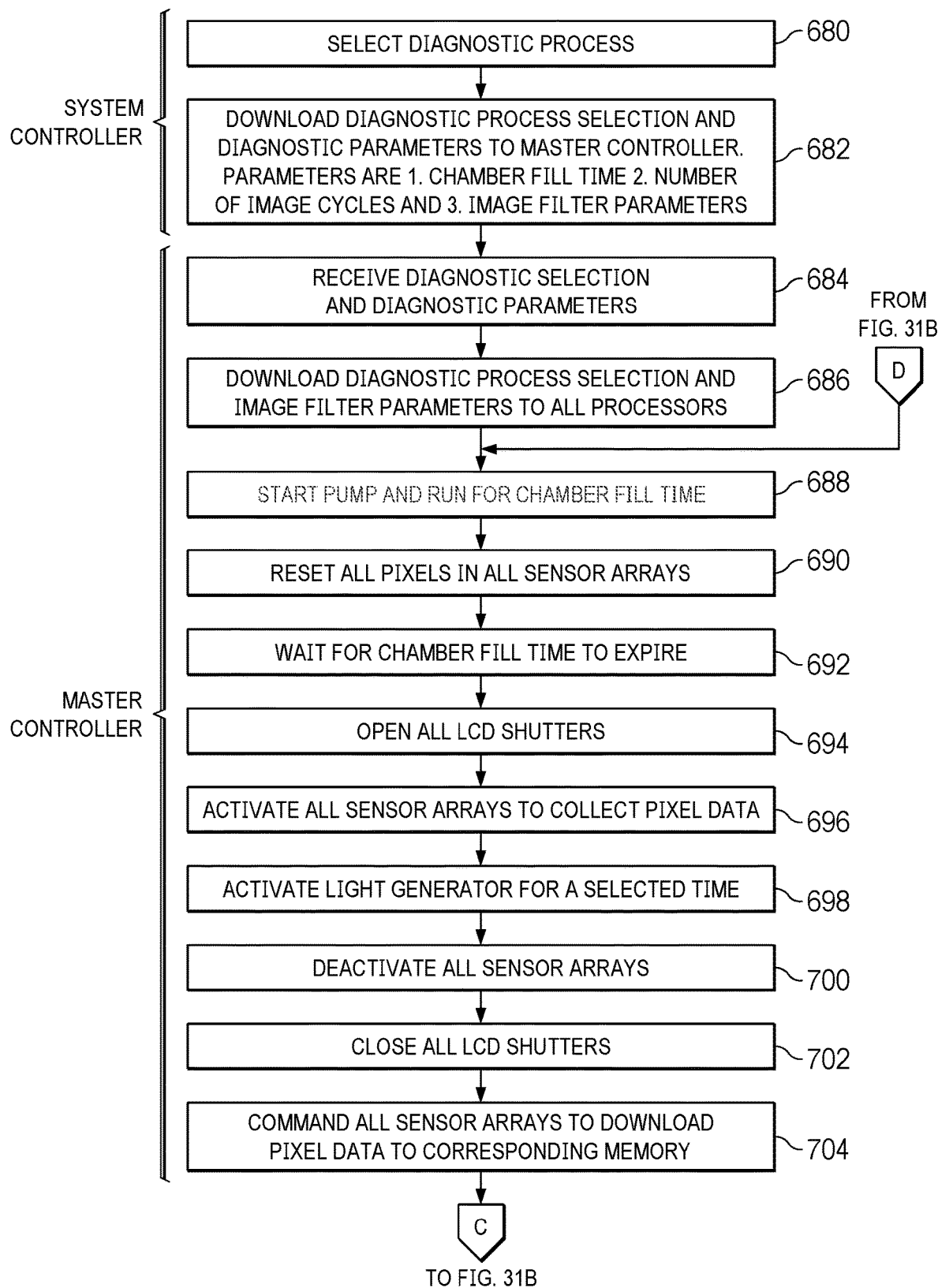

DIAGNOSTIC COLLECTED IMAGES
(MICRONS)

DIAGNOSTIC IMAGES SCREEN DISPLAY 1.  221,576

2.  154,097

3.  125,491

4.  96,055

5.  1,521

6.  647

7.  322

8.  54

9.  12

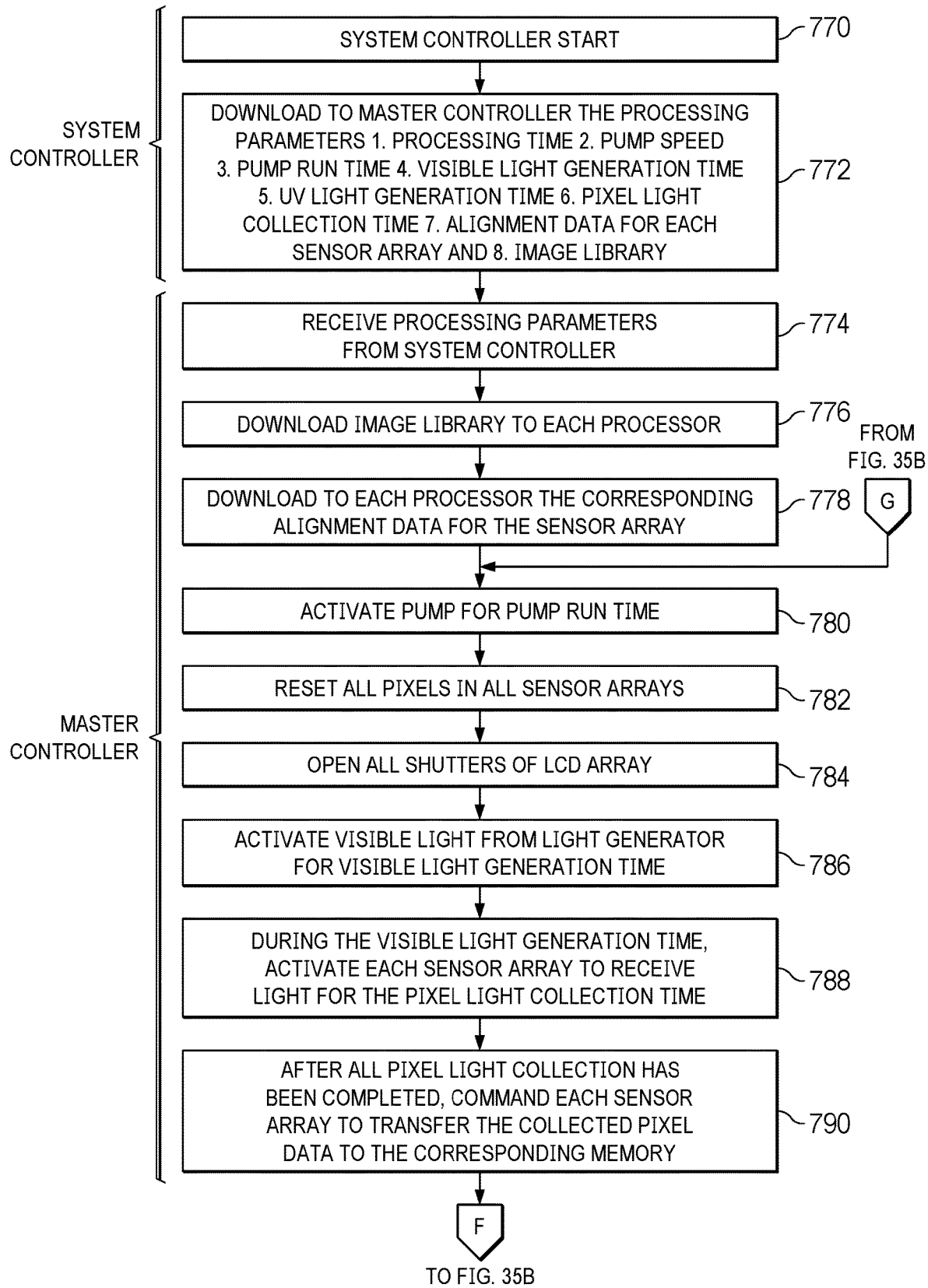

APPARATUS FOR PROCESSING OF BLOOD TO NEUTRALIZE PATHOGEN CELLS THEREIN

CROSS REFERENCE TO RELATED APPLICATIONS

Applicants have filed additional applications related to the subject matter of the present application. These applications are: Ser. No. 17/814,537 filed Jul. 25, 2022; Ser. No. 17/814,538 filed Jul. 25, 2022; Ser. No. 17/814,539 filed Jul. 25, 2022; Ser. No. 17/814,541 filed Jul. 25, 2022; Ser. No. 17/814,542 filed Jul. 25, 2022; Ser. No. 17/814,543 filed Jul. 25, 2022; Ser. No. 17/814,545 filed Jul. 25, 2022; Ser. No. 17/814,546 filed Jul. 25, 2022; Ser. No. 17/814,547 filed Jul. 25, 2022; Ser. No. 17/814,548 filed Jul. 25, 2022, and Ser. No. 17/814,549 filed Jul. 25, 2022.

BACKGROUND

1. Field of the Invention

The present invention is in the field of biotechnology and further the medical field of treating individuals who have an infection of pathogen cells in the bloodstream.

2. Description of the Related Art

The presence of bacteria in human blood is a serious condition termed "bacteremia". This condition can cause an infection that spreads through the bloodstream. This can also be termed "septicemia" which is defined as the invasion and persistence of pathogenic bacteria in the bloodstream. Such an infection can lead to a condition termed "sepsis" which is the body's reaction to the infection. Sepsis is a serious condition that can cause intense sickness including shock, and in some cases, can lead to the death of the infected person. A common pathogenic bacterium causing such infection is *E. coli*, but infections can also be caused by other pathogenic bacteria and other types of pathogenic cells such as the fungus *Candida auris*. The usual treatment for the patient is the application of antibiotics to try to kill the pathogenic bacteria in the bloodstream. However, this treatment is not successful for many patients with a bloodstream bacterial infection.

BRIEF DESCRIPTION OF THE DRAWINGS

For a more complete understanding of the present invention and the advantages thereof, reference is now made to the following description taken in conjunction with the accompanying drawings in which:

FIG. 3 is an elevation, section view of components inside the operational unit shown in FIG. 1, FIG. 4 is a plan view of the compression plate 51 shown in FIG. 3, FIG. 5 is a bottom view of the light source shown in FIG. 3 with an array of light generators.

FIGS. 26A and 26B illustrate a logic process for producing a calibration table for alignment correction between the LCD array and a light sensor pixel array.

SUMMARY OF THE INVENTION

The present invention comprises an apparatus for initially examining blood by imaging a first quantity of blood to identify and locate pathogen cells in the blood. The pathogen cells thus identified and located are then neutralized by the application of ultraviolet light energy to the specific locations for the identified and located pathogen cells. The first quantity of blood is then replaced with multiple subsequent quantities of blood and the process of identifying, locating and neutralizing pathogen cells is repeated for each quantity of blood. After such processing is performed for a period of time, the count of viable pathogen cells in the blood is decreased.

DETAILED DESCRIPTION OF THE INVENTION

The present invention is an apparatus for identifying pathogen cells in blood and neutralizing the identified cells to substantially reduce the count of such cells in the blood and thereby potentially reducing the harmful effect of the pathogen cells.

Figure 1:
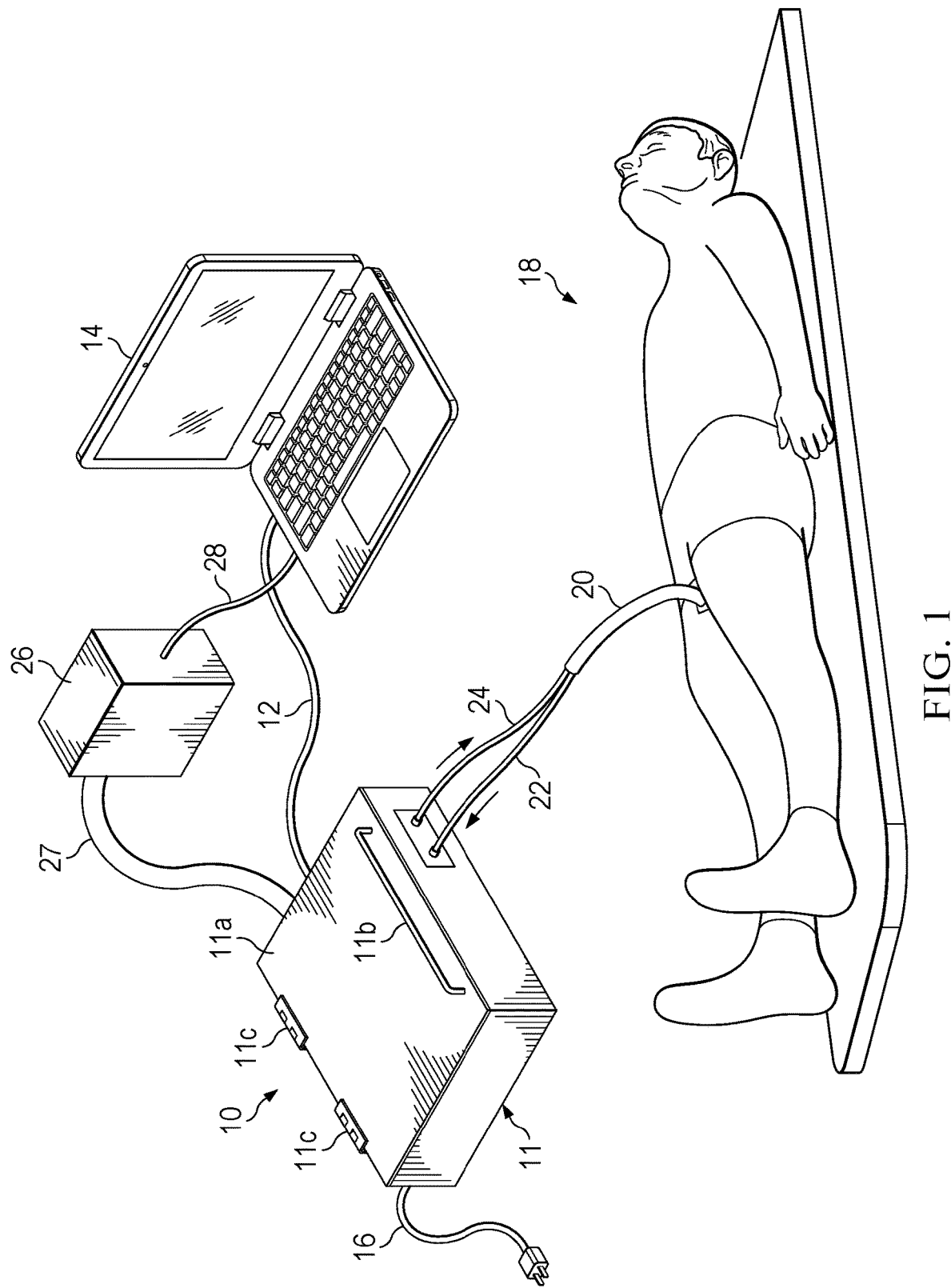
FIG. 1 is a perspective view of an overall system which includes an operational unit and a control unit.

Referring now to FIG. 1, there is shown a system for processing blood which identifies and determines locations of individual pathogen cells in blood and then applies energy to the specific location of each located pathogen cell of sufficient magnitude to kill that particular pathogen cell. The applied energy is limited to a restricted region surrounding the identified pathogen cell such that nearby blood cells, such as erythrocytes (red blood cells), leukocytes (white blood cells) and platelets are subjected to little or no exposure.

The principal operations performed with the blood are carried out in an operational unit 10 which is connected by a data and control cable 12 to a system controller 14 which can be, for example, a laptop computer, or a work station. The operational unit 10 receives electrical power via a power line 16.

The operational unit 10 is connected to a patient 18 by means of a two-lumen (two fluid channels) catheter 20. In this example, the catheter 20 is inserted into an artery in the leg of patient 18 to both receive blood from the patient and return blood to the patient. The catheter 20 has one lumen thereof connected to a blood input line 22 which is connected to operational unit 10 and has a second lumen connected to a blood return line 24 which is also connected to the operational unit 10. The blood of patient 18 flows into the catheter 20, through input line 22 to the operational unit 10 and from the operational unit 10 through the return line 24 and catheter 20 back to the patient 18. A catheter, such as 20, is described in U.S. Pat. No. 6,872,198 issued Mar. 25, 2005 which patent is incorporated herein by reference in its entirety.

Within the operational unit 10 the blood is imaged to identify and locate pathogenic cells in the blood followed by neutralizing the located pathogenic cells. This process continues over a period of time with a flow of blood from the patient with the goal of reducing the number of viable pathogenic cells in the patient's blood.

The operational unit 10 includes an enclosure 11, a top lid 11a which can be opened by use of a handle 11b which rotates the lid on hinges 11c. A thermal control unit 26, for example a heat pump, supplies heated or cooled air at a selected temperature through a duct 27 to the interior of the enclosure 11. The thermal control unit 26 is operated by the system controller 14 via a cable 28. The system controller 14 monitors temperature inside the enclosure 11 and controls the thermal control unit 26 to supply air to drive the temperature in the enclosure 11 to a preselected temperature or temperature range. The enclosure 11 has an opening 46 for passage therethrough of flow tubes and electrical conductors.

An embodiment of the invention described in the following text and corresponding drawings utilizes ultraviolet light (UV) to neutralize located pathogen cells in blood. The UV light is of sufficient intensity to kill the pathogen cells located in the blood.

Figure 2:
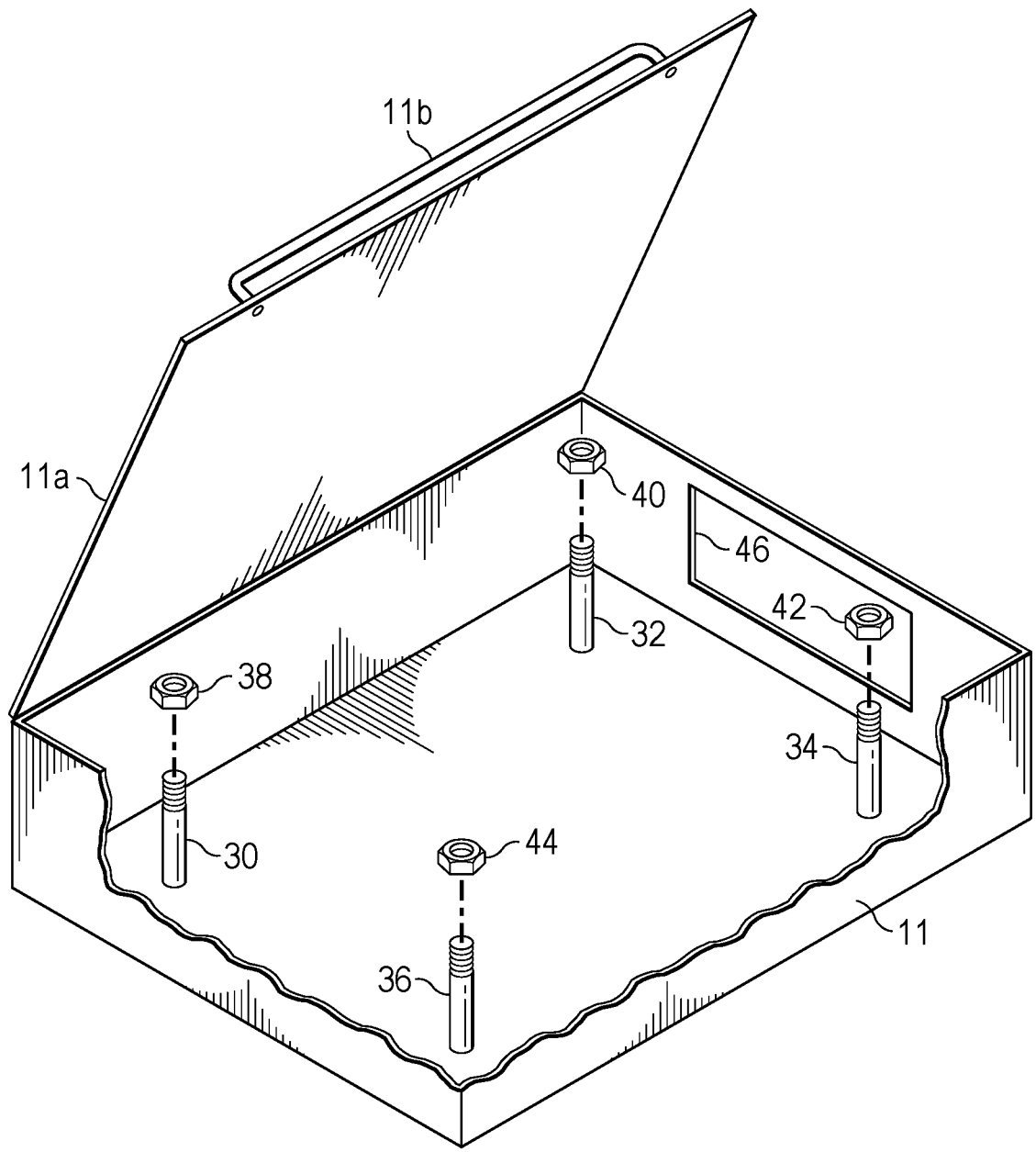
FIG. 2 is a perspective view showing the interior of the enclosure 11 shown in FIG. 1.

The interior of the enclosure 11, shown in FIG. 1, is illustrated in FIG. 2. A set of four rods 30, 32, 34 and 36 are mounted on the interior bottom surface of the enclosure 11. These rods project upward, perpendicular to the bottom surface of the enclosure 11. The top end of each of the rods 30, 32, 34 and 36 are threaded to receive respective nuts 38, 40, 42 and 44. The nuts 38, 40, 42 and 44, when mounted on the corresponding rods, engage the top surface of a compression plate 51 shown in FIGS. 3 and 4.

A UV light system of the present invention is shown in FIG. 1, and described in the corresponding text, with specific internal components 50 of the operational unit 10 as shown in FIG. 3. The operational unit 10 has multiple components 50 inside the enclosure 11. These components include the compression plate 51, an illumination unit 52 comprising a light source 54 and an LCD shutter array 56. The unit 50 further includes a cassette 58 and an imager and processor unit 60. Components 50 further include a peristaltic pump 62 connected by line 22 to a cassette 58. The peristaltic pump is connected to line 22. Pump 62 draws blood from patient 18 through input line 22 into the operational unit 10 and the blood leaves unit 10 through return line 24 and through catheter 20 to patient 18. The components 52, 58 and 60 have planar configurations and, in operation, are pressed together with little spacing between them and secured to limit relative movement. The pump 62 supplies blood to the cassette 58 through input line 22. The return line 24 does not pass through the pump 62. The pump 62 can alternatively be positioned on the exterior of the enclosure 11.

The compression plate 51 is shown in FIG. 4. Plate 51 includes holes 72, 74, 76 and 78 which are positioned to receive the respective rods 30, 32, 34 and 36, see FIG. 2. All of the elements 51, 54, 56, 58 and 60 are provided with corner holes for receiving the rods 30, 32, 34 and 36. When the nuts 38, 40, 42 and 44 are affixed to the rods 30, 32, 34 and 36, with all of the noted components 50 (see FIG. 3) in place and having the rods 30, 32, 34 and 36 passing therethrough, the nuts are tightened on the rods to cause the compression plate 51 to apply force to the stacked elements 51, 54, 56, 58 and 60 to clamp them together and restrain relative movement, either horizontally or vertically, between these elements.

A planar, bottom view of the light source 54 is shown in FIG. 5. Source 54 includes a 5×6 array 68 of light generators, which includes a light generator 70 which is representative of all of the light generators in the array 68. Each of the light generators, including 70, produces a collimated beam of light directed perpendicular to the planar LCD shutter array 56. The light generator 70 is further shown in an elevation view in FIG. 6. Light source 54 includes holes 71, 73, 75 and 77 for receiving the rods 30, 32, 34 and 36. The light source 54 produces collimated light over an area. The area of light is directed perpendicular and through LCD array 56, the cassette 58 and to the sensor arrays in unit 60.

Collimated light sources are well known in the art. Multiple embodiments of collimated light source generators are usable with the present invention. A collimated light generator is described in U.S. Pat. No. 7,758,208 issued Jul. 20, 2010 which patent is incorporated herein by reference in its entirety.

Figure 6:
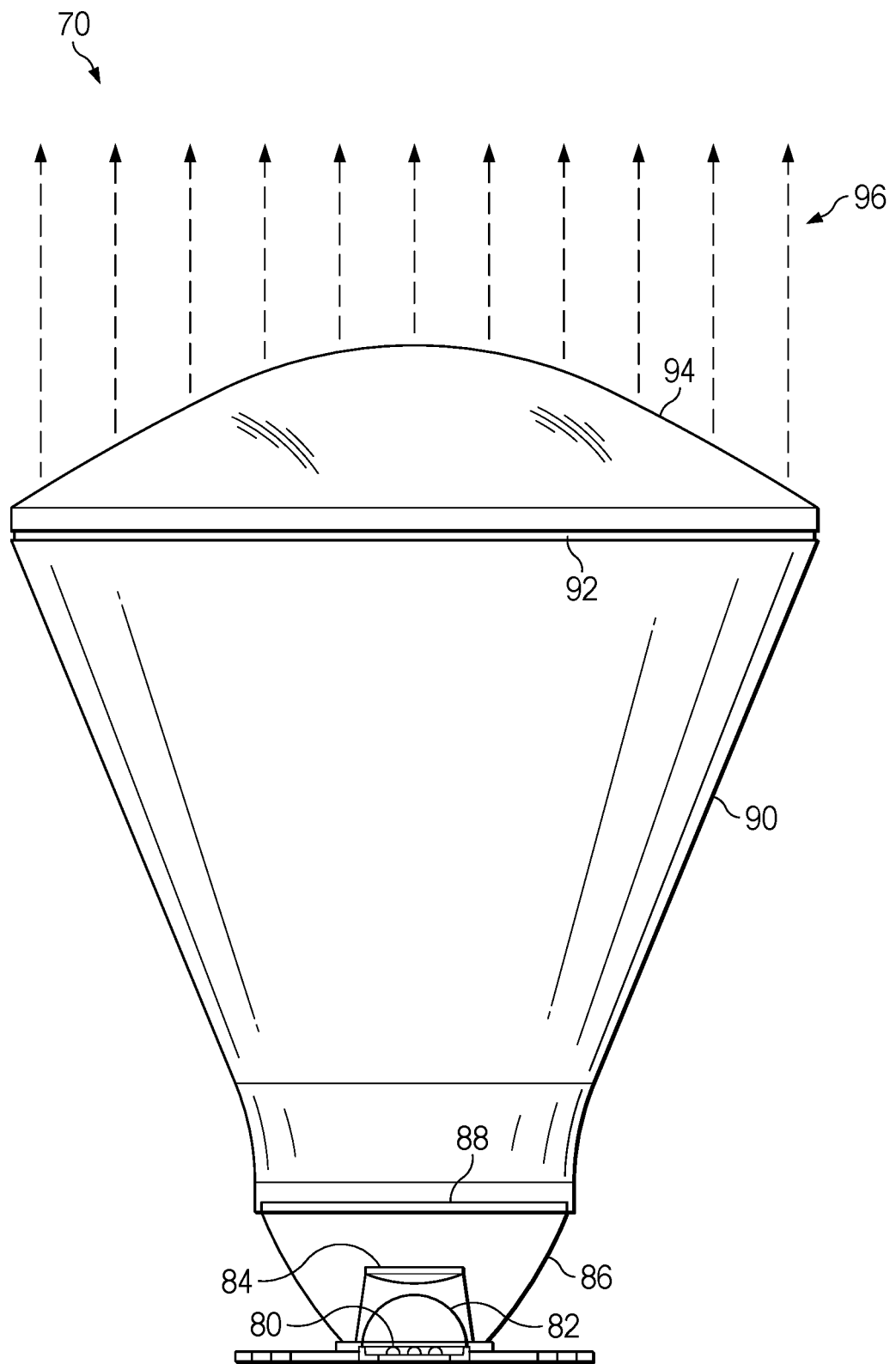
FIG. 6 is an elevation, sectional view of a collimated beam light generator, as shown in FIG. 5.
Figure 7:
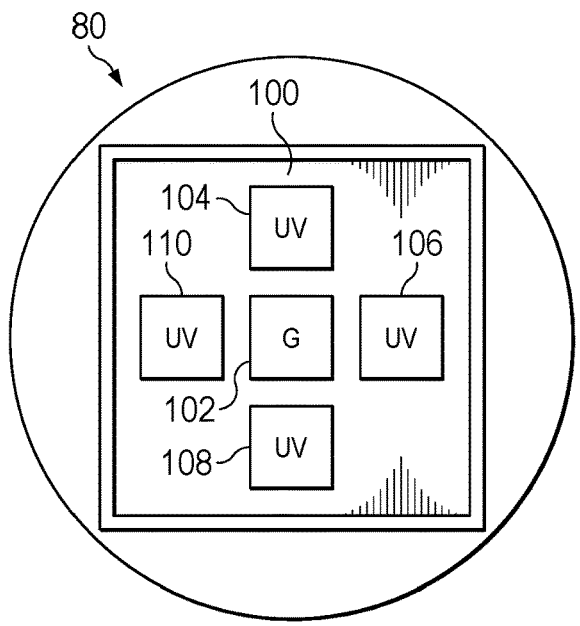
FIG. 7 is a top view of the light engine shown in FIG. 6 with visible and UV LED light sources.

Referring to FIG. 6, the light generator 70 includes a light engine 80, further shown in FIG. 7, an extraction lens 82, a collimator lens 84, a collimator lens 86, a lenslet array 88, a profile reflector 90, a secondary lenslet array 92 and a secondary collimator lens 94. The light generator 70 produces a collimated beam of light 96.

The light engine 80 is shown in a top view in FIG. 7. The engine 80 has a supporting planar base 100. A green light LED 102 and UV LEDs 104, 106, 108 and 110 are mounted on the base 100. The green LED 102 and the four UV LEDs 104, 106, 108 and 110 can be driven separately to produce a collimated green light or collimated UV light, see beam 96 in FIG. 4. As example values, the green light can have a wavelength of 520 nanometers and the UV light a wavelength of 250-265 nanometers.

Figure 8:
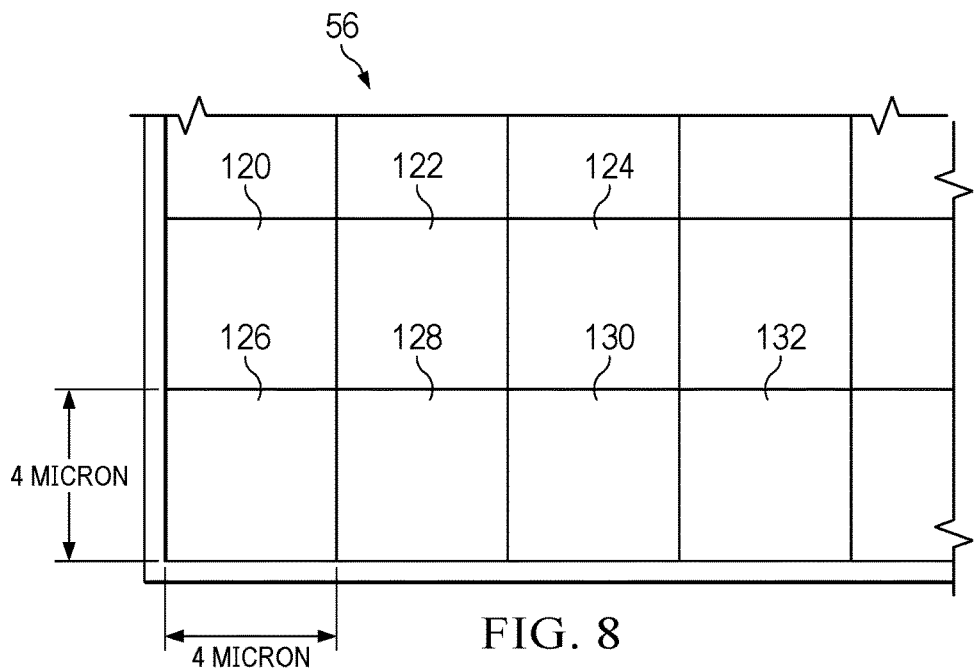
FIG. 8 is a top view of a segment of the LCD array shown in FIG. 3.

The LCD shutter array 56, shown in FIG. 3, is illustrated is greater detail in FIG. 8. This top view shows a lower left corner of the entire array 56. The displayed section includes individual LCD shutters 120, 122, 124, 126, 128, 130 and 132. Each of the shutters in array 56 can be individually operated to either allow light, such as from the collimated light beam 96 (FIG. 6) to pass through or be blocked, depending on an applied electric field. LCD shutter arrays are well known technology, such as used in LCD television screens. Specific structures and driving electronics for LCD shutters are shown in U.S. Pat. No. 7,837,897 issued Nov. 23, 2010 and U.S. Pat. No. 7,889,154 issued Feb. 15, 2011 each of which is incorporated herein by reference in its entirety.

Further referring to the LCD array 56 in FIG. 8, for one embodiment of the invention, each LCD shutter, for example shutter 126, is square with dimensions of 4 microns by 4 microns. A section of the array 56 can have overall planar dimensions of, for example, 2 centimeters by 2 centimeters for one cassette chamber. Such an array therefore has $2.5 \times 10^7$ separate LCD shutters. Each shutter is individually controlled. When the array 56 is used with the light source 54 (FIGS. 3 and 5), the shutters can be closed and block all transmission of light from the light source 54, or the shutters can be selectively opened to allow a segment of the light beam 96, such as a 4 micron by 4 micron segment, to pass through the LCD array 56 to the cassette 58. Or, all of the shutters in array 56 can be opened and allow full exposure of the underlying cassette chambers to light from light source 54.

Figure 9:
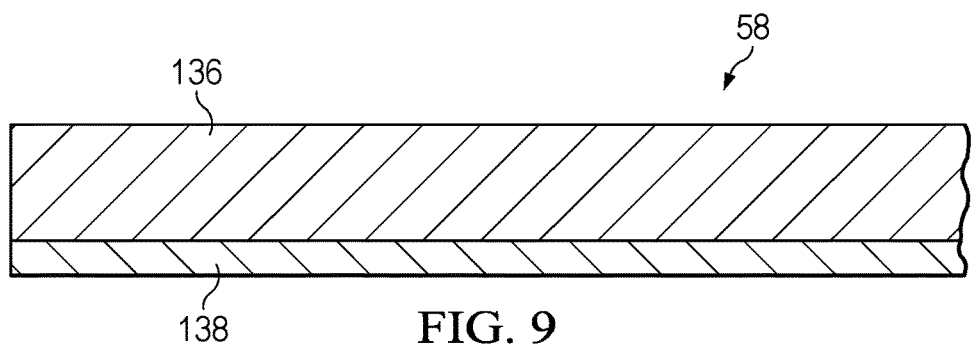
FIG. 9 is an elevation, section view of the cassette shown in FIG. 3.

The cassette 58 is shown in a section, elevation view in FIG. 9. Cassette 58 comprises a top layer 136 and a bottom layer 138. After fabrication as separate layers, the layers 136 and 138 are bonded together to form the cassette 58.

Figure 10:
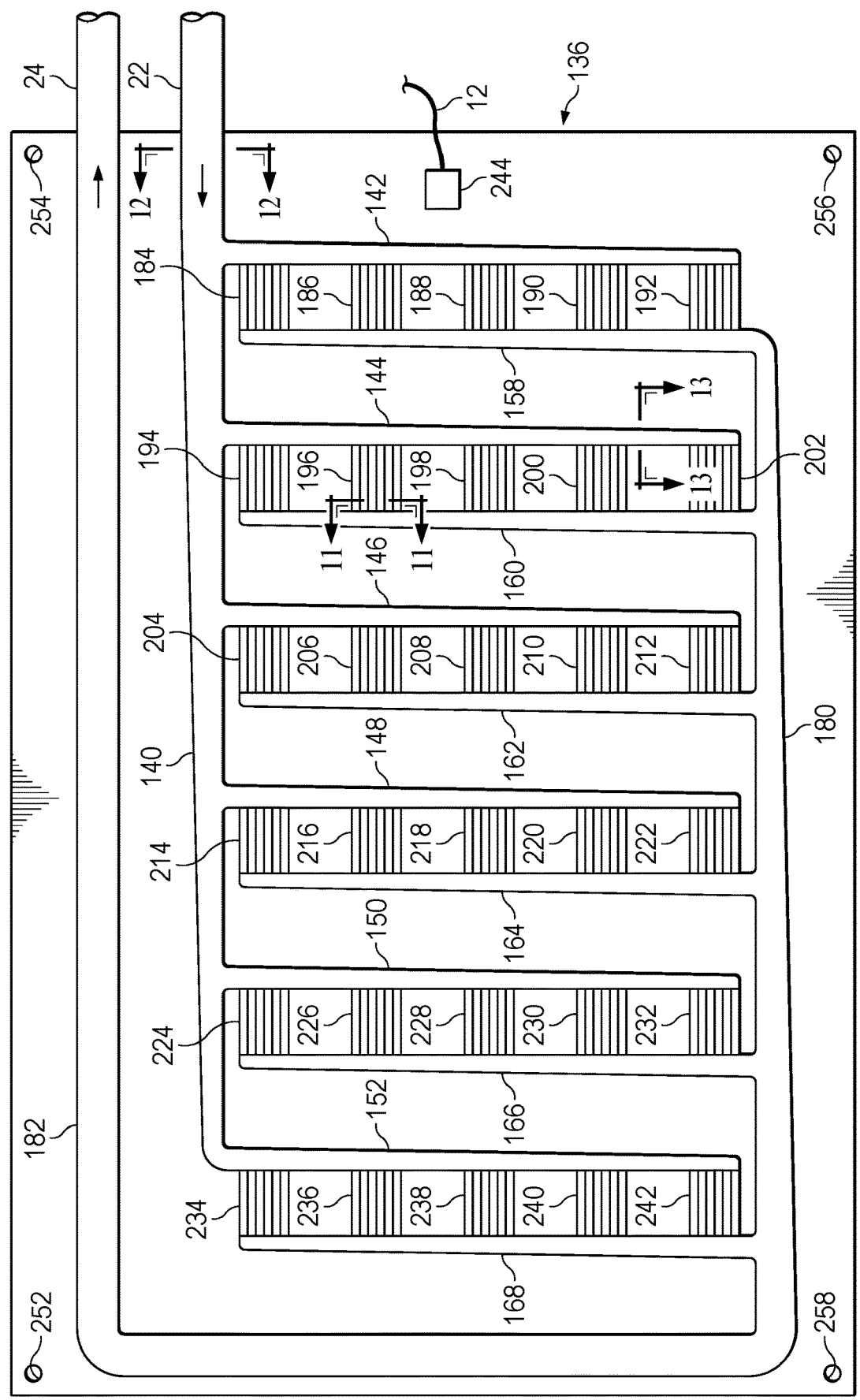
FIG. 10 is a top-down view through the top layer of the cassette shown in FIGS. 3 and 9, illustrating blood flow channels (manifolds) into and from multiple holding chambers of the cassette.

The cassette 58 (see FIGS. 3 and 9) is shown in a top-down view through layer 136 in FIG. 10. The peristaltic pump 62 drives blood through input line 22 into the cassette 58 and return blood from the cassette 58 is provided through return line 24. (See FIG. 1) The cassette 58 has a plurality of holding chambers for the blood. An input manifold distributes the blood to the holding chambers and a return manifold receives the blood from the holding chambers and routes it to the blood return line 24. The chambers and flow lines are molded into the bottom surface of layer 136. The cassette 58 receives blood from input line 22 to a distribution line 140 which supplies blood in parallel to chamber input lines 142, 144, 146, 148, 150 and 152. The blood is transferred from the chambers to chamber output lines 158, 160, 162, 164 and 168, which lines in turn route the blood in parallel to a collection line 180 that is connected to supply the received blood to a return line 182 that is connected to the blood return line 24.

The cassette 58, as shown in FIG. 10 for an embodiment of the invention, has 30 holding chambers 184, 186, 188, 190, 192, 194, 196, 198, 200, 202, 204, 206, 208, 210, 212, 214, 216, 218, 220, 222, 224, 226, 228, 230, 232, 234, 236, 238, 240 and 242. The cassette 58 input manifold comprises distribution line 140 and chamber input lines 142-152. The output manifold comprises chamber output lines 158-168, the collection line 180 and the return line 182. This manifold configuration provides approximately the same blood flow path distance from the input of line 140 to the output of line 182 for the blood flowing through each of the holding chambers. This configuration contributes to a more uniform flow of blood through the holding chambers and uniform pressure drop through the cassette. Further shown in FIG. 10 is a temperature sensor 244 mounted on the top surface of layer 136 and electrically coupled through cable 12 to the system controller 14, which monitors the temperature of the cassette 58 and drives the thermal control unit 26 to supply air to the interior of the enclosure 10 to regulate the temperature of the cassette 58 and therefore the blood in the cassette 58.

Input line 142 supplies blood to each of the chambers 184, 186, 188, 190, 192. Each chamber can have, for example, an X dimension of 2 centimeters, a Y dimension of 2 centimeters, and a thickness (Z dimension) of 8 microns. The facing surface of each chamber has an area 4 square centimeters. The facing surface is a wall of the chamber. Each chamber has a closing wall provided by the layer 138, see FIG. 9. Therefore, each chamber has parallel, opposing, transparent walls. The opposing walls are transparent to the UV and visible light produced by the light source 54. The opening width from the input line 142 into chamber 184 is the same as the Y dimension of the chamber, in this example, 2 centimeters. Likewise, the output from each chamber, such as 184, is the Y dimension, in this example, 2 centimeters. A chamber, as viewed at the input, is relatively wide (2 centimeters). The input to a chamber, such as 186, from an input line, such as 142, is an input port to the chamber. Likewise, the output from a chamber to the corresponding output line is an output port of the chamber. These input and output ports can have a length of, for example, 10-100 microns.

The blood leaves the holding chambers 186-242 and moves into the corresponding connected chamber output lines 158-168. The exit passageway from a chamber is the same configuration as the input passageway, that is, for this embodiment, the exit passageway is 2 centimeters wide and 8 microns thick. The blood flows through the output lines 158-168 into the collection line 180 and then into the return line 182.

As another flow example, further referring to FIG. 10, blood is driven into distribution line 140 and then into chamber input line 150 and at the far end of this line, into chamber 232. After the blood is processed, the pump 62 resumes operation and the blood in chamber 232 is driven out of the chamber into the chamber output line 166 and from the end of line 166 into the collection line 180. From line 180, the blood flows into the return line 182 and then into the blood return line 24. The blood travels through the cassette input manifold to all of the chambers and returns from all of the chambers through the cassette output manifold.

Further referring to FIG. 10, the cassette 58 is provided with alignment holes 252, 254, 256 and 258. The cassette 58 is lowered onto the upward facing rods 30, 32, 34 and 36 (See FIG. 2), mounted inside the operational unit 10, which pass through corresponding holes in the imager and processor unit (See FIG. 3). The rods pass through the holes in the cassette 58 to provide alignment of the cassette 58 with the imager and processor unit 60. The LCD array 56 and light source 54 (FIG. 3) have corresponding alignment holes to receive the rods 30, 32, 34 and 36 so that the imager and processor unit 60, cassette 58, LCD array 56 and light source 54 are aligned with each other. The top end of the rods is threaded so that nuts 38, 40, 42 and 44 (See FIG. 2) can be applied to each rod and tightened so that all four of these units are compressed together and held in alignment with each other.

Figure 11:
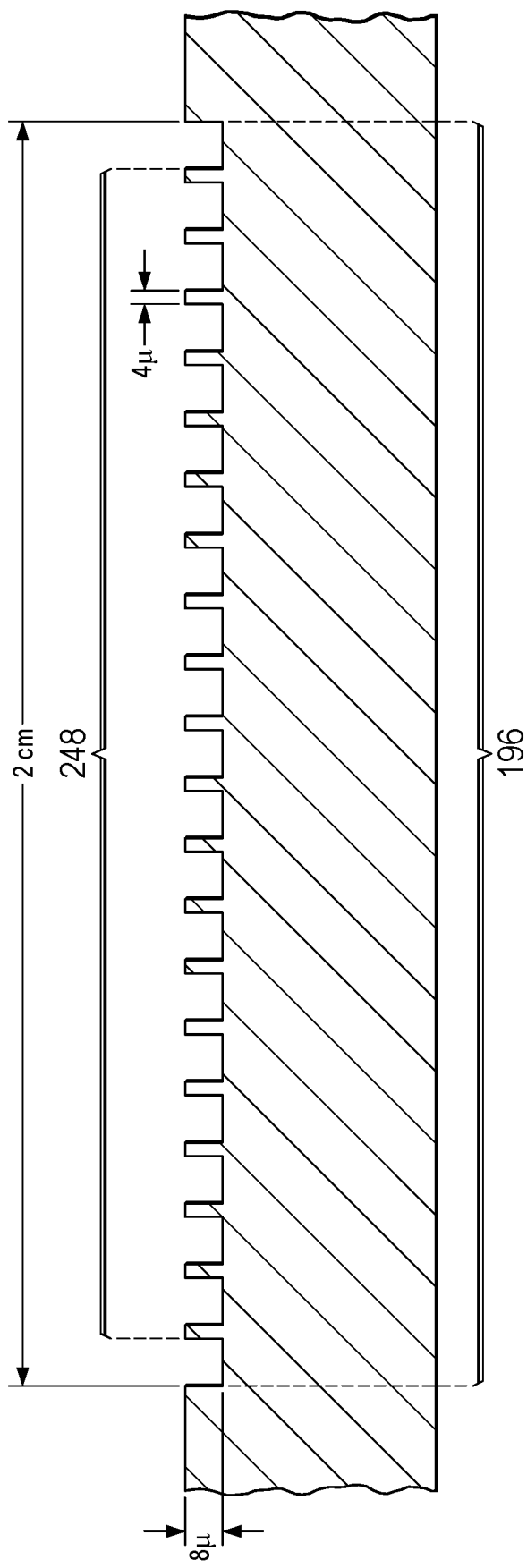
FIG. 11 is a section view of a holding chamber along lines 11-11 in FIG. 10.

FIG. 10 shows a top-down, planar view of the top layer 136 of cassette 58. Each of the holding chambers 184-242 comprises a recessed region into the bottom side of the top layer 136. Each chamber recess, in one embodiment, is approximately 8 microns thick, 2 centimeters long and 2 centimeters wide. Referring to FIG. 11, each holding chamber includes a plurality of long, thin ridges 248, illustrated as example horizontal lines in each chamber in FIG. 10, and shown in detail in FIG. 11, which is a section view along lines 11-11 of a representative holding chamber 196 in FIG. 10. Example dimensions for a holding chamber and the ridges 248 are shown in FIG. 11. The holding chamber 196 is approximately 2 centimeters wide, as shown, and 2 centimeters long. The ridges 248 extend for substantially the length (approximately 2 centimeters) of the holding chamber 196, less the length of the input and output ports for the chamber. Each ridge is preferably 8 microns high and 4 microns wide. In the described embodiment, each of the holding chambers 184-242, has a thickness of 8 microns. The chambers are preferably less than 10 microns thick, the spacing between the interior wall surfaces. In this example, there are 20 of the elongate ridges spaced in parallel across a distance of 2 centimeters. Therefore, the spacing between the ridges is approximately 950 microns. Each of the ridges 248 serves as a support for the bottom layer 138 (See FIG. 9) which is pressed against the top of the ridges 248. The ridges 248 also function as spacers to maintain an essentially uniform 8-micron thickness over all of the area of each holding chamber. The ridges 248, in this configuration, further form 21 flow channels through the chamber which reduce lateral flow of blood and supports a straight through flow from the input to the output of each chamber.

Figure 13:
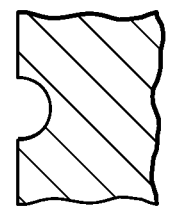
FIG. 13 is a section view of a flow channel along lines 13-13 in FIG.
Figure 12:
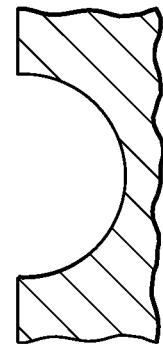
FIG. 12 is a section view of a flow channel along lines 12-12 in FIG.

FIG. 12 is a section view taken along lines 12-12 in FIG. 10 in the distribution line 140. The line 140 flow channel has a flat-bottom with a half-circle cross section that has been pressed or molded into the top layer 136. The flat, and sealing, surface of the flow line 140 is provided by the top surface of the bottom layer 138. FIG. 13 is a section view taken along lines 13-13 in FIG. 10 located in the input line 144. It is likewise pressed or molded into the top layer 136 and closed with the bottom layer 138. The cross-sectional area of line 144 at 13-13 is substantially smaller than that of line 140 at 12-12. There is a greater volume of blood flow through line 14 at 12-12 than through line 144 at 13-13. The cross-sectional area of a flow line is at least partially proportional to the volume of blood flow at that point.

Both of the layers 136 and 138 are fabricated of, for example, transparent polycarbonate plastic, produced by a pressing or molding process such as described in U.S. Pat. No. 6,998,076 issued Feb. 14, 2006 which patent is incorporated herein by reference in its entirety. As an example embodiment, the top layer 136 can be approximately 2-3 millimeters thick, bottom layer 138 can be 1-1.5 millimeters thick for a total cassette 58 thickness of approximately 3-4.5 millimeters. The cassette 58 can be fabricated of a plastic with an included anti-thrombogenic material to reduce the possible adhering of blood that contacts surfaces of the cassette 58. Such a material is described in U.S. Pat. No. 6,127,507 issued on Oct. 3, 2000, which patent is incorporated herein in its entirety. Alternatively, the anti-thrombogenic material can be applied as a surface coating on the plastic.

The top layer 136 of cassette 58 can be fabricated by the use of polycarbonate injection molding and a metal mold. An etched glass master is used to form the metal stamping mold. To make the glass master, the process starts with a sheet of glass. The sheet of glass, approximately 5 millimeters thick, is sequentially masked with photoresist patterns (as done in the manufacture of semiconductors) and an acid is applied to etch the non-masked portions. The acid removes a portion of the glass, producing a recessed pattern in the glass and forming the distribution lines and holding chambers. The final 8 micron etch can be done by plasma etching to produce more vertical sidewalls on the ridges 248. After removing the last photoresist, the surface of the glass mold is treated with a mold-release component, and then is covered with a layer of nickel or silver using an electrodeless plating method. Sputtering can be used, or a colloidal silver method can be used. Then, nickel is electroplated over the surface to a thickness of perhaps 0.5 cm forming a metal mold. After separating the electroformed nickel mold from the glass master, the metal mold has raised areas corresponding to the distribution lines and holding chambers. This process is similar to the manufacturing process for phonograph records, compact discs and DVDs as shown in U.S. Pat. No. 6,998,076 noted above. Heated polycarbonate injection molding is used with the metal mold to form the recessed flow channels and holding chambers in what will be the top layer of the cassette. The polycarbonate flows around the raised areas in the metal mold. When the metal mold and polycarbonate are cooled, the polycarbonate sheet is removed and it has the configuration for the top layer 136, as shown in FIGS. 10-13.

Alternately, a metal mold can be machined or etched to have the configuration to produce the cassette top layer by applying a sheet of polycarbonate to the mold, heating both the mold and the sheet and allowing the polycarbonate to flow into the metal mold to produce the desired shape for the cassette 58.

Figure 14:
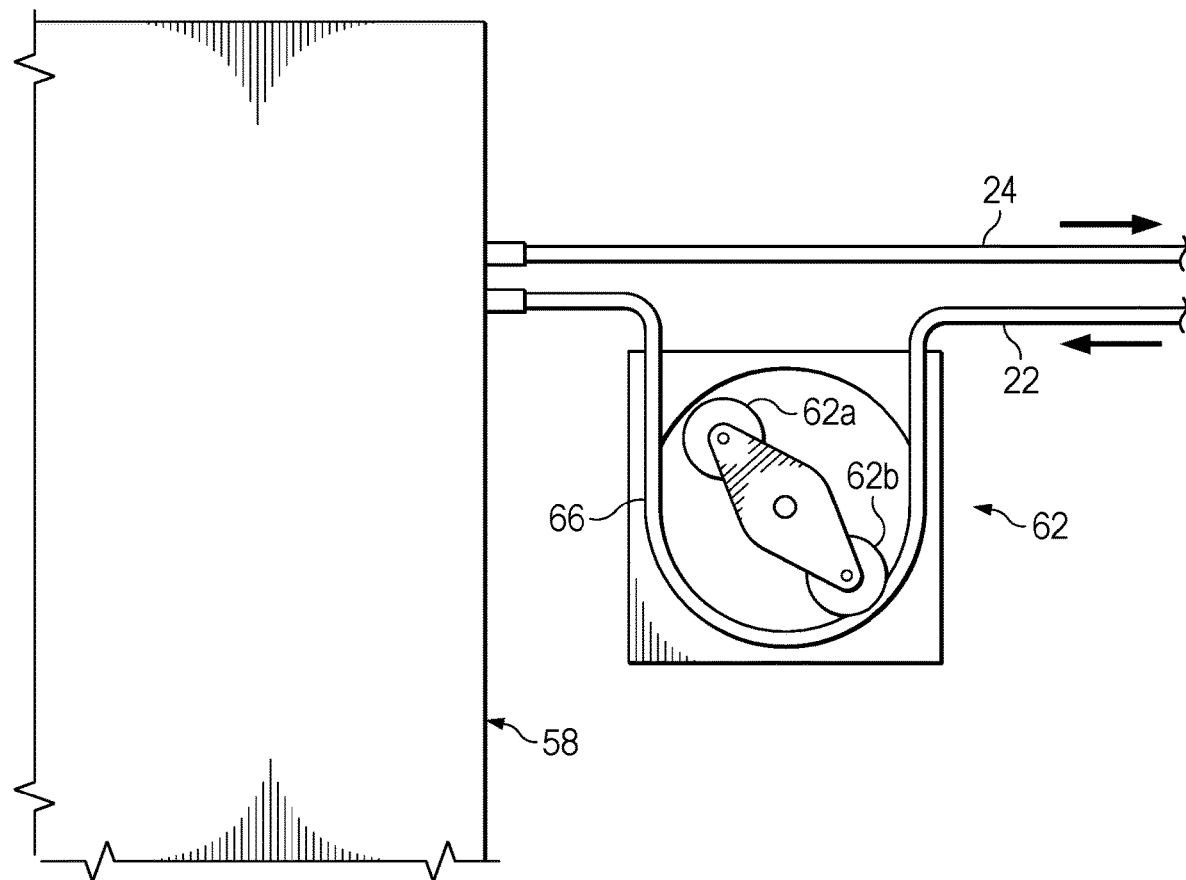
FIG. 14 is a top view of a peristaltic pump and a portion of the cassette shown in FIG. 3.

FIG. 14 is an illustration of the cassette 58 and peristaltic pump 62 together with the blood flow lines. The blood input line 22 is positioned in the pump 62 between pump rollers 62a and 62b and a circular pump pressure surface 66. The rollers rotate about a center shaft and compress the flexible line 22 against the surface 66. The rollers apply sufficient force to close the line 22 and, as they rotate, they force the blood to flow through the line 22 toward the cassette 58. The pump can be stopped and started as needed to pump blood to the cassette 58. After the blood has passed through the cassette 58, it flows through the return line 24 to the catheter 20 and then back to the patient 18. The structure and operation of a peristaltic pump is well known in the art, particularly in the field of kidney dialysis.

Figure 15:
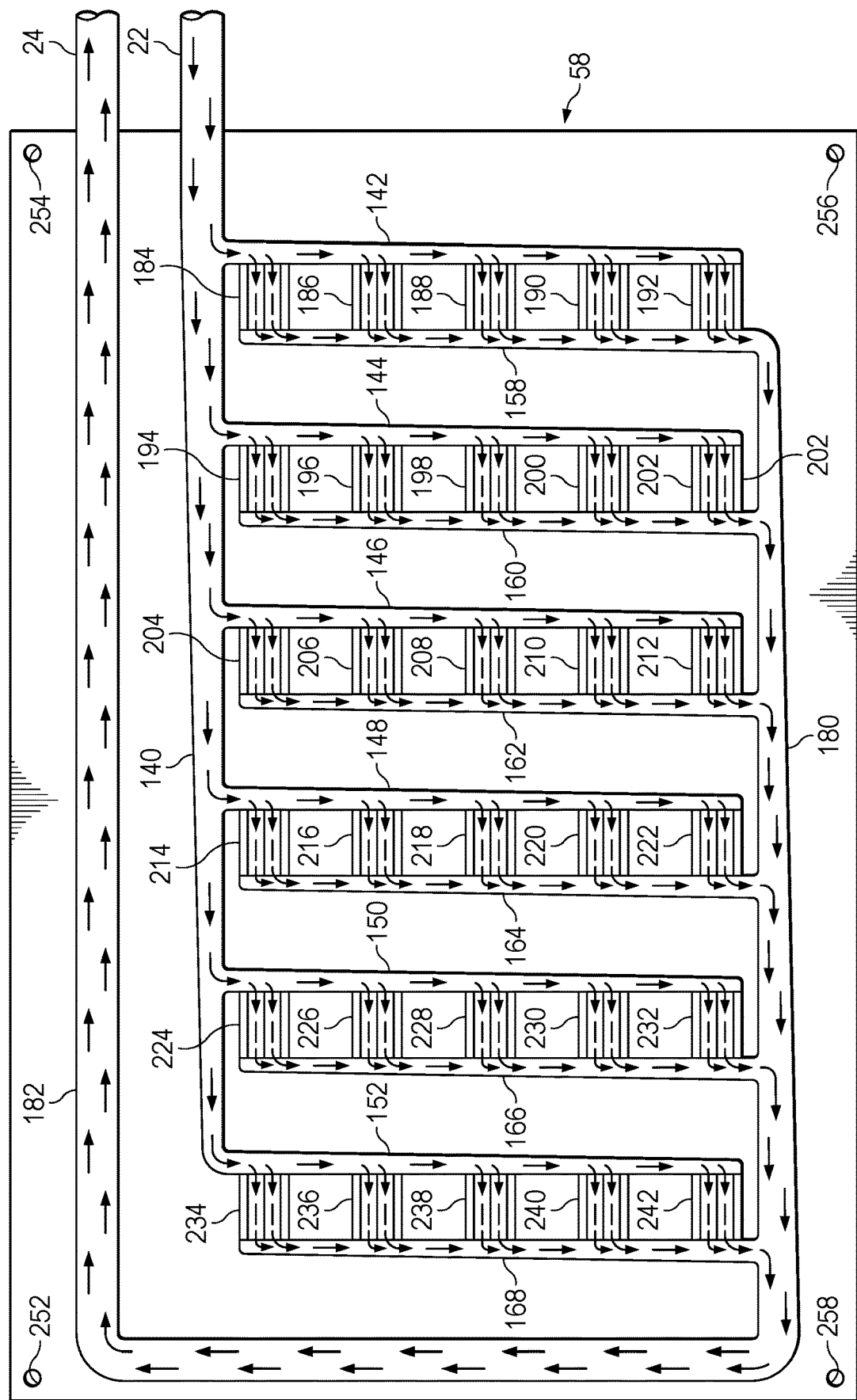
FIG. 15 is a top-down view through the top layer of the cassette, shown in FIG. 3 and FIG. 10, illustrating the flow of blood through the input manifold channels, holding chambers and output manifold channels.

The flow of blood through the lines and chambers of the cassette 58 is shown in FIG. 15. This is a bottom view of the layer 136 looking through the transparent layer 138. Blood enters the input line 22 into distribution line 140 and is sequentially distributed into the chamber input lines 142-152. Note that as the volume of blood flowing through line 140 is decreased, the size of the line 140 is correspondingly decreased. Note that each of the distribution lines 142-152 is tapered so the line size is decreased as the amount of blood flowing in the line decreases. For example, blood flowing in through input line 22 has a portion thereof directed into distribution line 142 and a portion of that flow enters holding chamber 186. As described previously, the chamber 186 is approximately 8 microns high and there are parallel ridges 248 that guide the blood in a substantially uniform flow through the chamber 186. This reduces transverse blood flow in a chamber. At the output port of chamber 186, the blood enters output line 158 where it joins the blood that has passed through chamber 184. The blood from the chambers 184 and 186 flows through output line 158 and is joined sequentially by the blood from chambers 188, 190 and 192. The blood that has flowed through the chambers 184-192 then enters the collection line 180. The blood from all of the holding chambers travels into the collection line 180 from which it flows into the cassette 58 return line 182 to the blood return line 24.

Note in FIG. 15 that the configuration of flow lines and chambers provides approximate the same travel distance for blood flowing through each of the holding chambers 184-242. In each flow path, the blood flows through or beside 10 holding chambers. For example, the blood flow through chamber 206 first passes chambers 184, 194 and 204 then flows through chamber 206 and then passes chambers 208, 210, 212, 222, 232 and 242, for a total distance of 10 chambers. This configuration contributes to uniformity of blood flow and uniformity of pressure gradient reduction for blood flow through the cassette 58.

Figure 16:
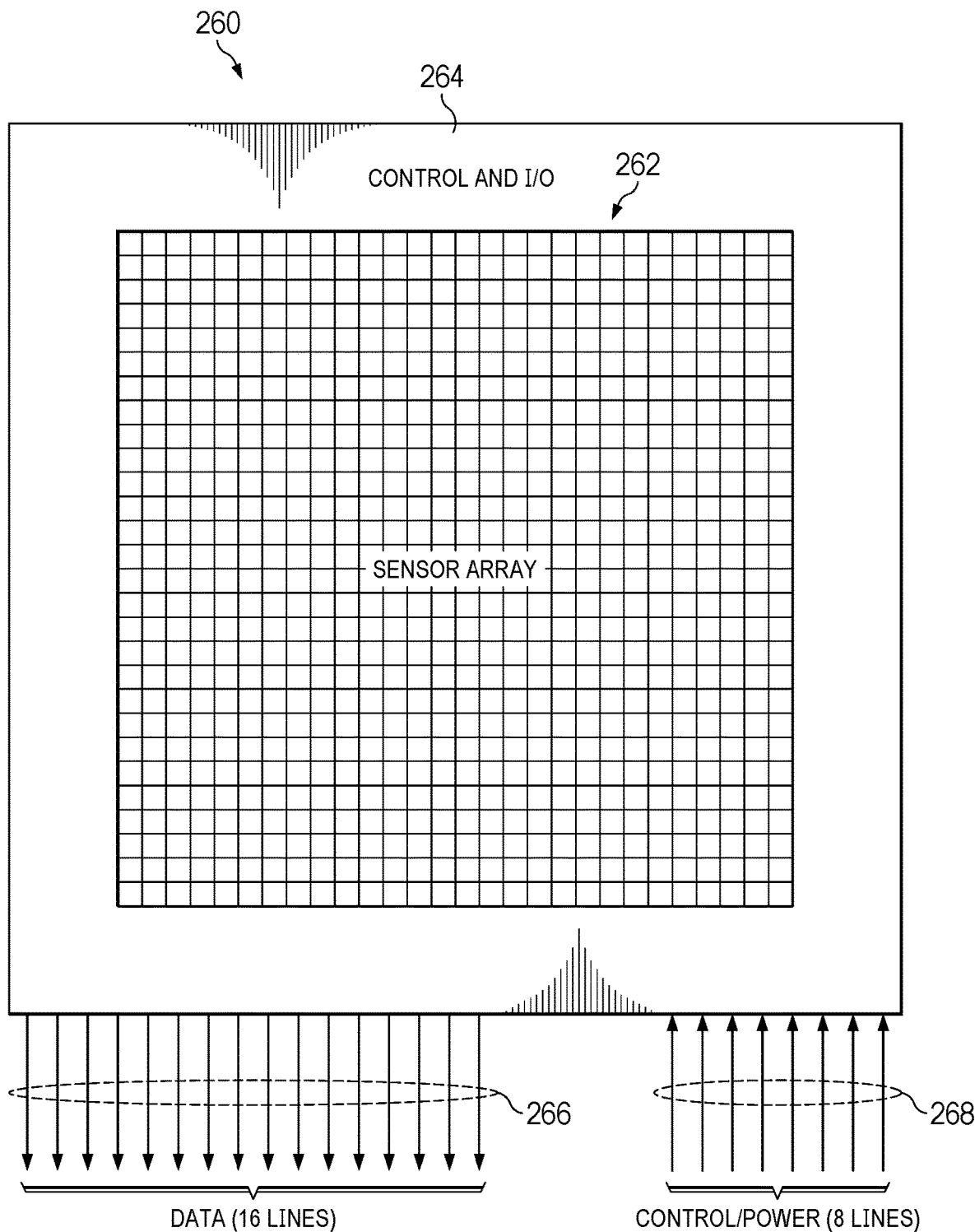
FIG. 16 is an illustration of a pixel array integrated circuit as used in the imaging and processing unit shown in FIG. 3.

An example sensor array integrated circuit for use with the present invention is shown in FIG. 16. A sensor array 260 includes an array 262 of individual pixel cells, each pixel further described below. Surrounding the array 262 of pixel cells is circuitry termed control and I/O (Input and/or Output) 264 which controls the operation of the sensor array 260 and the transfer of pixel data collected by the sensor array 260. The pixel data specifies the light intensity at each pixel location. A group of data lines 266, for example 16 parallel lines, transfers pixel data from the pixel array 262 to an associated memory. A set of control and power lines 268, for example 8 lines, controls the operation of the sensor array 260 and provides power for operation of the sensor array 260 circuitry. As further described below, the sensor array receives a reset signal to set an initial charge state in each of the pixels. When the pixels are exposed to light, each pixel is discharged from the initial state to a final state (the pixel data) depending on the amount of light that was received by the pixel. A command is sent through lines 268 which causes the sensor array 260 to transfer the collected pixel data through one or more of the lines 266 to an associated memory.

As an example, the pixel array 262 can have a pixel size of 0.5 micron by 0.5 micron (square configuration) and the array has a size of 2 centimeters by 2 centimeters. An array of this size has 1.6×10 9 pixels and, if there is only one bit per pixel, either light or dark, the pixel data is the size of the number of pixels. For a 0.25 micron by 0.25 square pixel, the number of pixels in the array is 6.4×10 9. These dimensions are exemplary only. Further, a sensor array larger or smaller than array 262, as presented, may be used.

Figure 17:
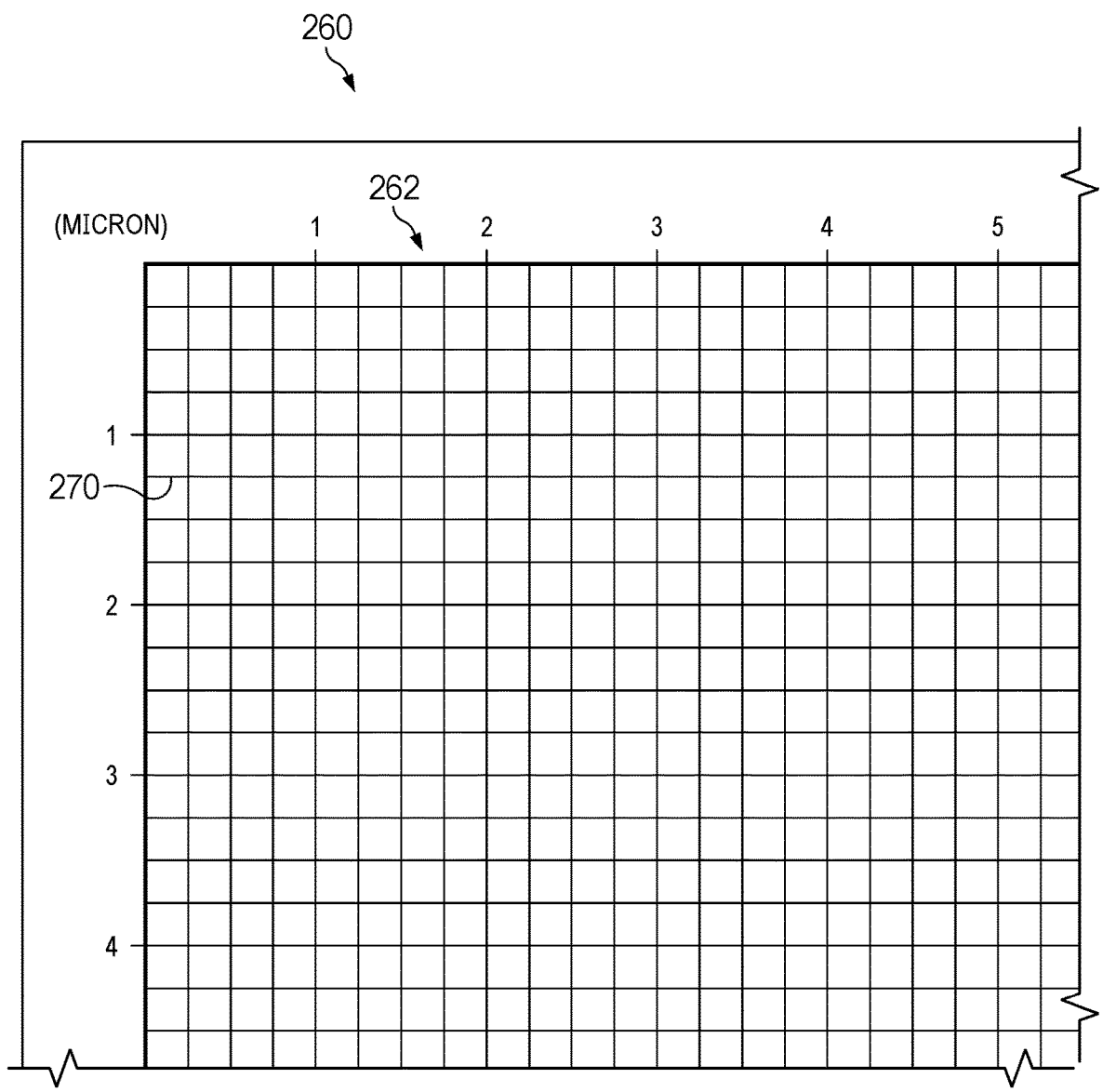
FIG. 17 is an illustration of a portion of the pixel array shown in FIG. 16.

A partial section, top view of the pixel array 262 (FIG. 16) is shown in FIG. 17. This illustration, for a design having the dimensions listed above, of a pixel array includes a dimension scale, which would not be present in an actual array, but is shown for illustration. This top left corner of the array 262 shows individual pixels, each a square having side dimensions of 0.50 micron. A single pixel, such as 270 (four squares) is representative of all of the pixels in the array 262.

A circuit for each of the pixels, such as 270, in the array 260, can be any one of many types. A 3-T (three transistor) pixel circuit is shown in FIG. 18 and a 4-T (four transistor) pixel circuit is shown in FIG. 19.

Figure 18:
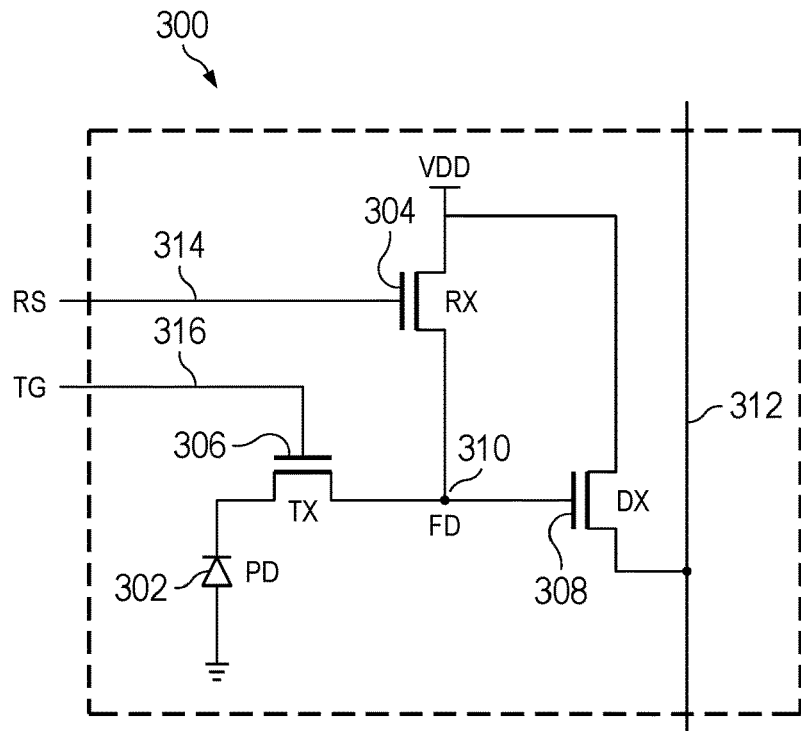
FIG. 18 is an electrical schematic of a 3T image sensor cell.
Figure 19:
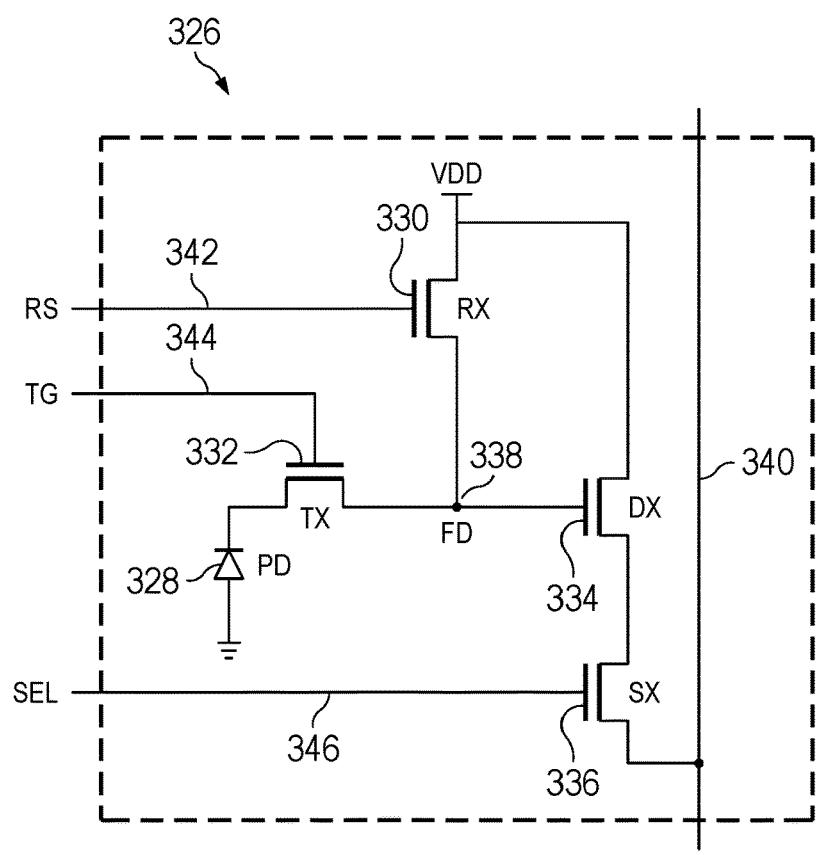
FIG. 19 is an electrical schematic of a 4T image sensor cell.

Referring to FIG. 18, a 3-T pixel circuit 300 includes a photodiode (PD) 302, a transfer transistor 306, a reset transistor 304, a drive transistor 308 and a floating diffusion (FD) 310. A reset signal (RS) is sent through a line 314 to the gate of reset transistor 304. A transfer control signal (TG) is provided through a line 316 to the gate of transistor 306. The image data produced by pixel circuit 300 is transmitted through column line 312.

In operation, the pixel circuit 300 is initially reset by turning transistor 304 (RX) on to charge node FD 310 to VDD. Next the TG signal turns on TX transistor 306 which couples the node FD to the cathode of photodiode 302. Upon receiving light at the photodiode 302, the diode reverse conducts due to holes and electrons due to the light and discharges node FD dependent upon the amount of light received by the diode. The remaining charge on node FD drives the transistor 308 (DX) which applies a corresponding current to the column line 312.

A 4-T pixel circuit 326 is shown in FIG. 14. This circuit has a photodiode (PD) 328, a reset transistor 330 (RX), a transfer transistor 332 (TX), a drive transistor 334 (DX), and a select transistor 336 (SX). A floating diffusion 338 (FD) is connected to the gate of transistor 334. Transistor 330 (RX) receives a reset signal through line 342. Transistor 332 (TX) receives a drive signal (TG) through a line 344. Transistor 336 (SX) receives at its gate a select control signal (SEL) via a line 346.

The pixel data, which is the measured light, is sent through the column lines 312 and 340 in FIGS. 18 and 19. At the end of these lines there is an analog to digital converter to produce a high or low, 1 or 0, digital signal. This is essentially a threshold detection. Each pixel data represents dark or light, depending on how much light was received at the pixel.

Operation of the pixel circuit 326 (FIG. 19) begins with receipt of a reset (RS) signal at transistor 330 to charge node FD 338 to VDD. Next, the transfer control signal (TG) turns on transistor 332 to couple the cathode of photodiode 328 to node FD. When the photodiode 328 receives light, charge is drawn from node FD to reduce the voltage on node FD, which drives the gate of transistor 334 (DX). For readout of data from the pixel, signal SEL is applied to turn on transistor 336 (SX) to couple transistor 334 (DX) to the column line 340. The column line 340 is sequentially used to transfer data from all of the pixels connected to the column line.

Figure 20:
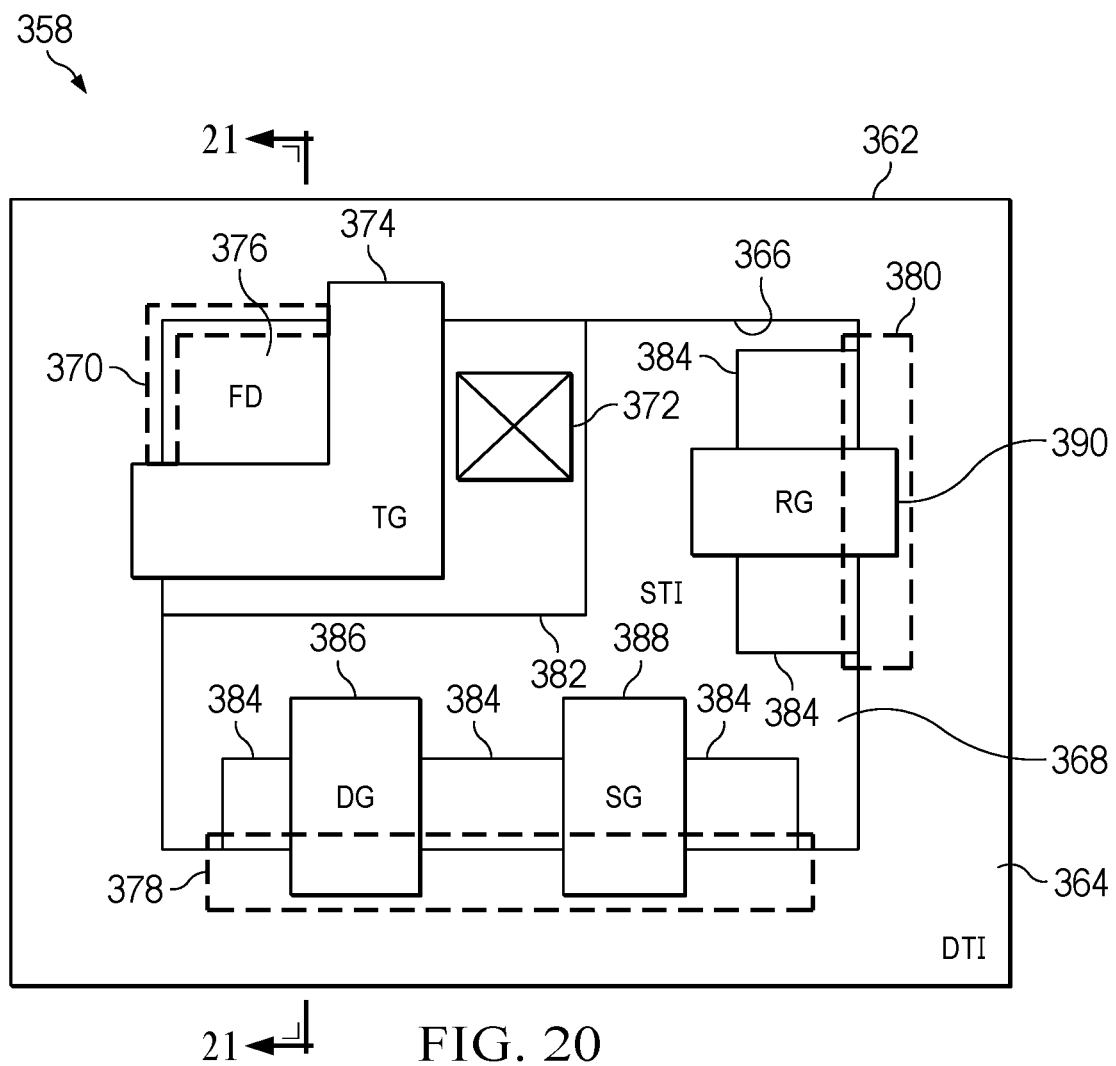
FIG. 20 is a top view of a layout of an image sensor cell.
Figure 21:
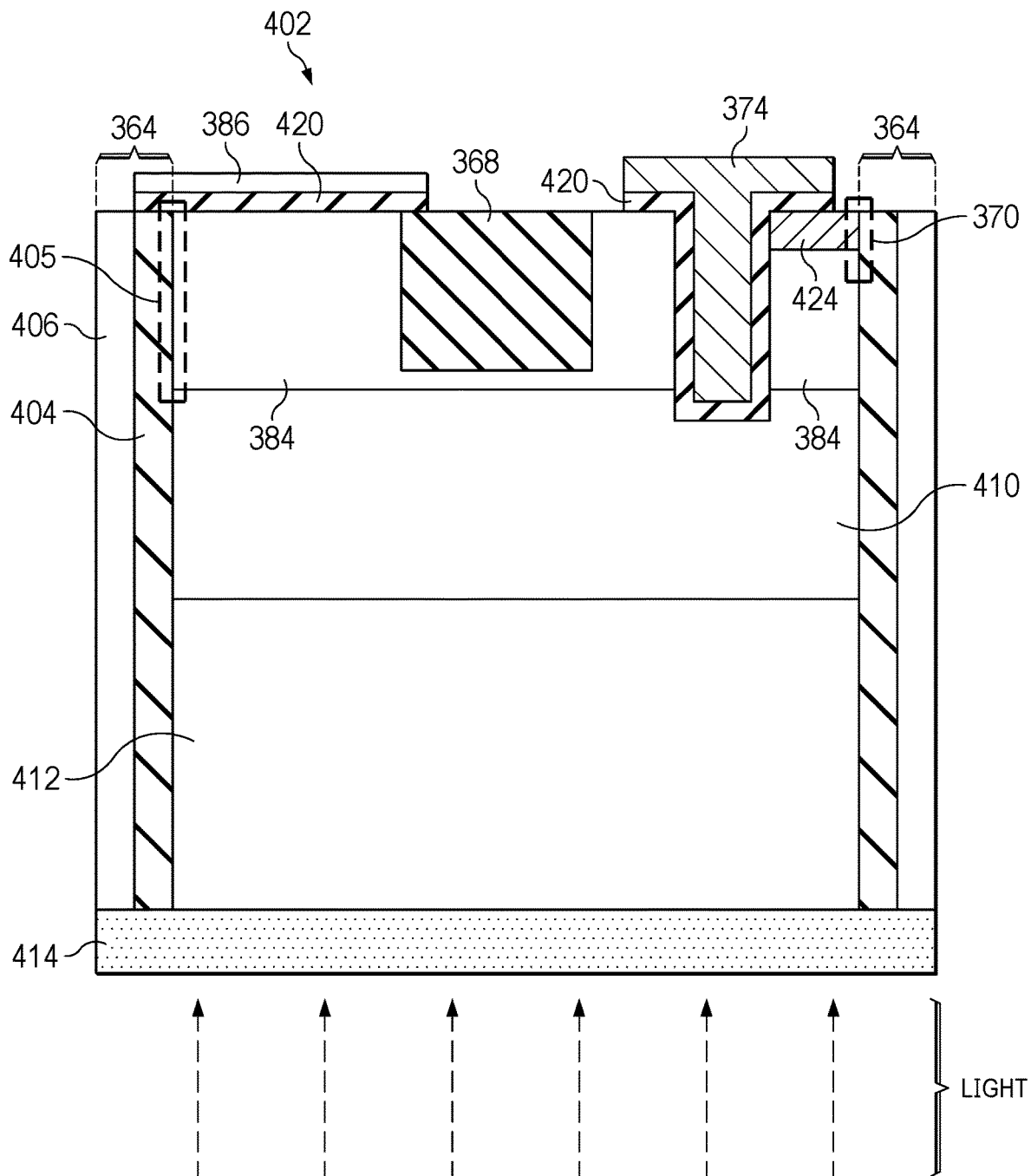
FIG. 21 is a section view of a layout of an image sensor cell.

FIGS. 20 and 21 illustrate a physical integrated circuit structure for implementing the 4-T pixel shown in FIG. 19. Layout 358 in FIG. 20 is a top view. A unit pixel area 362 is the area occupied by the pixel structure. A deep trench isolation (DTI) region 364 serves to isolate each pixel from surrounding pixels. Active area 366 is the area of the pixel which receives light. A shallow trench isolation (STI) 368 separates active elements of the pixel. First border 370, second border 378 and third border 380 serve to isolate elements of the pixel circuit to reduce noise. 372 is a ground element. 374 is a transfer gate. 376 is a floating diffusion. 382 is a p-well. 384 is a p-well. 386 is the drive transistor gate. 388 is the select transistor gate and 390 is the reset transistor gate.

FIG. 21 is a section view layout 402 along line 21-21 of the structure shown in FIG. 20. The common elements in FIGS. 20 and 21 have the same reference numerals. Element 404 is an oxide isolating layer, 405 is a border, 406 is a polysilicon isolation layer and 410 is a photodiode in conjunction with the epitaxial layer 412. Element 414 is an anti-reflection layer. 420 is a gate isolation layer. 424 is a floating diffusion (FD 338 in FIG. 19). Light, shown by the upward pointing vertical arrows in FIG. 21, produced by the light source (54 in FIG. 3), is transmitted to the pixel structure and in particular to the photodiode for measuring the light received by this one pixel.

A schematic and physical structure for a light receiving pixel is described in U.S. Pat. No. 9,420,209 issued Aug. 16, 2016 which is incorporated herein by reference in its entirety.

Figure 22:
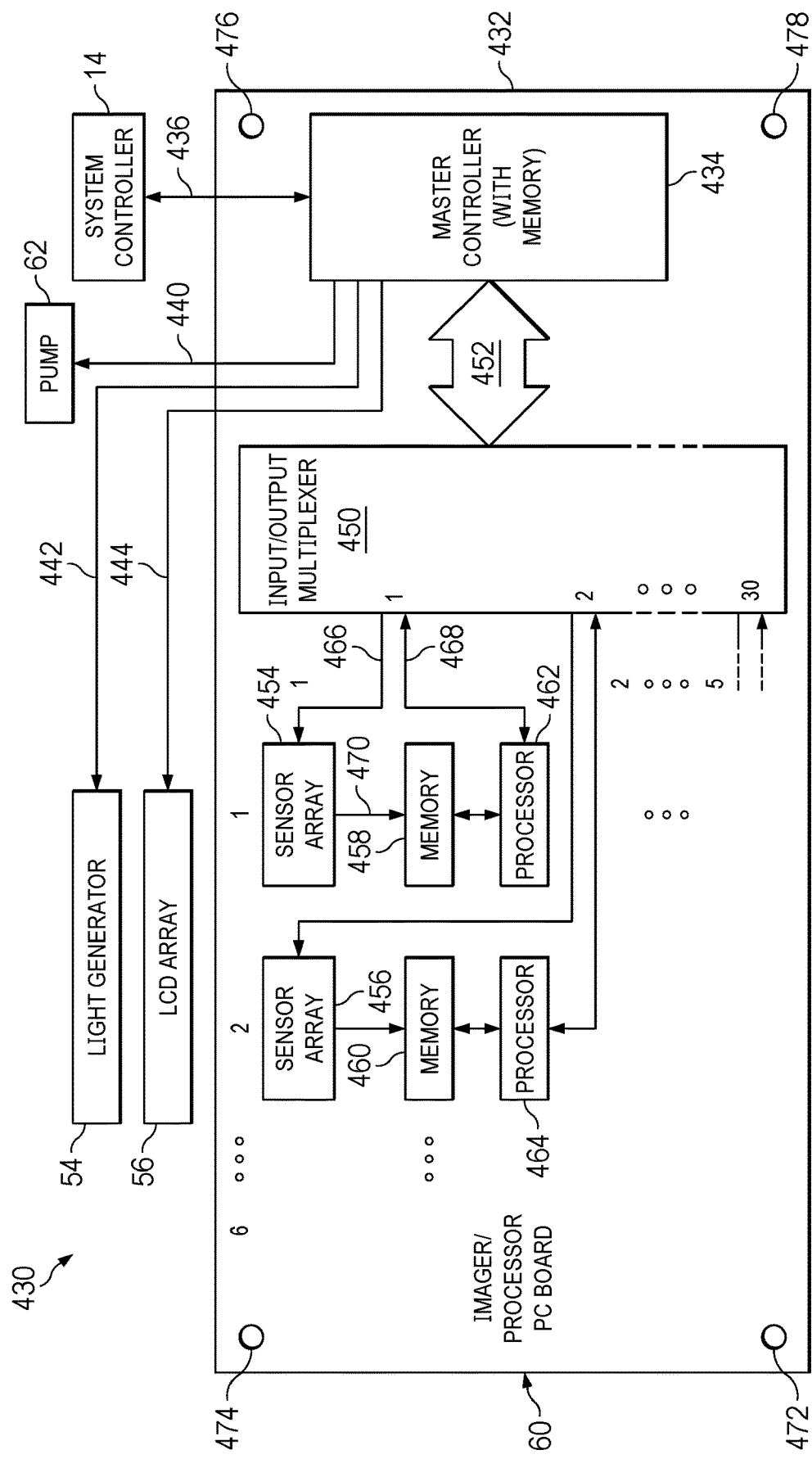
FIG. 22 is a system electrical schematic.

A system electrical schematic 430 for an embodiment of the invention is shown in FIG. 22. The imager and processor unit 60 comprises a printed circuit board 432 having multiple integrated circuits mounted thereon. A first component is a microprocessor master controller 434 having on-board memory. Master controller 434 is coupled via a multi-line cable 436 within cable 12 to the system controller 14. Controller 434 is connected by a control line 440 to pump 62 such that the controller 434 can operate the pump 62. The controller 434 is further connected via a line 442 to the light source 54 for operating the light source to selectively produce visible or UV collimated light. The controller 434 is further connected through a line 444 to the LCD array 56 to selectively activate the shutters of the array 56. Each of these lines can have multiple conductors for carrying the required control signals.

An input/output multiplexer 450 is mounted on the board 432 and connected to the master controller 434 via a multi-line bidirectional bus 452. The bus 452 can comprise multiple printed circuit trace lines. Also mounted on board 432 is an array of sensor arrays, and two sensor arrays 454 and 456 are shown as examples for the full set of sensor arrays. The entire array has 6 columns of sensor array assemblies with 5 sensor array assemblies in each column, for a total, in this embodiment, of 30 sensor array assemblies. Each sensor array is coupled to a corresponding memory, sensor array 454 is connected to a memory 458 and sensor array 456 is connected to memory 460. For each sensor array, there is also a corresponding processor, sensor array 454 has a corresponding processor 462 and sensor array 456 has a corresponding processor 464. Each sensor array has a bus of parallel lines connected from the sensor array to the corresponding memory. For example, sensor array 454 is connected to memory 458 through a bus 470 (FIG. 22). For the entire array of sensor array assemblies, in this embodiment, there are 30 sensor arrays, 30 memories and 30 processors.

The board 432 has alignment holes 472, 474, 476 and 478 that physically align with the alignment holes 252, 254, 256 and 258 of the cassette 58, see FIGS. 3 and 10. The board 432 and cassette 58 are mounted on the four vertical rods 30, 32, 34 and 36 (See FIG. 2) in the operational unit 10 so that each of the chambers in the cassette 58 align with a corresponding sensor array on the board 432.

Further in reference to FIG. 22, viewing sensor array 454 and its corresponding memory and processor as an example assembly, each assembly is connected to the multiplexer 450. A control line 466 is connected between the multiplexor 450 and the sensor array 454. A bidirectional bus 468 is connected between the multiplexer 450 and the processor 462. There are likewise similar lines between the multiplexer 450 and each of the other sensor assemblies mounted on the board 432. The multiplexer 450 can be commanded to connect the controller 434 to any one of the sensor assemblies or to multiple assemblies concurrently.

Figure 23:
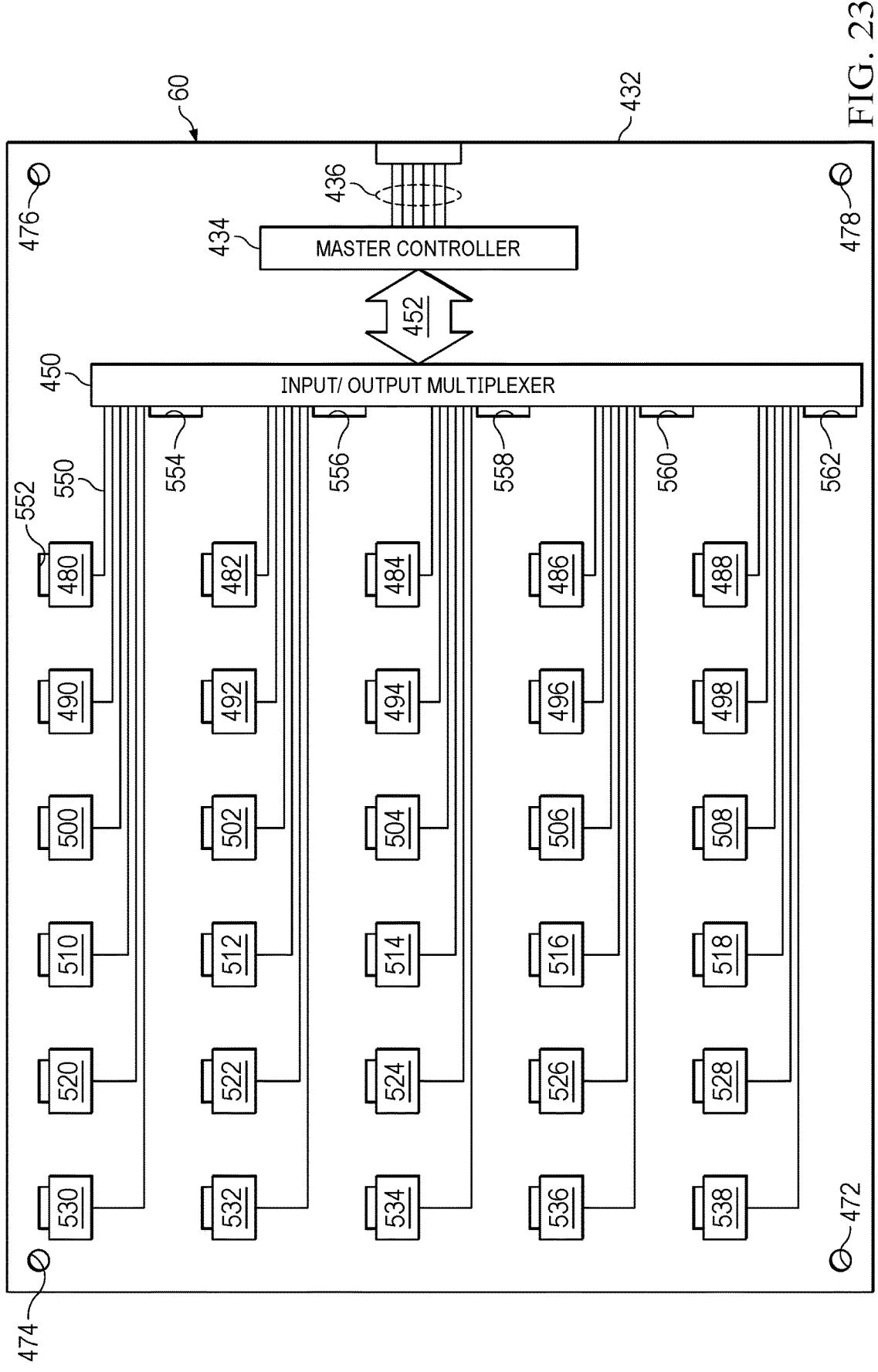
FIG. 23 is a top view of an imager and processor unit printed circuit board as shown in FIG. 3.
Figure 24:
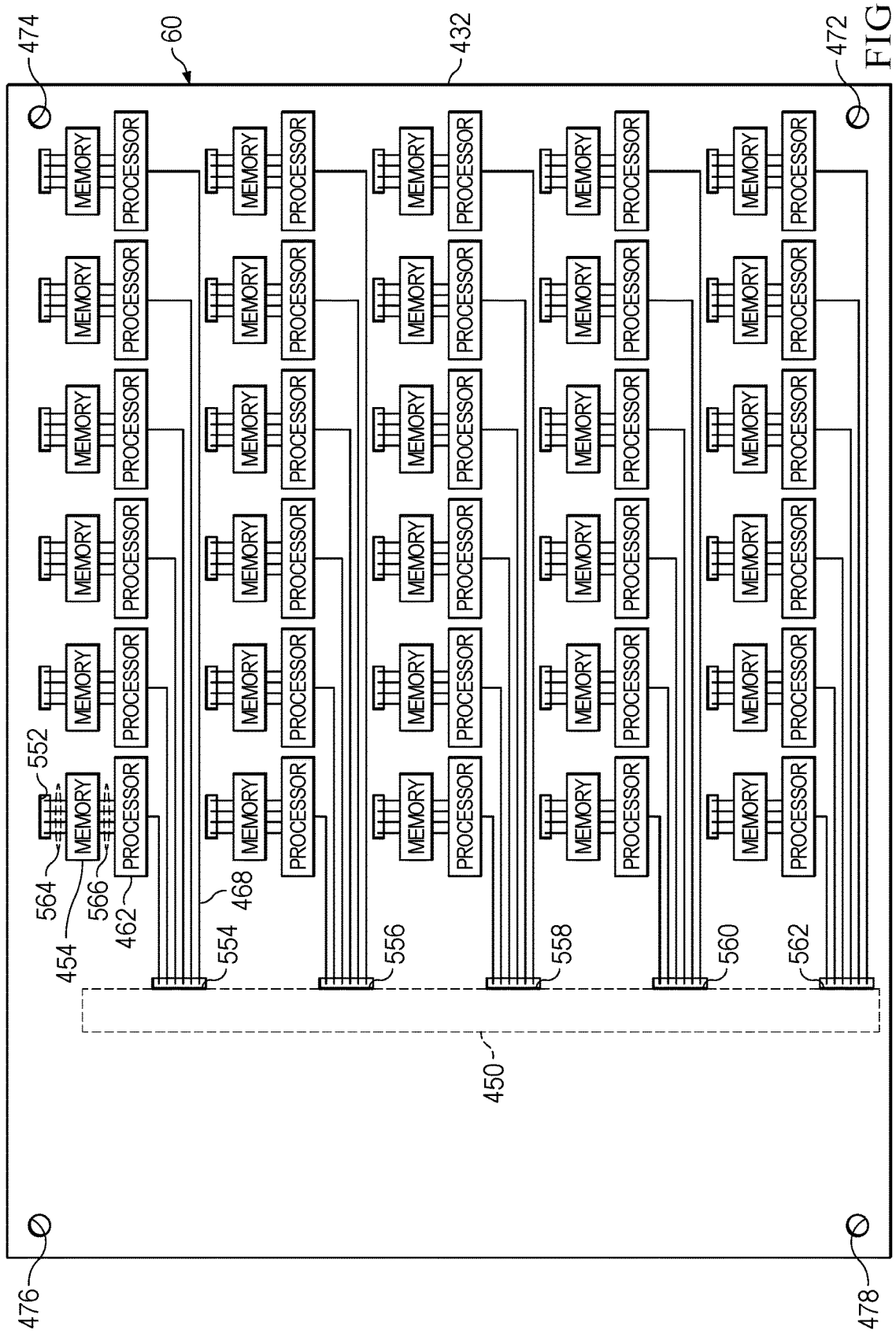
FIG. 24 is a bottom view of an imager and processor unit printed circuit board as shown in FIG. 3.

A physical configuration for the image and processor unit 60 (see FIGS. 3 and 22) is shown in FIGS. 23 and 24. The controller 434 and multiplexer 450 are mounted on the printed circuit board 432. An array of sensor arrays 480, 482, 484, 486, 488, 490, 492, 494, 496, 498, 500, 502, 504, 506, 508, 510, 512, 514, 516, 518, 520, 522, 524, 526, 528, 530, 532, 534, 536 and 538 are configured in a rectangle with six columns and five sensor arrays in each column. Each sensor array has a control line from the array to the multiplexer 450, for example, sensor array 480 has control line 550. Each of the control lines to the sensor arrays is one or more traces on the printed circuit board 432.

Each of the sensor arrays 480-538 has a bus of parallel line traces connecting the sensor to its corresponding memory. Alternatively, a high-speed serial bus can be employed. In FIG. 23, a section of the bus comprises through-hole conductors, such as through-hole conductors 552 for array 480, pass through the printed circuit board 432 to the opposite side. Each sensor array has such a set of through-hole conductors for connecting through the board 432 to the corresponding memory. (FIG. 23)

Referring to FIGS. 23 and 24, the multiplexer 450 has through-hole conductors 554, 556, 558, 560 and 562. As shown in the FIG. 17 electrical schematic, each sensor array is connected to a corresponding memory and each memory is connected to a corresponding processor. Each memory and processor for each of the sensor arrays 480-538 are shown in FIG. 24. As an example, for all of the sensor arrays, sensor array 480 is connected via through-hole conductors 552 to conductors 564 to memory 454 on the opposite of board 432 from sensor array 480. The memory 454 (FIG. 24) is connected via conductors 566 to the processor 462. Processor 462 is connected by a bus 468 to the through-hole conductors 554 to the multiplexer 450. All of the remaining memories and processors are similarly connected via the through-hole conductors 554, 556, 558, 560, and 562 to the multiplexer 450.

The processors described herein, one used with each sensor array, can be, for example, a microcomputer, a graphic processor or a custom gate array. The master controller can be, for example, a microcomputer or a custom gate array. An alternative configuration can utilize one processor for multiple sensor arrays, for example, one processor for each column of sensor arrays. A further configuration has one processor for all of the sensor arrays. A still further configuration has a master controller that includes the processing described for all of the chamber processors.

The 30 sensor arrays shown in FIG. 23 each align with a holding chamber in cassette 58 (see FIG. 10). There is a one-to-one relationship. For example, holding chamber 184 (FIG. 10) is positioned over and aligned with sensor array 480 (FIG. 23). Each of the remaining holding chambers (FIG. 10) of the cassette 58 is likewise located over and aligned with a sensor array (FIG. 23).

Operation of the invention can include an initial calibration of the light energy produced from the light source 54 to be sufficient to activate the individual pixels in the sensor arrays 480-538 shown in FIG. 23. Also referring to FIG. 3, as directed by the master controller 434, after receiving an energy calibration command from the system controller 14, the energy calibration process first resets all of the pixels in all of the sensor arrays, then opens all of the shutters in the LCD array 56, activates all of the pixels in all of the sensor arrays and then activates the visible light generation from the light generator 54 for a selected time and intensity. The pixels in the sensor arrays are then deactivated, the pixel data transferred to the corresponding memory and the corresponding processor activated to run a light energy calibration routine. If the light energy is sufficient, all of the pixels will be light, that is, no dark pixels since there is nothing in the cassette holding chambers during this calibration process. The processor counts the number of dark pixels. The master controller polls all of the processors to collect the number of dark pixels. If the number of dark pixels exceeds a preset threshold, such as 0.001%, the calibration process is repeated and the selected light source time is incrementally increased and the process repeated until the number of dark pixels is less than the preset threshold. If the initial measurement shows the number of dark pixels to be less than the present threshold, the process is repeated with shorter light activation times until the threshold is crossed and the last lower value is selected as the light activation time. The light energy can be varied by changing the length of time the light is on, or by varying the intensity of the light. In either case, a light activation value, with time and intensity, will be produced.

Figure 25:
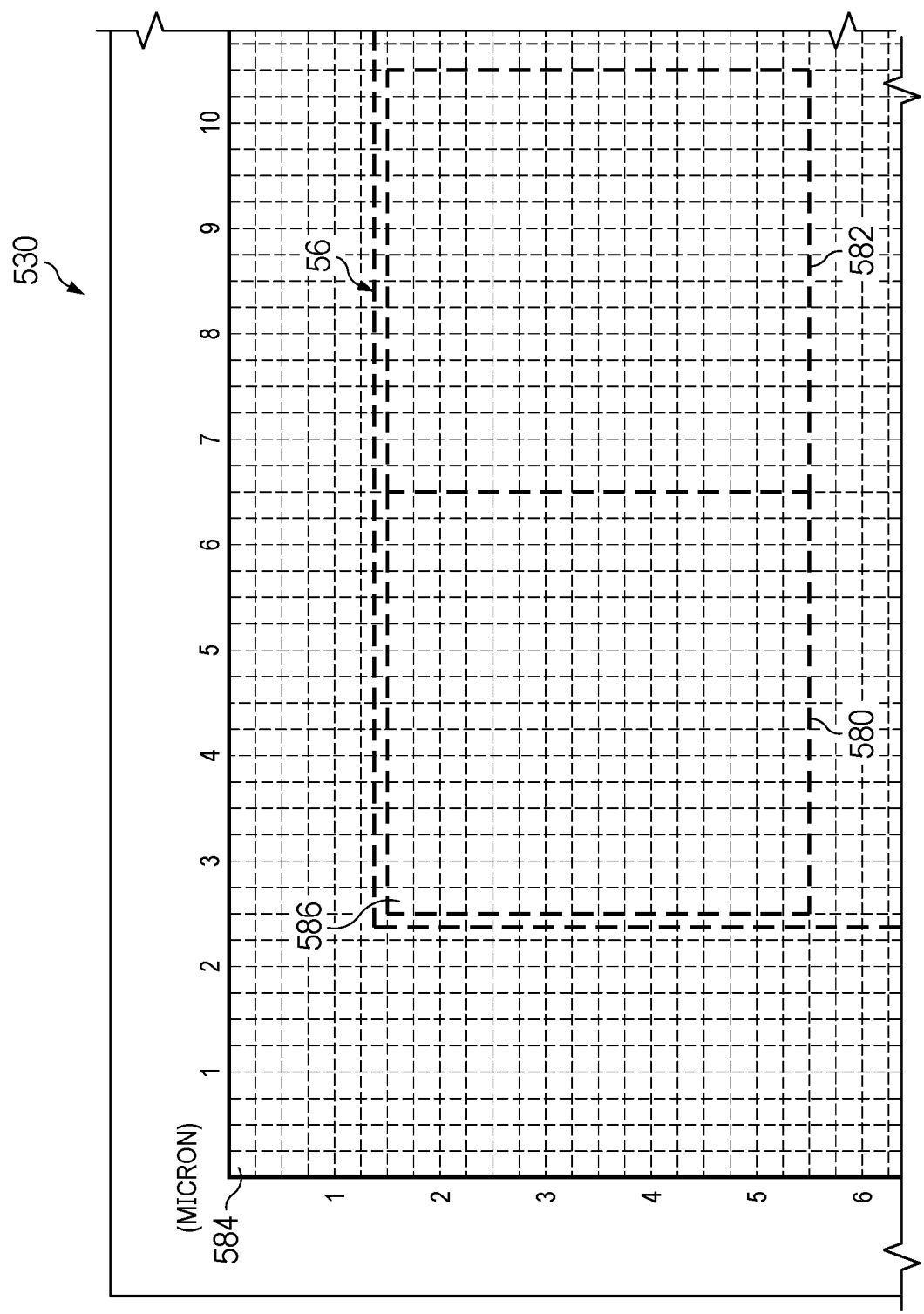
FIG. 25 is an illustration of portions of an LCD array and a pixel array for showing an alignment process.

The LCD shutters shown in array 56 (FIG. 8) preferably are perfectly aligned with the sensors arrays 480-538 (FIG. 23) but in practice there may be physical misalignment. FIG. 25 illustrates LCD shutters 580 and 582. These are a part of the LCD shutter array 56, shown in FIG. 8. In this embodiment, each shutter is square and has a side dimension of 4 microns. The shutters are illustrated as dotted lines to show the shutter overlay of the sensor 530 (FIG. 23). In FIG. 25, the shutters 580 and 582 are not precisely aligned over the sensor array 530. If in precise alignment, the upper left corner of shutter 580 would be over pixel 584 of the sensor array 530. Table 1 below illustrates an ideal perfect alignment. To compensate for misalignment, a calibration table (Table 2) is produced as shown below. The positions are indicated as a count of quarter micron units. For example, the top left corner of shutter 580 is at position (07:11). The first digit is vertical down and the second digit is horizontal to right. The corners of each array are given as top left/top right/bottom left/bottom right.

TABLE 1

| LCD Shutter Number | Pixel Area Aligned |
| --- | --- |
| 1 (580) | 00:0/00:16/16:00/16:16 |
| 2 (582) | 00:16/00:32/16:16/16:32 |

TABLE 2

| LCD Shutter Number | Pixel Area Not Aligned |
| --- | --- |
| 1 (580) | 11:07/07:26/22:11/22:26 |
| 2 (582) | 07:27/07:42/22:27/22:42 |

Figure 26B:
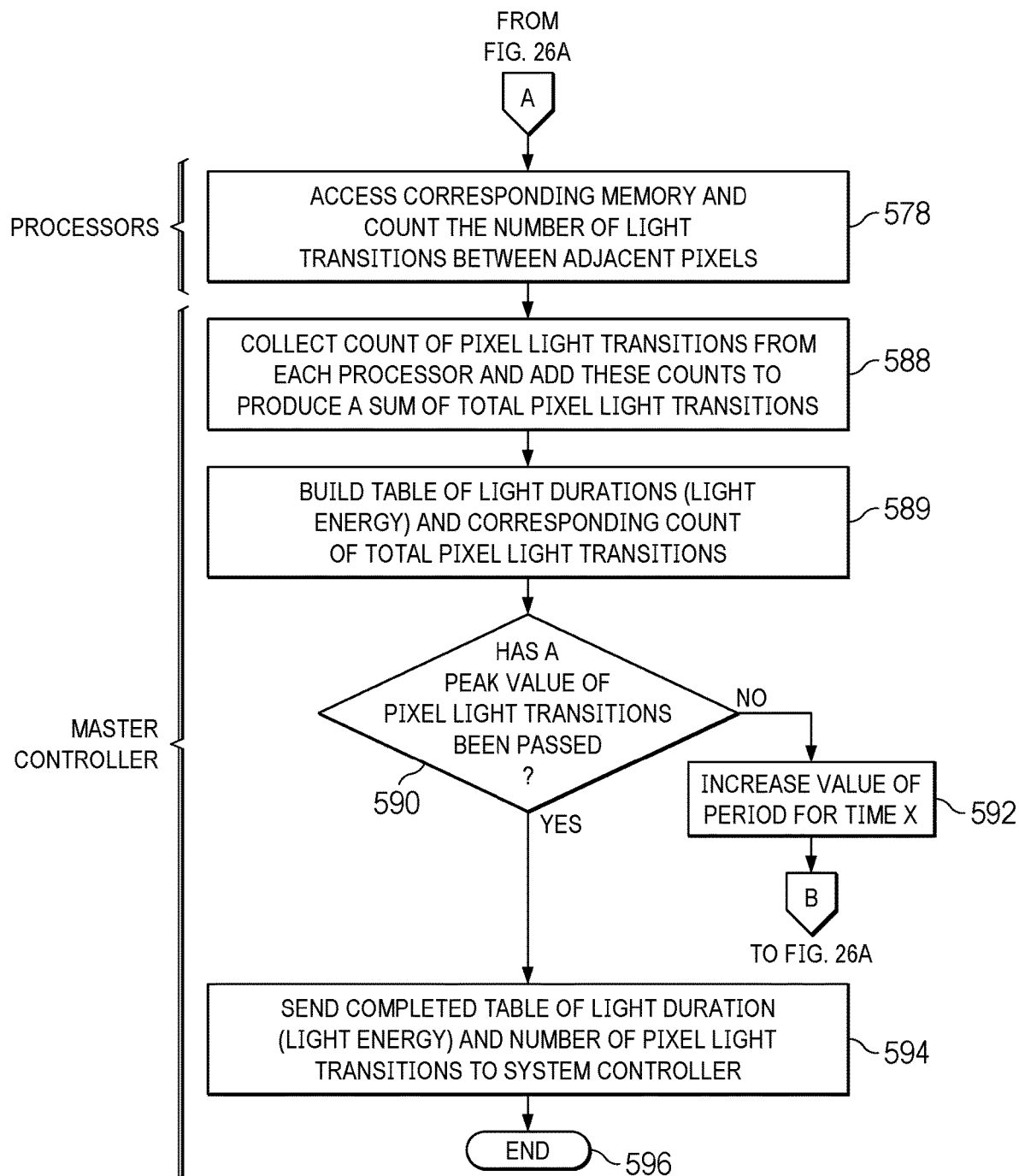

Referring to FIGS. 26A and 26B, in a calibration process, the master controller resets sensor array 530, opens a single shutter, such as 580, activates the light generator 54 to produce visible light, activates the pixels in sensor array 530 and then deactivates the pixels in the array, deactivates the light array 54 and closes the shutter 580. The master controller then commands the sensor array 530 to transfer the collected pixel data to the corresponding memory and the master controller then commands the corresponding processor to send the pixel data in the memory to the master controller 434. The pixel data from sensor 530 is then transferred to the system controller 14. The first pixel, top left, in the pixel data corresponds to pixel 586 in the sensor 530. The alignment offset is the position difference between pixel 584 and pixel 586. In this example, it is a down offset of 17 pixels and a right offset of 11 pixels. The area coverage can now be calculated for the shutter 580. In FIG. 21, the shutters are number 1—(total number of shutters). Shutter 580 corresponds to shutter "1". The pixel area covered by the shutter 580 is shown in the horizontal line under "Pixel Area Not Aligned" as four-pixel locations representing the pixels at the top left, top right, bottom left and bottom right of the shutter. In this case, for shutter 580, the calibration table data is 11:07/07:26/22:11/22:26. This process is repeated for each shutter of the LCD array 56 for all of the sensor arrays. If there is any misalignment between an LCD array and corresponding sensor pixels, this calibration process provides a correction to accurately locate any image found in the holding chambers. Therefore, for example, if a cell image is found in the pixel array area of 11:07/07:26/22:11/22:26, shutter 580 will be opened to pass UV light to the pathogen cell identified and located in the holding chamber.

Light energy calibration can also be performed after the blood holding chambers have been filled as shown by the steps in FIGS. 26A and 26B. The system controller initiates the filled chambers light energy calibration by sending a command to the master controller 434. See step 568. The controller 434 receives the command at step 569. Referring to FIGS. 22 and 23, the controller 434 drives the pump 62 to fill the holding chambers in cassette 58 (FIGS. 3 and 15). See step 570. After the pump 62 is stopped the controller 434 (step 571) commands all of the shutters of the LCD array 56 be opened. Next, in step 572, the controller 434 sends a reset command to each of the sensor arrays 480-538. After the pixels in each sensor are reset, the controller 434 commands (step 573) each sensor array to be activated. Next, in step 74 the light generator 54 is activated for a period of time X. The controller 434, in step 575, deactivates all of the sensor arrays, and in step 576 commands each sensor array to download its pixel data to the corresponding memory. Next, in step 577, the controller commands each processor associated with a sensor array to (step 578) access the pixel data in the corresponding memory and perform a light calibration process in which the number of light transitions between adjacent pixels is counted. The transition can be either light to dark or dark to light. Each pixel has four adjacent pixels and each possible transition is examined. For example, a dark pixel surrounded by four light pixels produces four transitions. In step 588, the controller 434 then collects the pixel transition count from each processor and adds them together to produce a total transition count corresponding to the period of time the light generator was on. In step 589, the master controller produces a table of light durations and pixel transitions as shown below in Table 3. Next the above process is repeated with an incrementally longer period of time for the operation of the light source. The number of transitions for this period is determined and recorded. Next, in question step 590, it is determined if the peak value of the number of light transitions has been passed. This is selected, for example, by having 50-70, sequential transition counts lower than a preceding transition count. If the response to question step 590 is "NO", in step 592, the value of X is increased by a selected increment, and control is returned to step 571. This process is repeated until a peak of transition number is reached, as noted. If the response to question step 590 is "YES", the master controller 434, in step 594 sends the completed table of light duration and count of pixel transitions to the system controller 14. This calibration process terminates at STOP step 596. An example of such data is as follows. The light energy value is a relative measure and the Pixel Transitions number is a truncated value, such as billions of transitions.

TABLE 3

| Relative Light Energy | Pixel Transitions |
|---|---|
| 1 | 50 |
| 2 | 65 |
| 3 | 85 |
| 4 | 100 |
| 5 | 120 |
| 6 | 140 |
| 7 | 150 |
| 8 | 165 |
| 9 | 160 |
| 10 | 150 |
| 11 | 135 |
| 12 | 125 |
| 13 | 115 |
| 14 | 105 |
| 15 | 90 |

As seen in the above data listing, the optimum light energy value is "8" which corresponds to the pixel transition value "165". The number of pixel transitions is an indicator of the quantity of image information present in the pixel data and is likely the best image data. Therefore, for this instance of testing, the light energy should be set to the relative level of "8" for the process described herein to identify and locate pathogen cells in the blood. As noted above, the light energy can be varied by time duration or by the intensity of the light produced.

Referring to FIG. 22, in a brief description of operation, the controller 434 drives the pump 62 to fill the holding chambers in a cassette 58 (See FIGS. 3 and 15) with blood. When the holding chambers are filled, the pump is stopped. Next the controller 434 commands that all of the LCD shutters of LCD array 56 be opened. The controller sends a reset command to each sensor array to reset all of the pixels in each array. Next, the controller sends an activation command to all pixels in all sensor arrays. After this, the controller 434 activates the light generator 54 to produce visible light for a set period of time. When this time has elapsed, the controller 434 sends a control signal to all pixels in all sensor arrays to end activation. Next, the controller sends a command to each sensor array to download the collected pixel data to the corresponding memory. After the pixel data has been loaded in the memories, the controller 434 commands each of the processors mounted on board 432 to process the pixel data in the corresponding sensor array for pattern recognition using an image library. Each processor determines the location in the chamber for each identified image and determines which LCD shutter corresponds to that location. The controller 434 then downloads from all of the processors the list of LCD shutters. Next the controller 434 commands the LCD array 56 to open all of the shutters that are listed in the multiple lists provided by all of the processors. Next, the controller 434 activates the light generator to produce UV light for a predetermined length of time. Finally, the controller commands the LCD array 56 to close all of the shutters. Thus, selected pathogen cells in the blood, recognized from the image library have been identified, located and exposed to UV light for sufficient time to neutralize (kill) the cells. For killing *E. coli*, the UV light can, for example, have a wavelength in the range of 250-265 nanometers and have an applied intensity in the range of 2-10 milli-joules per square centimeter.

Figure 27:
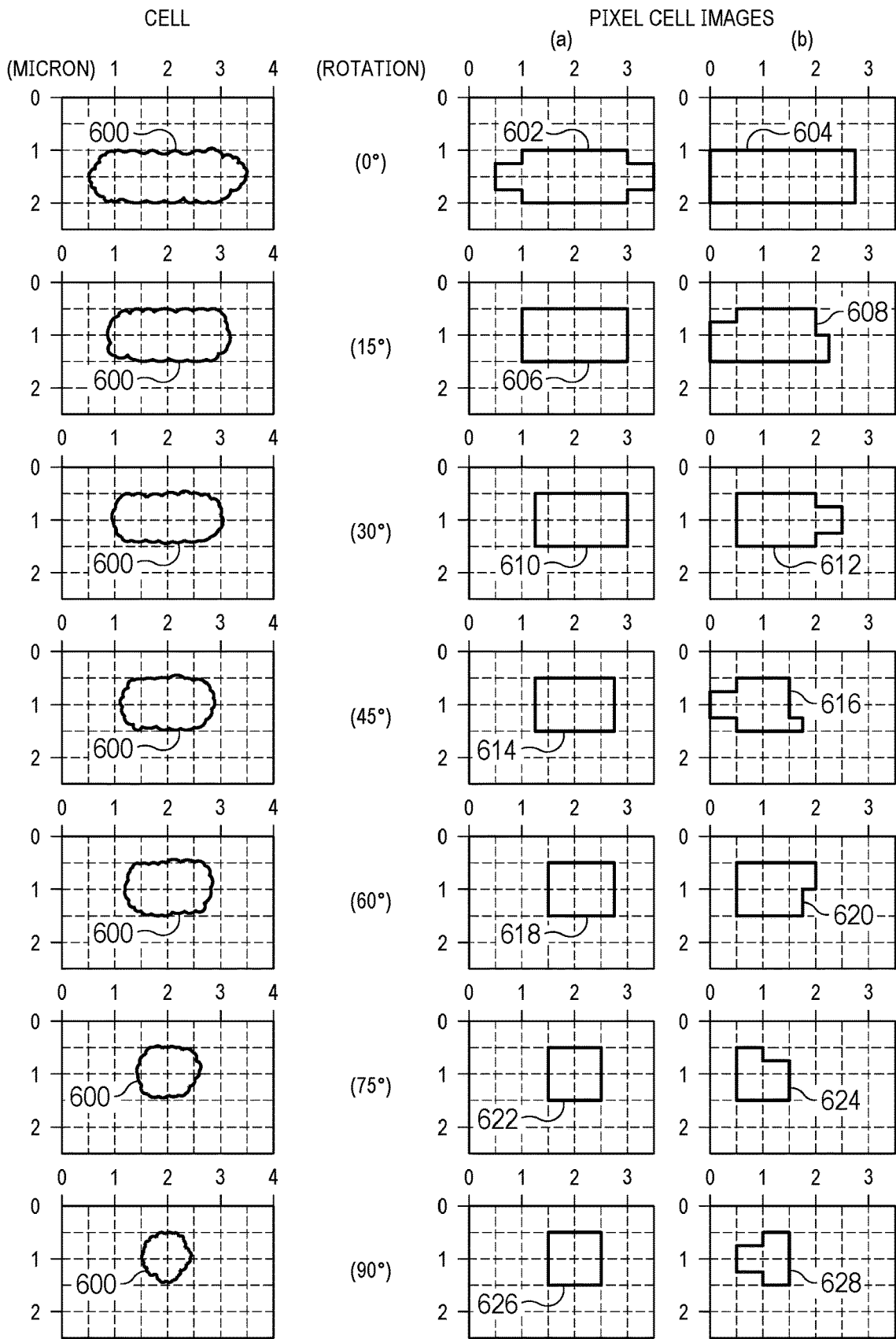
FIG. 27 is a set of pathogen image views for pattern recognition.

A pathogen cell, together with a measurement scale, is shown in multiple positions in FIG. 27. *E. coli* is a rod-shaped bacterium. The dimensions for this bacterium can vary but some species can be in the range of 2-3 microns long and 0.25 to 1 micron thick. In FIG. 27, there is shown in the left column an *E. coli* bacteria cell 600. The left column shows an actual view of a cell and the two right columns show shadow images that can be produced by that view of the cell by the sensor arrays (FIG. 23). These views are based on a system as described with 0.50-micron by 0.50-micron sensor array pixels. The right two columns show shadow images produced by the corresponding cell in the left column. The cell 600 is shown at multiple rotations along a vertical axis with angles of 0, 15, 30, 45, 60, 75 and 90 degrees. These multiple views are required because the cell could be at any rotation position as it is viewed in a holding chamber. The right two columns (a) and (b) represent possible variations on the image produced by the cell positioned at the indicated rotation. Images 602 and 604 can be produced by cell 600 at rotation of 0 degrees. These can differ due to edge effects and small threshold differences in pixel sensors. Images 606 and 608 could be produced for rotation 15 degrees, 610 and 612 for rotation 30 degrees, 614 and 616 for 45 degrees, 618 and 620 for 60 degrees, 622 and 624 for 75 degrees and 626 and 628 for 90 degrees. The images 602-628 are the image library for the pathogen cell 600. These images are the search targets in the pixel data for identifying and locating the pathogen cells. These images can be located in the pixel data by the use of pattern recognition. Pattern recognition for detecting predetermined images in a digital data field is well-known technology. An example patent describing such technology is U.S. Pat. No. 9,141,885 issued Sep. 22, 2015 which patent is incorporated herein by reference in its entirety.

Figure 28:
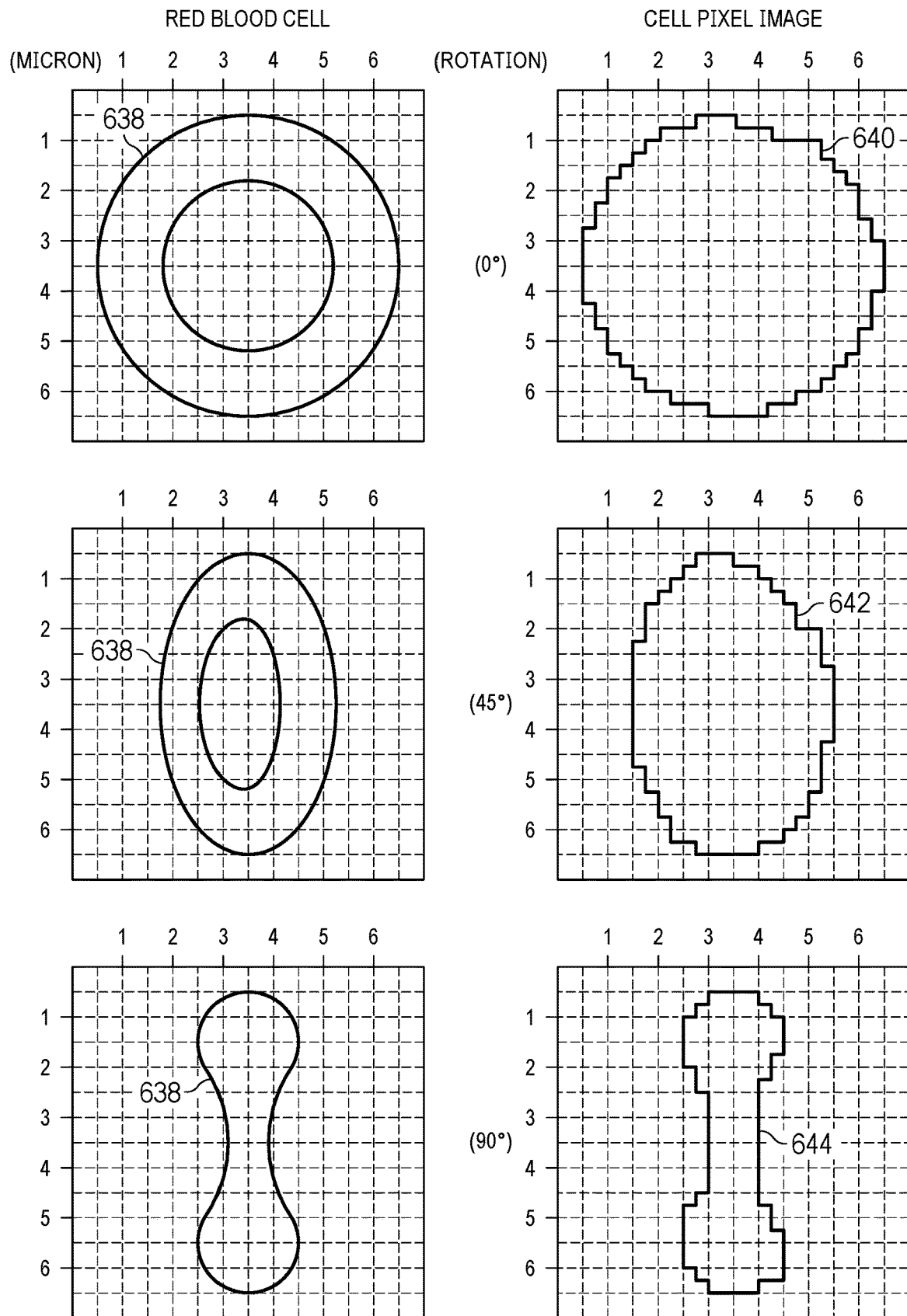
FIG. 28 is a set of red blood cell images for pattern recognition.

Referring to FIG. 28, there are shown views of corresponding shadow images of red blood cells, which comprise the majority of cells in human blood. The size of red blood cells can vary, but can be in the range of 6-8 microns. In FIG. 28, left column, there is shown a red blood cell 638. A red blood cell has a disc shape with a flattened center where the thickness may be 1-2 microns. Cell 638 with a rotation of 0 degrees can produce the shadow image 640, with rotation 45 degrees the shadow image 642 and with rotation of 90 degrees the shadow image 644. These images are included in the image library as being images to be ignored since they are different from the bacteria images that are sought.

Figure 29:
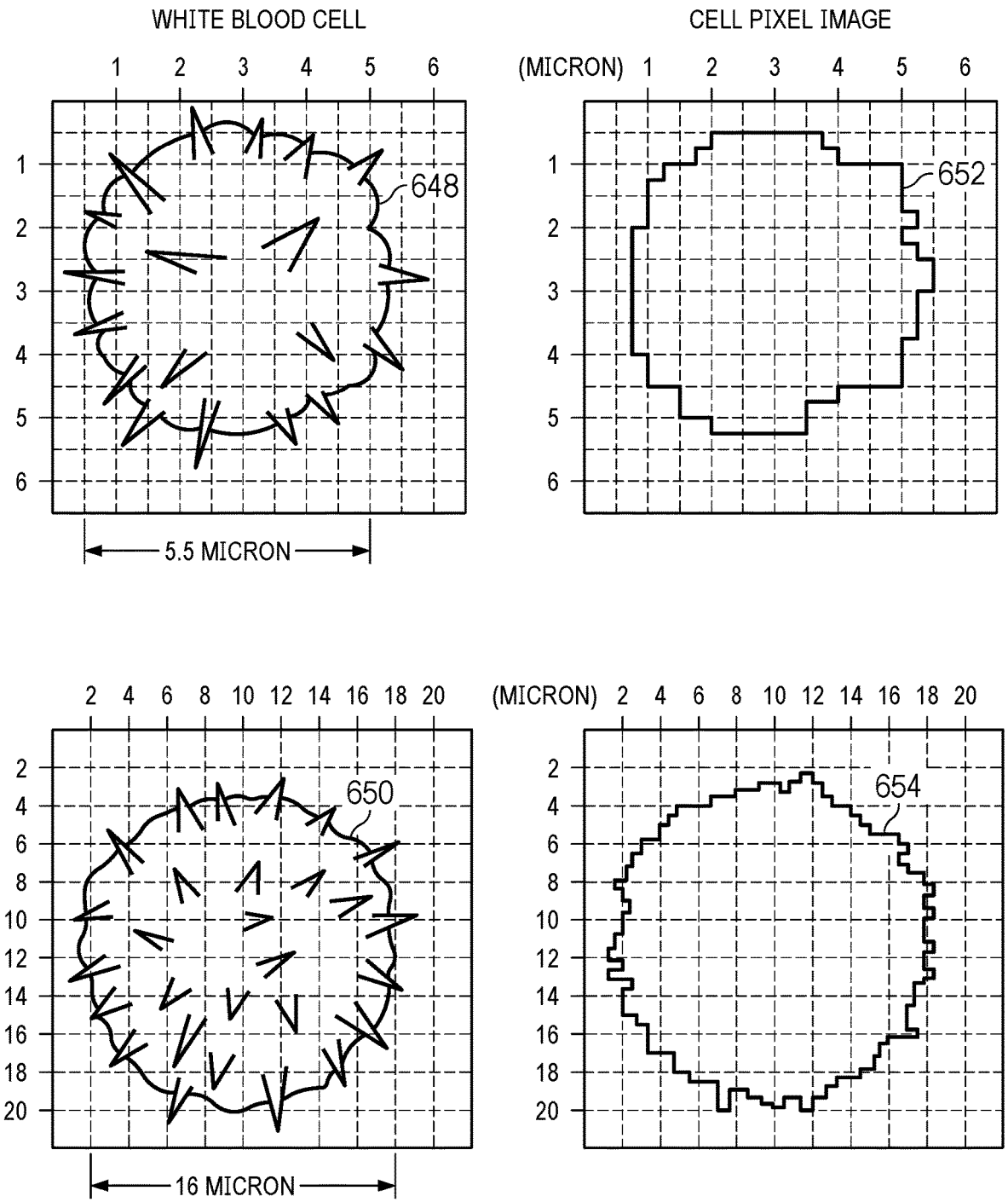
FIG. 29 is a set of white blood cell images for pattern recognition.

FIG. 29 shows a white blood cell 648 having a relatively large size and a white blood cell 650 having a smaller size. These cells are essentially spherical and therefore appear approximately the same at all rotation angles. Cell 642 can produce a shadow image 652 and cell 650 can produce a shadow image 654. Again, these images 652 and 654 can be included in the cell library as images to ignore.

Figure 30:
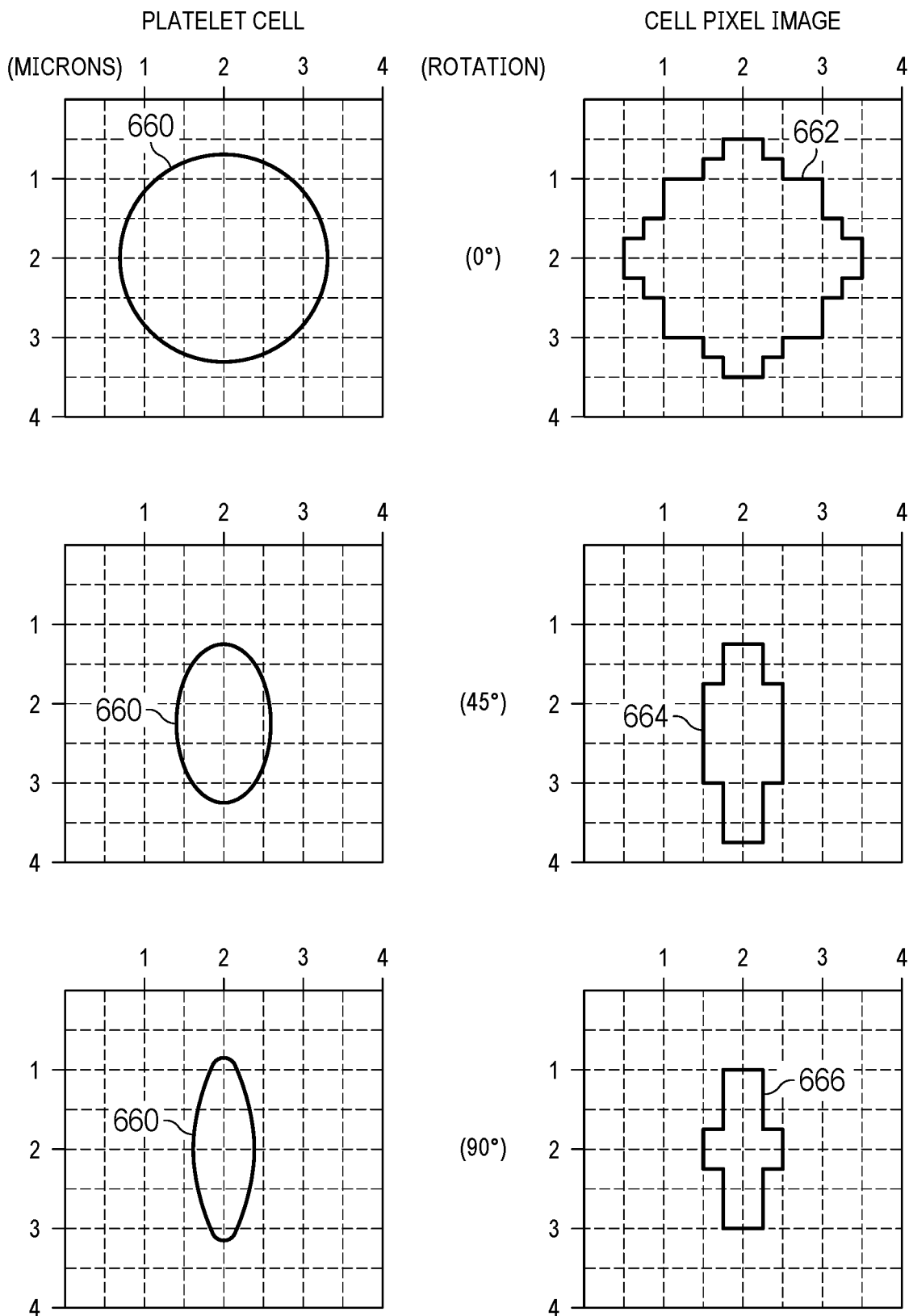
FIG. 30 is a set of platelet cell images for pattern recognition, FIGS. 31A, 31B and 31C describe a logic sequence flow of operations for a diagnostic process.

A blood platelet cell 660 is shown in FIG. 30. A platelet is a biconvex discoid (lens-shaped) structure, 2-3 micron in greatest diameter. This shape is thin at the edge and thickest in the center. At a rotation of 0 degrees, the cell 660 can produce a shadow image 662, at a rotation of 45 degrees a shadow image 664 and at 90 degrees, a shadow image 666. As with the other normal blood cells, these images are used as recognition of cells to ignore in the processing operation.

Each of the cells in FIGS. 27, 28 and 30 are shown, for illustration, at a limited number of rotation angles; but the library can contain images representing a finer degree of rotation, for example, every 5 degrees of rotation.

An objective of the present invention is to locate pathogen cells in blood. This is done by use of an image library which has images of possible pathogen cells. This library can be created from known configurations of pathogen cells, such as *E. coli*, or by conducting a diagnostic procedure for a particular individual patient and determining what images for pathogen cells are present in the blood of that individual. The library can also include images of non-pathogenic cells which can be ignored.

An operation that can be used in such image identification is herein termed a "diagnostic process". This can be performed to produce an image library to define the specific target images for a particular individual. In this process, samples of the patient's blood are scanned to determine what configuration of cells are present. The cell configurations that are likely pathogen cells are then specifically targeted in the processing operation. By performing this initial diagnostic process, the targeting of pathogen cells and destruction of those specific cells is customized for the blood of the one specific patient undergoing treatment.

An initial aspect of the diagnostic process is defining image filter parameters to eliminate cell images that are very unlikely to be pathogen cells, such as red and white blood cells. This can significantly reduce processing time. This filtering substantially reduces the volume of data that is produced in the diagnostic process and focuses on the images most likely to be pathogen cells. In addition, whether or not likely pathogen cells are identified, this information can assist in the medical assessment of the patient.

A example set of image filter parameters, for a system having a pixel size of 0.50-micron by 0.50-micron, are the following:
1. An image is defined as a set of at least 12 contiguous dark pixels entirely encompassed by light pixels, but not encompassing any light pixels.
2. The maximum number of dark pixels in an image is 60.
3. The maximum length of an image in any direction is 16 pixels.

Image pixel data, as a measured electrical quantity, typically includes noise, and in this application, much of the noise is either a single isolated dark pixel or a small group of contiguous dark pixels. This noise is substantially eliminated by the minimum dark pixel count limitation.

Figure 31B:
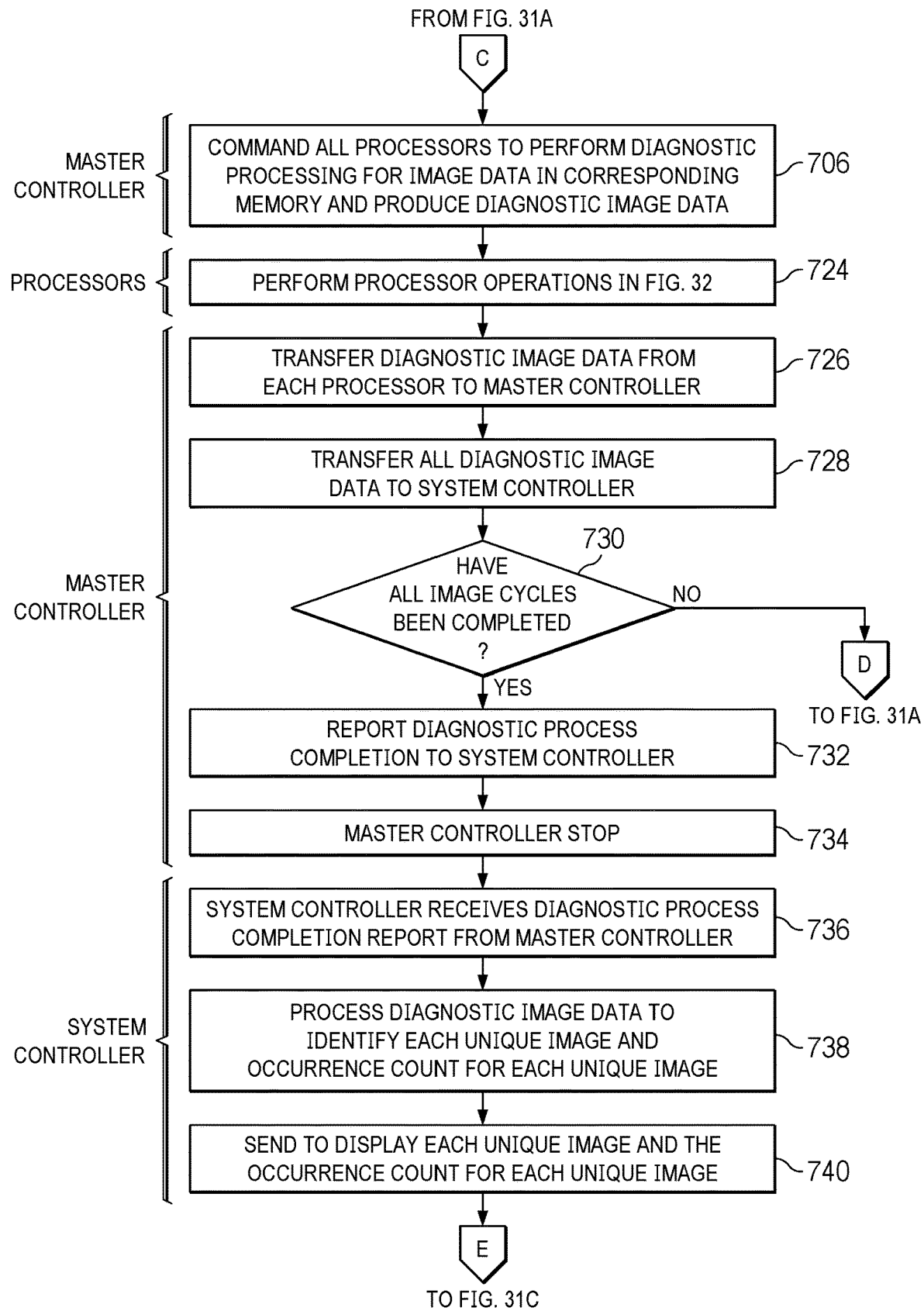
Figure 31C:
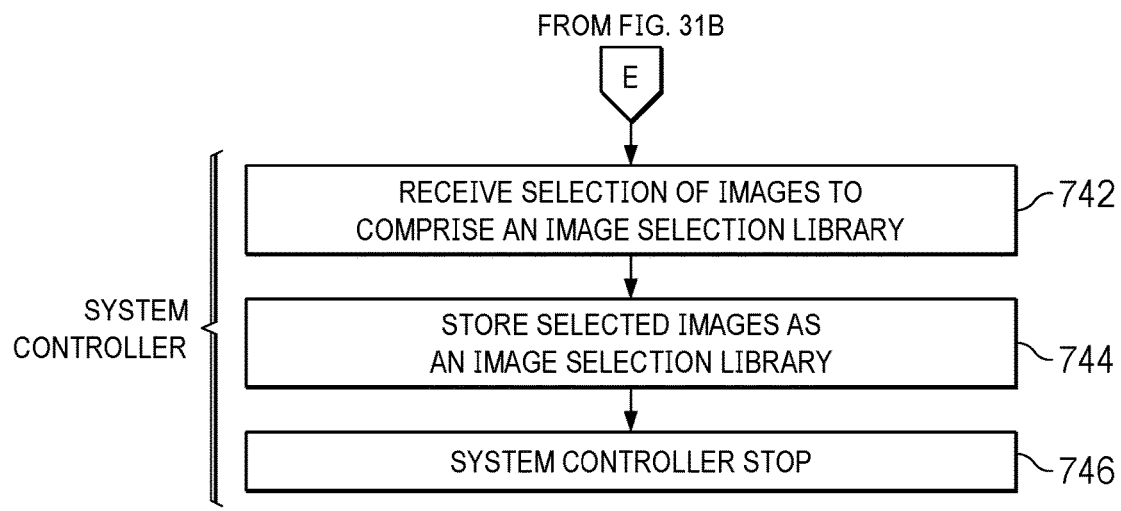
Figure 32:
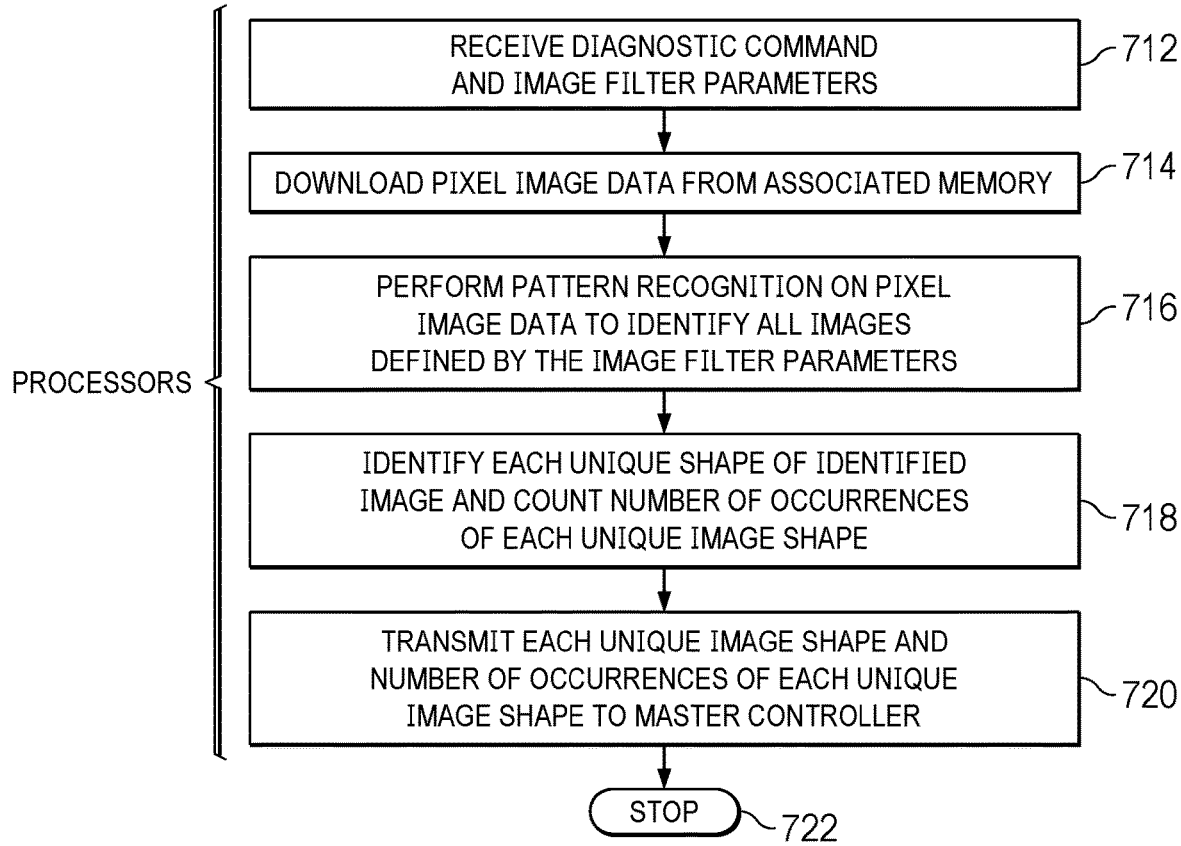
FIG. 32 is a logic sequence flow of a diagnostic process performed by processors to identity unique images in the pixel data.

The diagnostic process is further described in reference to FIGS. 31B, 31C and 32. The diagnostic process is initiated by the system controller 14 in step 680. Next, in step 682, the system controller 14 downloads the instruction to perform the diagnostic process to the master controller 434 (See FIG. 22) along with the number of image cycles to perform and a list of image filter parameters, as described above.

The master controller 434 receives the diagnostic start command and parameters in step 684. Next, in step 686, the master controller downloads the diagnostic process selection and the image filter parameters to all of the processors in the imager and processor unit 60. The master controller in step 688 next starts the pump 62 and runs it for sufficient time to fill all of the chambers of the cassette 58. The master controller 434 next resets all of the pixels in all of the sensor arrays in step 690. In step 692, the master controller waits for the chamber fill time to expire to ensure that the chambers are filled with blood and the blood is stationary.

After the chambers have been filled, the master controller 434 opens all of the shutters of the LCD array 56 in step 694. Next, in step 696, the master controller activates all of the sensor arrays 480-538 (FIG. 23) to be ready to measure incident light. The light generator 54 is next activated, for a predetermined time, to produce visible light in step 698. After the light has terminated, all of the sensor arrays are deactivated so the pixels are no longer receiving light in step 700. The master controller closes all of the LCD shutters in step 702. Next, in step 704, the master controller 434 commands all of the sensor arrays to download the collected pixel data to the corresponding memories. After the pixel data has been moved to the memories, in step 706, the master controller directs all of the processors to perform the processor diagnostic operation and thereby produce diagnostic image data, The operation of each processor to produce the diagnostic image data is described in reference to FIG. 32. In step 712, each processor receives the diagnostic command and the image filter parameters, see step 686 in FIG. 31. Next, in step 714, the processor downloads the diagnostic image data from the corresponding memory. After the diagnostic image data has been received, the processor performs pattern recognition on this data, identifies images, and applies the image filter parameters to eliminate many of the detected images. In step 718, the processor identifies each unique image and counts the number of occurrences of each unique image. In step 720, the unique image shapes and number of occurrences for each image shape are transmitted to the master controller upon request. After this data transfer, the processor operation is complete for this cycle and the processor operation stops at step 722.

Returning to FIG. 31B, the processor operations described in FIG. 32 have been completed at step 724. At step 726, the master controller requests that each processor transfer the diagnostic image data to the master controller. At step 728, the master controller 434 transfers all of the diagnostic image data received from all of the processors to the system controller 14. At question step 730, it is determined by the master controller if all image cycles have been completed. If "NO", the operation returns to step 688 to complete another cycle. If "YES", control goes to step 732 where the master controller 434 reports completion of the diagnostic process to the system controller 14, and then proceeds to the stop at step 734.

Referring to FIG. 31B, at step 736, the system controller 14 receives all of the diagnostic image data from all of the processors. All of this data is examined to find each unique image and the number of occurrences of each unique image. This is performed in step 738, it is likely that many of the same unique images will be received from most, if not all, of the processors. Next, the system controller sends to a display screen a display of each unique image and the number of occurrences of that image, as set forth in step 740. The number of displayed images can be reduced by eliminating those with a low number of occurrences, for example, a cut off at less than 1,000 occurrences.

Figure 33:
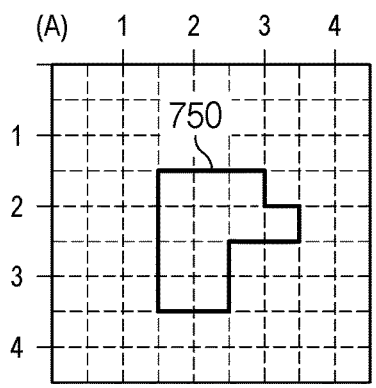
FIG. 33 is a set of diagnostic image patterns produced in the diagnostic process described in reference to FIG. 32.
Figure 33:
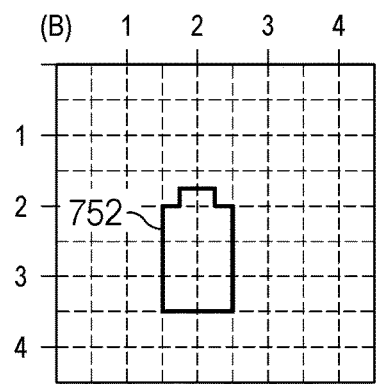
Figure 33:
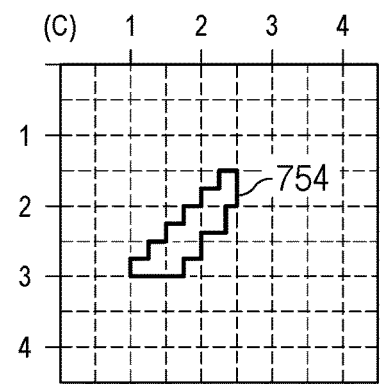
Figure 33:
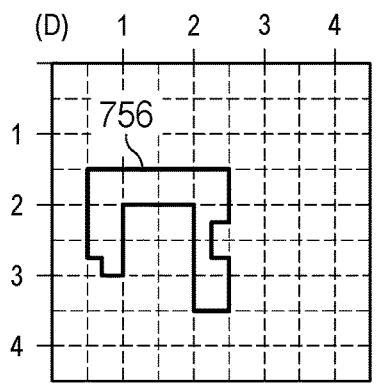
Figure 33:
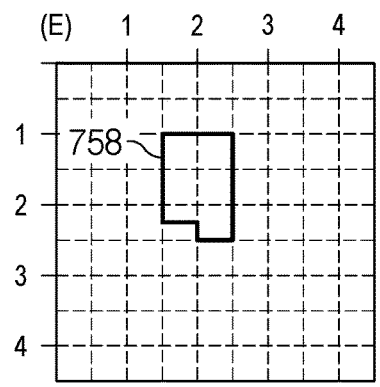
Figure 33:
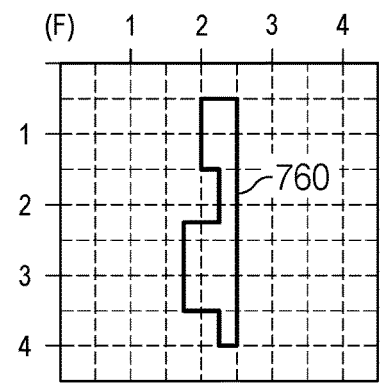
Figure 33:
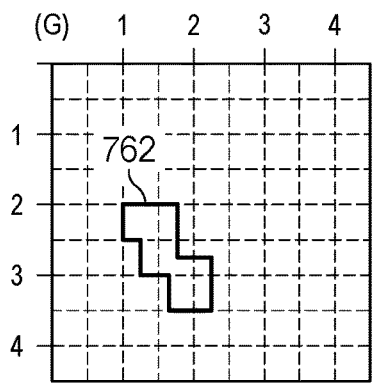
Figure 33:
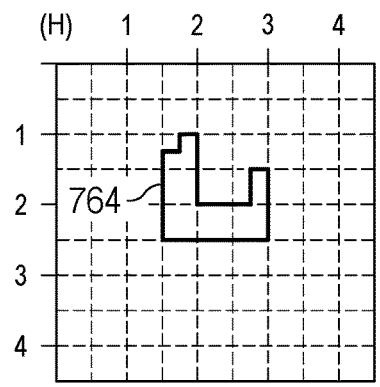
Figure 33:
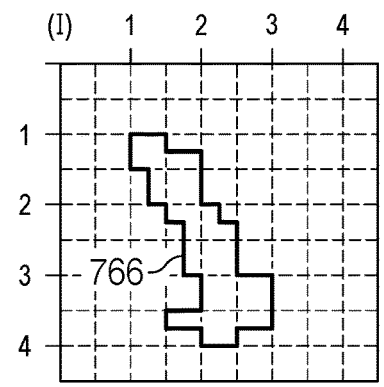
Figure 34:
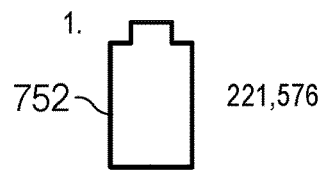
FIG. 34 is a screen display of image data and counts from the diagnostic process described in FIGS. 31A, 31B, 31C, 32, and 33, FIGS. 35A and 35B are a logic flow diagram for operation of a disclosed apparatus to identify and neutralize pathogen cells.
Figure 34:
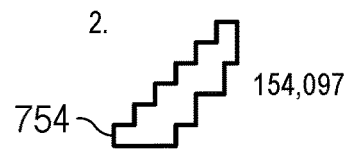
Figure 34:
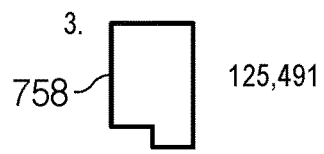
Figure 34:
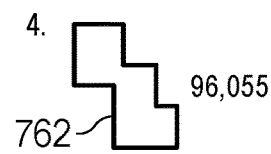
Figure 34:
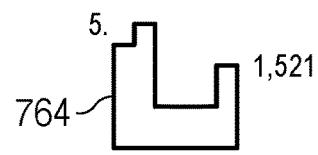
Figure 34:
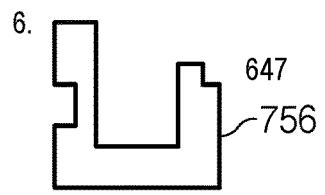
Figure 34:
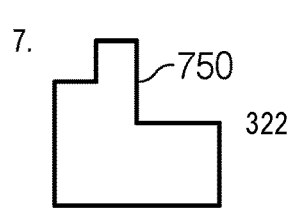
Figure 34:
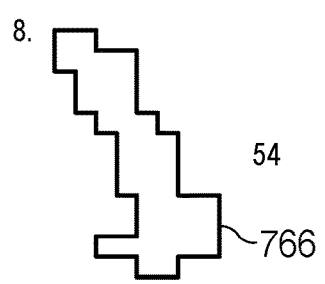
Figure 34:
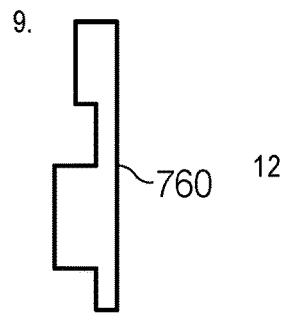

FIG. 33 is a display of nine samples of images that could have been produced in the diagnostic process, a compete display could have dozens or hundreds of images. This display has images 750, 752, 754, 756, 758, 760, 762, 764, and 766. See FIG. 34 for a sample display of these images with the corresponding occurrence counts. Although all of these images meet the filter parameters, an examination of these sample images indicates that some may represent *E. coli* pathogen cells (see FIG. 27), such as, for example images 752, 754 and 758 and others are less likely to be *E. coli* pathogen cells, such as, for example, images 756 and 764. A trained operator, or trained software such as a neural network or artificial intelligence, can study the produced diagnostic cell images and determine which are likely to be pathogen cells. This identification of candidate images is received by the system controller 14 in step 742 (FIG. 31C). This selection of images is stored as a pathogen image library at step 744 and associated with the particular individual whose blood was analyzed. The system controller 14 completes its operations at step 746.

Figure 35B:
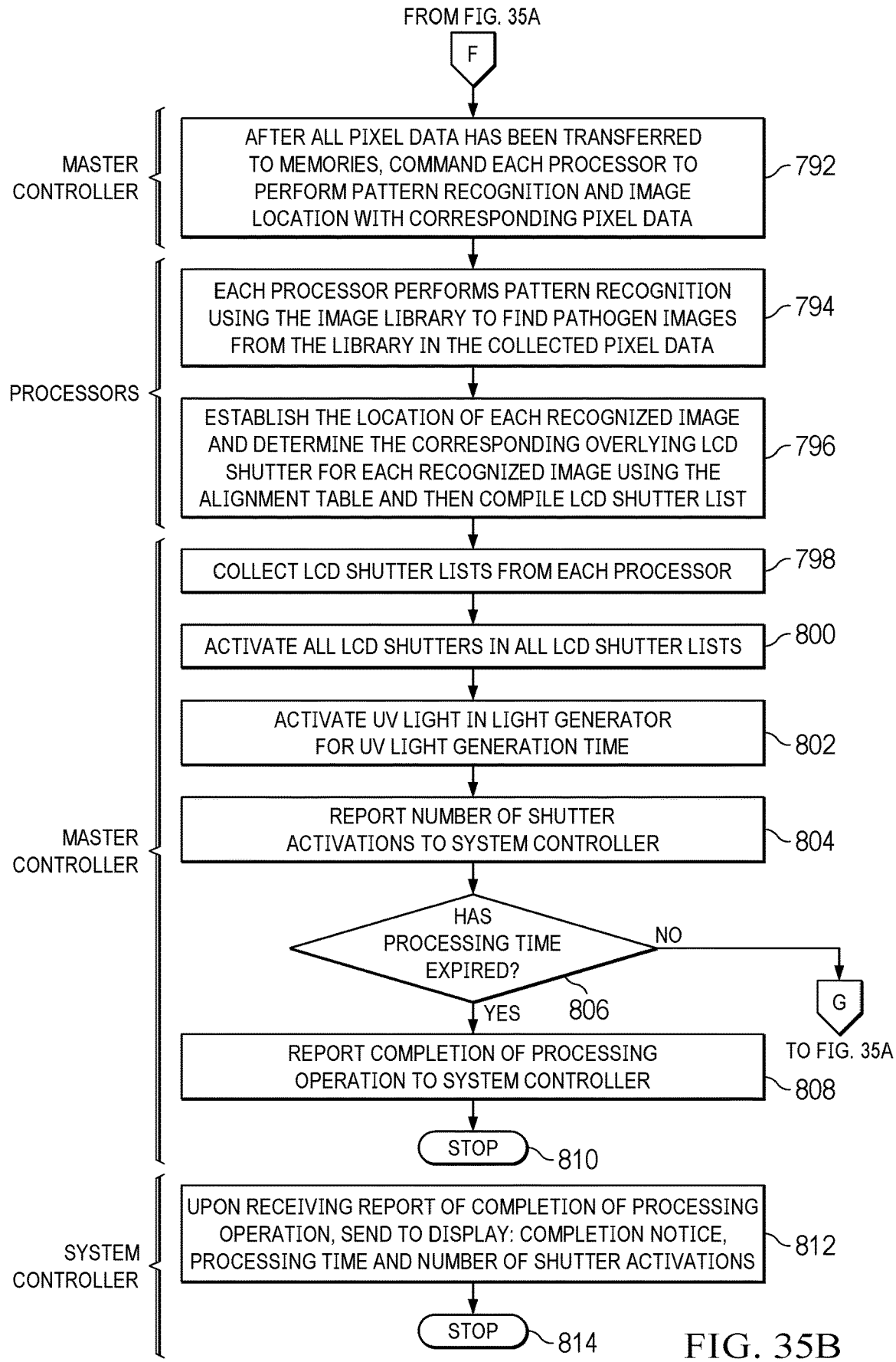
Figure 36:
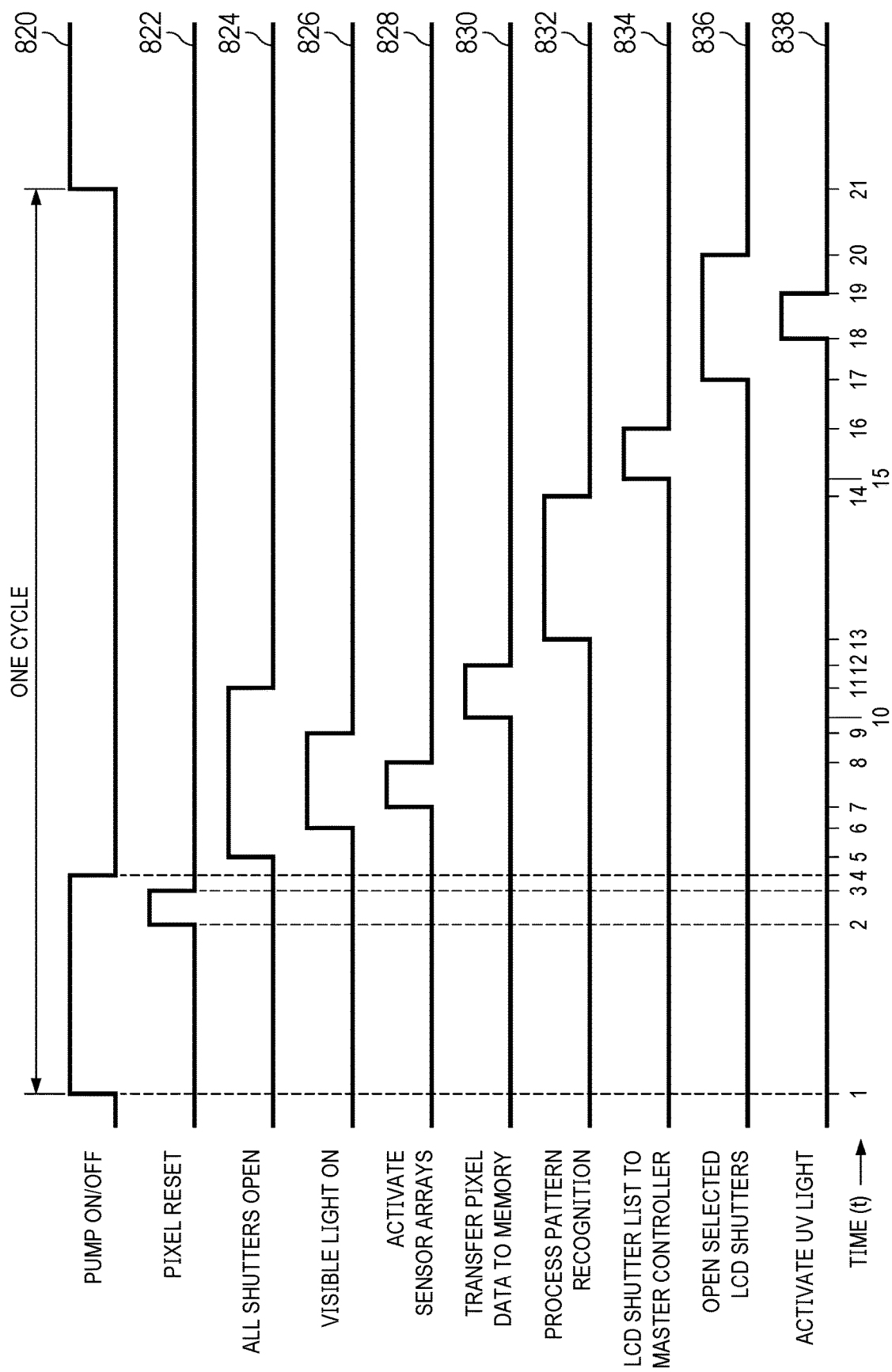
FIG. 36 is a timing diagram for the processing operation shown in the logic steps in FIGS. 35A and 35B.

A processing operation to locate and neutralize pathogen cells in blood is now described in reference to the logic flow steps shown in FIGS. 35A and 35B and the timing diagram shown in FIG. 36. This processing operation utilizes the cassette 58 configuration as shown in FIG. 15 with the system configuration shown in FIGS. 1, 3 and 22. Each processing operation requires a set of processing parameters. These processing parameters, with sample values, are as follows:

1. Processing time—8 hours
2. Pump speed—60% of maximum
3. Pump run time—4 sec
4. Visible light generation time—800 ins
5. Pixel light collection time—400 ins
6. UV light generation time—200 ins
7. Alignment data for each sensor array
8. Image library of pathogen cells and normal blood cells The action of starting a processing operation begins with a start command issued by the system controller 14 in step 770 (FIG. 35A). The system controller downloads to the master controller 434 in step 772 a command to start the processing operation and the processing parameters listed immediately above.

The master controller 434 receives the processing parameters and a command to start the processing operation in step 774. Next, the master controller, in step 776, downloads the image library to each of the processors (FIGS. 22 and 24). The alignment data for each sensor array is downloaded to each corresponding processor in step 778. In step 780 the master controller 434 starts the pump 62 to run for the pump run time from times $t_1$ to $t_4$ in FIG. 36. Also, see waveform 820 in FIG. 36 wherein the pump is on when the waveform is high, from $t_1$ to $t_4$ in FIG. 36. Next, the master controller resets all of the pixels in all of the sensor arrays in step 782 and as shown in waveform 822. The pump run time expires when step 782 has been completed and blood fills the chambers 184-242 which are shown in FIG. 10. When the pump 62 stops, the blood is stationary in the chambers. Next, the master controller 434 opens all of the LCD shutters of the LCD array 56 in step 784 and waveform 824.

After the shutters are opened, the master controller 434, in step 786, activates light source 54 to produce visible light for the specified visible light generation time. See also waveform 826 in FIG. 36. The visible light is generated while the shutters are open. While collimated light is being produced by the light source 54, in step 788, and as shown in waveform 828, the master controller 434 activates all of the pixels in all of sensor arrays 480-538 (FIG. 23). The pixels collect light for the light collection time. Then, all of the pixels are deactivated, as shown in waveform 828. After the pixel light collection is completed, the light source 54 is turned off and the LCD shutters are closed, as shown in waveforms 824 and 826. For source 54 high is on and low is off.

After the sensor arrays have collected light, the arrays contain pixel data. This pixel data is transferred, by a command from the master controller 434, to each corresponding memory in step 790 and shown in waveform 830. In step 792 of FIG. 35B, the master controller 434 sends a command to each processor to perform pattern recognition for the data in the corresponding memory. The time of this processor pattern recognition operation is shown in waveform 832 in FIG. 36.

After step 792, the processors perform pathogen cell image pattern recognition, step 794, for the pixel data based on the downloaded pathogen image library. In step 796, each processor determines, by using its alignment table, the identity of the LCD shutter that overlies the location of each identified pathogen cell image. Each processor builds in step 796 a list of these LCD shutters. In step 798, and as shown in waveform 834, the master controller collects the LCD shutter lists from all of the processors. In step 800, the master controller 434 activates (opens) each of the LCD shutters in the LCD shutter lists provided by the processors. This step is shown in waveform 836 in FIG. 36. Next, in step 802, the master controller 434 activates the light generator 54 to produce UV light for the specified generation time. This UV light generation is shown in waveform 838 in FIG. 36. After the UV light generation has been completed, the LCD shutters are closed as shown in waveform 836.

The above actions have identified and located likely pathogenic cells in the blood sample in the holding chambers, and then exposed the individual identified cells to sufficiently energetic UV light in a small area of 16 square microns each to destroy (neutralize) a substantial percentage of the identified pathogenic cells. When this is completed, the processed blood is moved out of the holding chambers and replaced with new blood which is then processed as described in the next cycle.

After the LCD shutters have been closed, the master controller sends a report, step 804, of how many shutters were opened, which essentially compares to the number of pathogen cells likely detected and subject to UV light, to the system controller 14. This data is collected to determine the effectiveness of the processing operation.

In question step 806, a test is done to determine if the overall processing time, as set forth in the processing parameters, has elapsed. If the answer is "NO", control is returned to step 780 (FIG. 35A) to repeat the processing operation. If the answer is "YES", a termination report is sent from the master controller 434 to the system controller 14 and the master controller stops operation at step 810. An alternative termination to "Processing time" in a count of LCD shutter activations, which essentially corresponds to the number of identified and located pathogen cells. In the processing parameters the "Processing times" is replaced with "Processed Pathogen Cell Count" (PPCC). This is a processing count estimate of what could be an effective count for the individual patient undergoing treatment. Step 806 is changed to "Has Processing Count Been Reached?". If not, (NO exit in step 806) the process continues. If the count has been reached (YES exit from step 806) the process continues to the end step 814.

Upon completion of operations by the master controller 434, the system controller 14 receives a report of completion in step 812 in FIG. 30 and the system controller sends to a display screen a report of completion, the processing time or completed PPCC, and the number of shutter activations. This data can indicate the effectiveness of the overall processing operation. The system controller stops at step 814.

Figure 37:
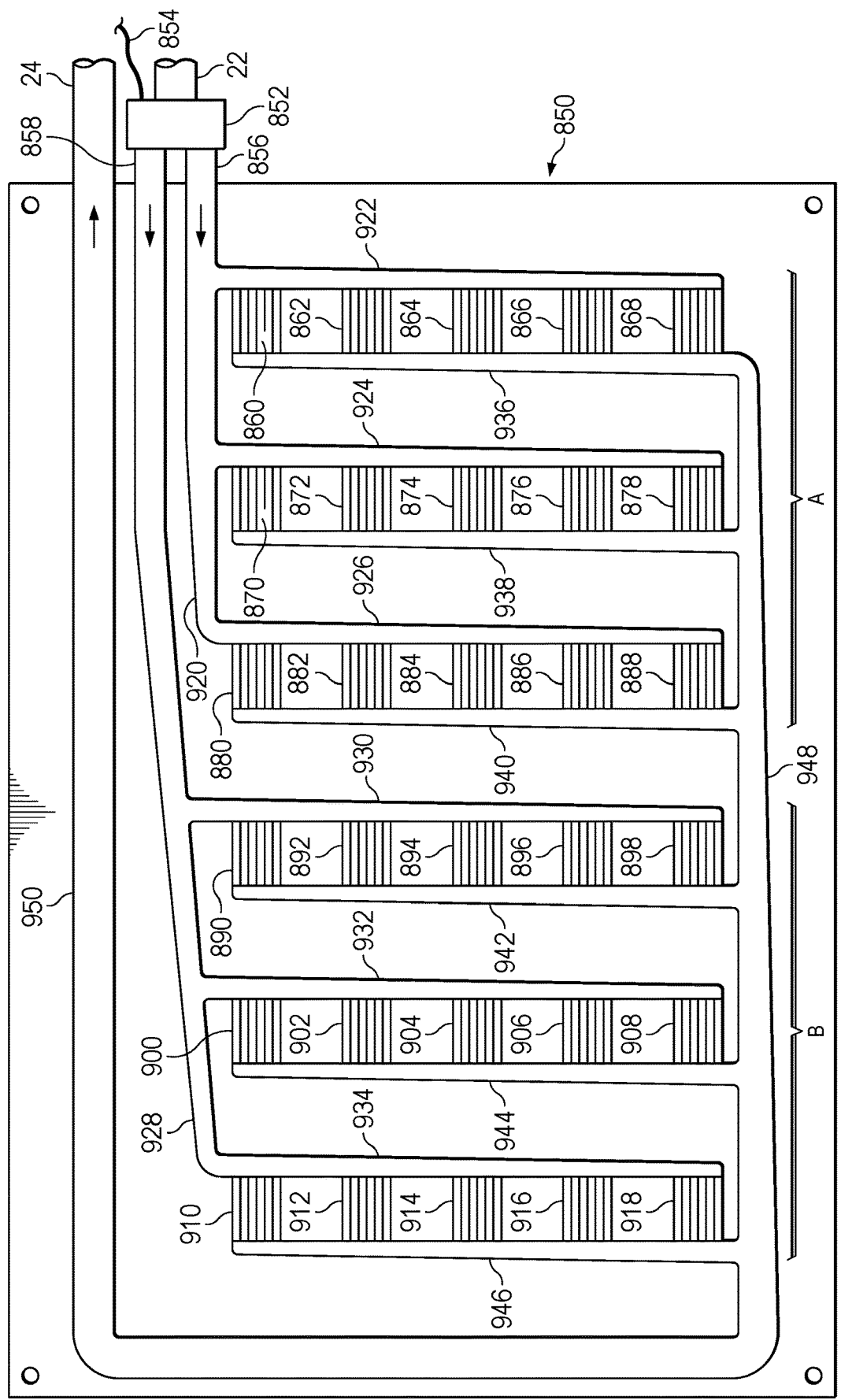
FIG. 37 is a top-down view of the top section of a second configuration of a cassette which has two arrays of holding chambers and a routing valve.
Figure 38A:
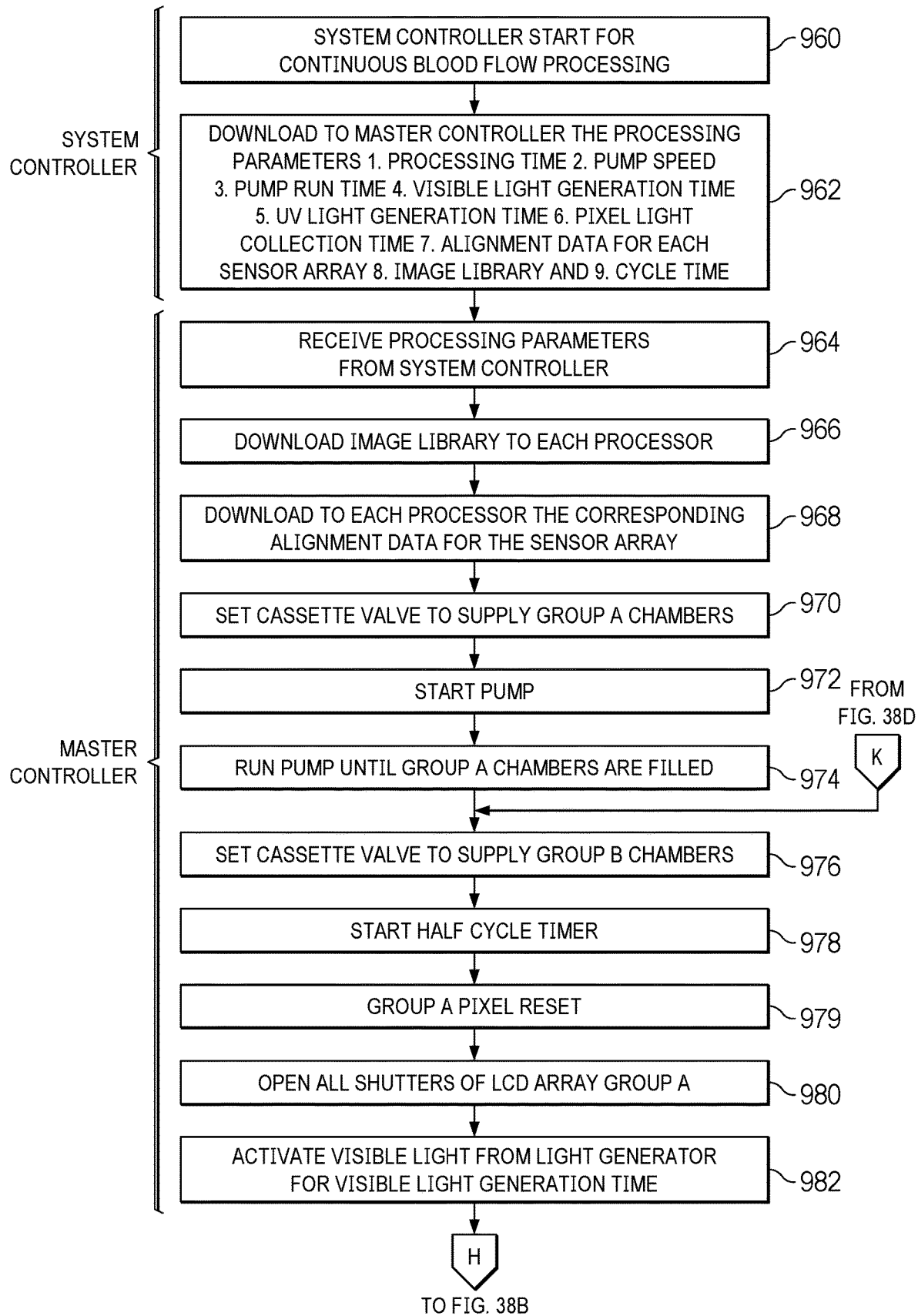
FIGS. 38A, 38B, 38C and 38D illustrate a logic flow diagram for operation of a disclosed apparatus having a cassette with two arrays of holding chambers and a routing valve as shown in FIG. 37 to provide for continuous blood flow operation
Figure 38B:
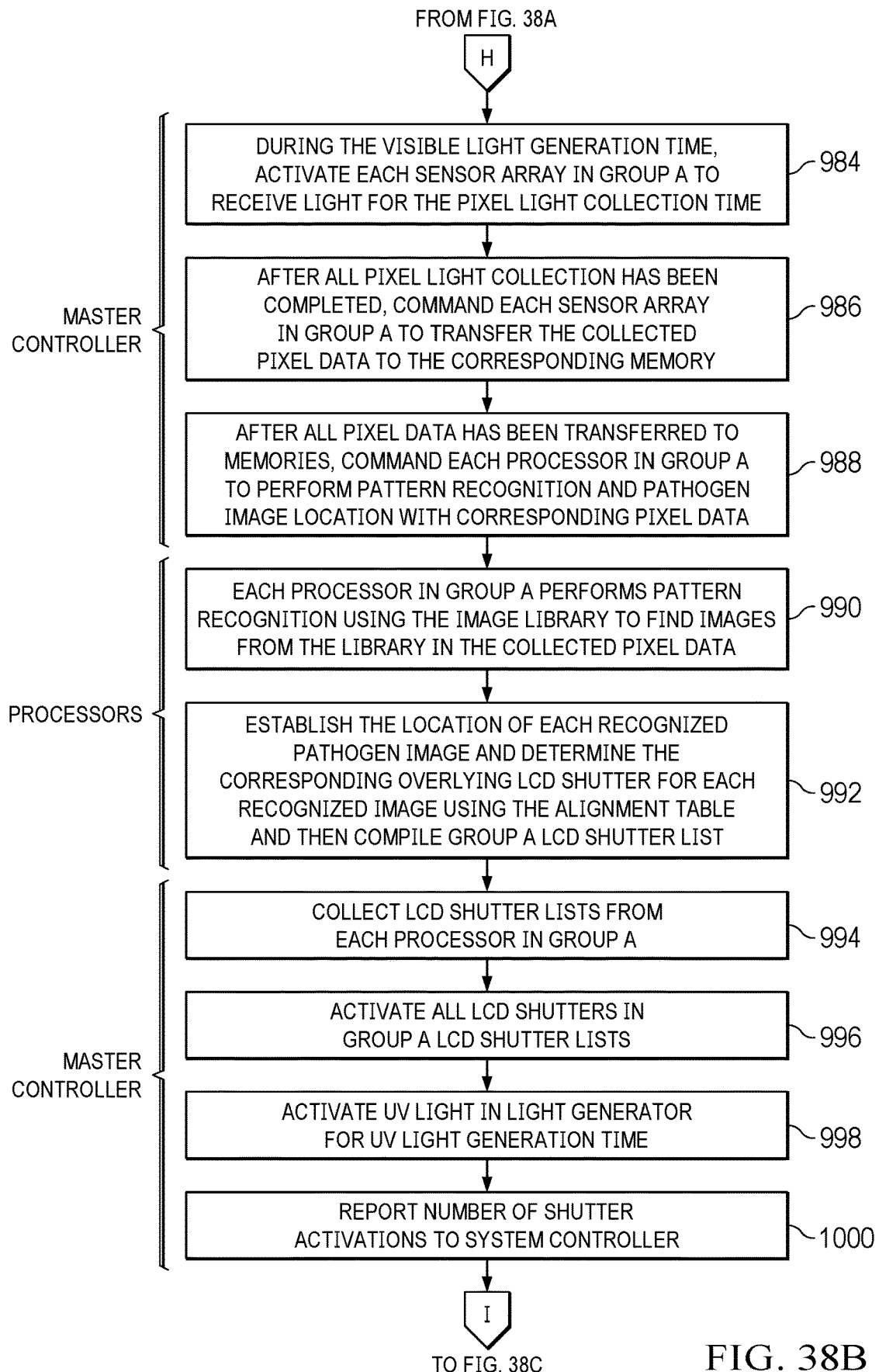
Figure 38C:
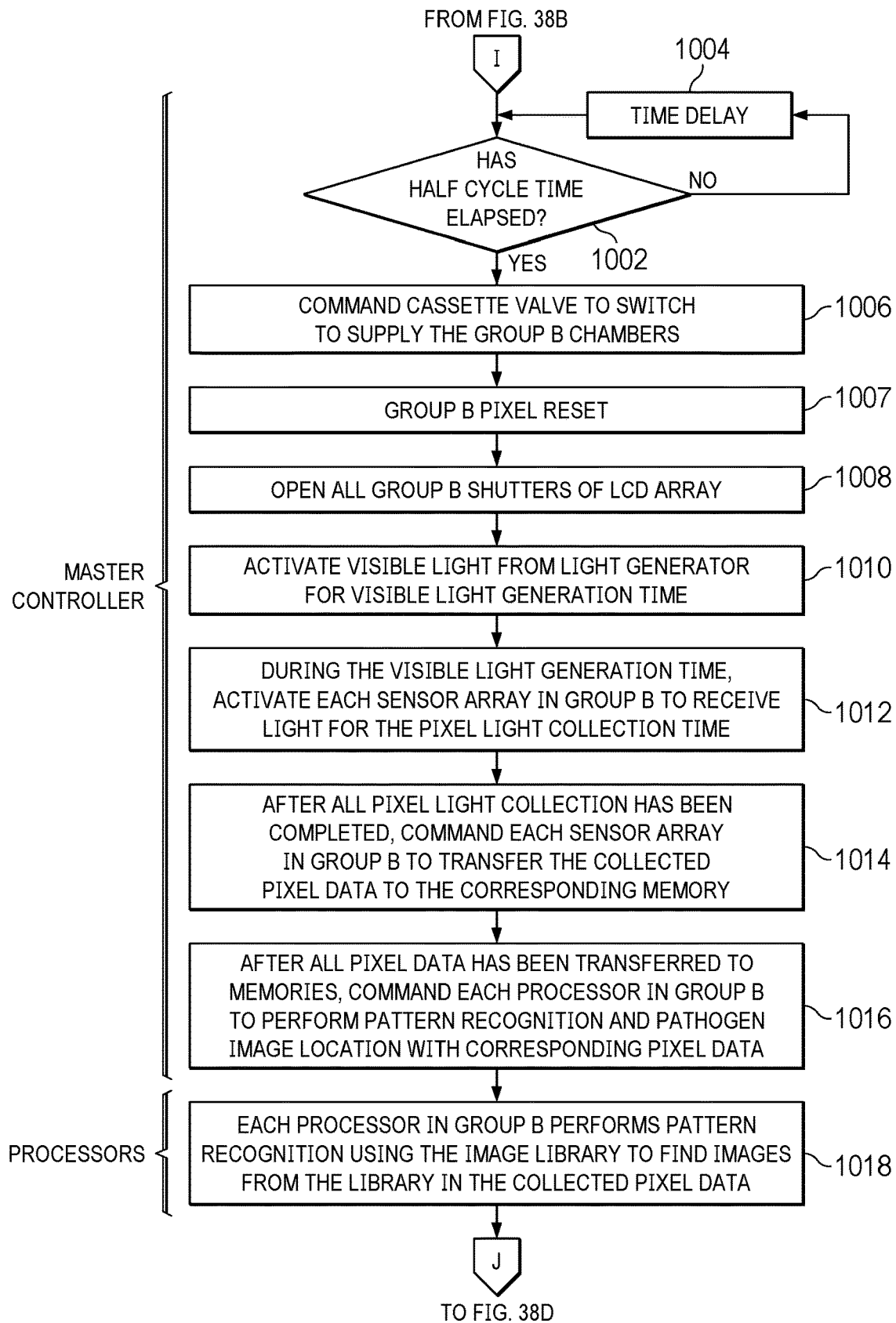
Figure 38D:
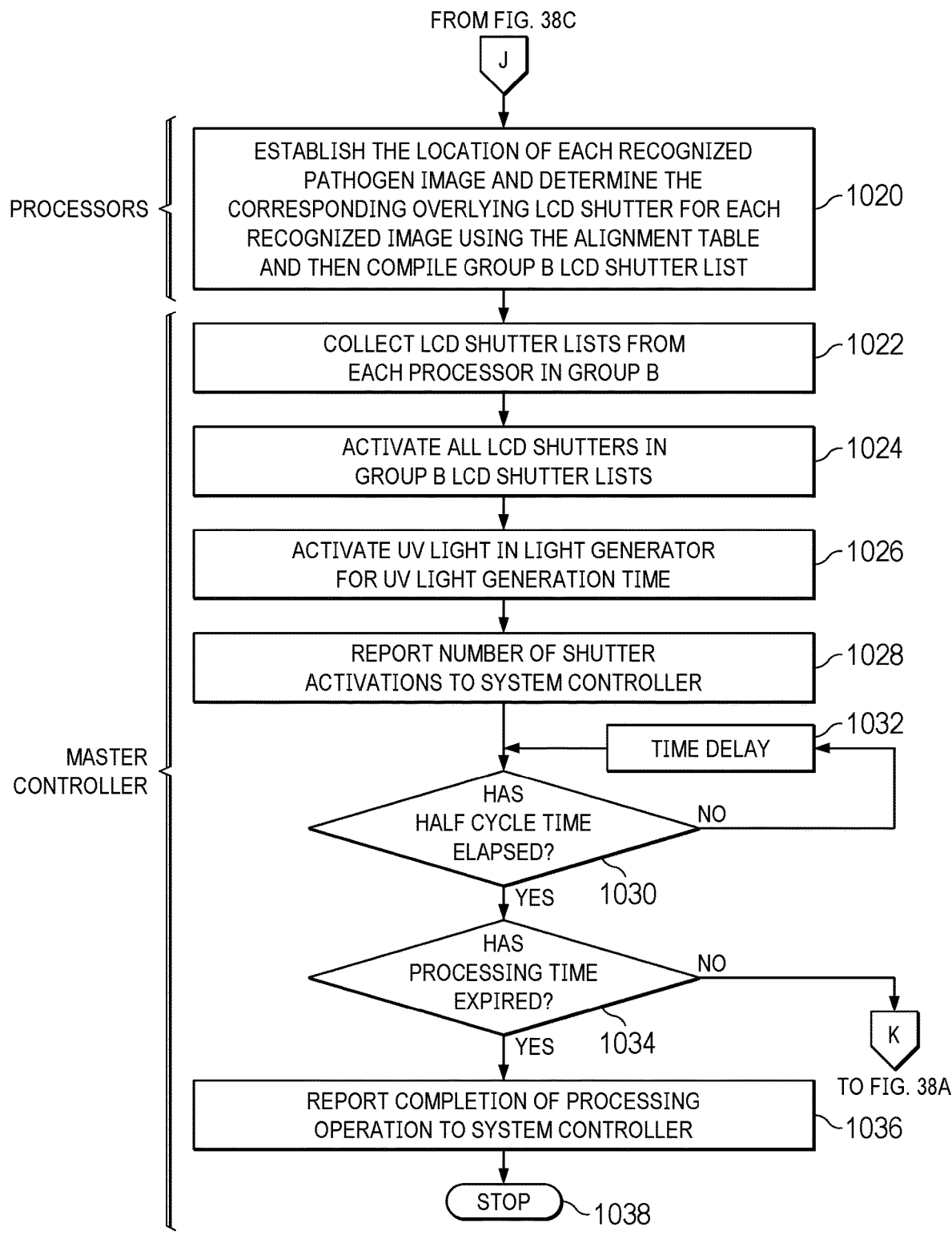

The processing operation described above in reference to FIGS. 35A, 35B and 36 starts the pump 62 to fill the holding chambers and stops to make the blood in the chambers stationary for examination and exposure to kill the identified pathogen cells. An alternative configuration and operation are described in reference to FIGS. 37, 38A, 38B, 38C, 38D, 39A and 39B. In this configuration, the pump 62 runs continuously and the blood flow is continuous. This configuration uses a second design for a cassette. A cassette 850 is shown in FIG. 37. This cassette has 30 chambers, the same number as in cassette 58 described above. However, in cassette 850 the 30 chambers are divided into groups A and B, which are filled and processed alternately so the blood flow can be continuous and one group can be processing while the other group is filling.

Referring to FIG. 37, the cassette 850 works with a valve 852 which is electrically controlled through a line 854 connected to the master controller 434. The valve 852 has its input connected to blood input line 22 and the valve has two output lines which are input lines 856 and 858 to the cassette 850. The valve 852 has two states which are selectively set by signals provided through the line 854. In one state the input line 22 provides blood to cassette input line 856, but not to line 858, and in the second state, the valve 852 routes blood from input line 22 to the cassette 850 input line 858, but not to input line 856.

The cassette 850 has 30 holding chambers, each chamber having the same size and configuration for the chambers described above for cassette 58. The cassette 850 has a first set of holding chambers 860, 862, 864, 866, 868, 870, 872, 874, 876, 878, 880, 882, 884, 886, and 888. These are termed the group A holding chambers. The cassette 850 further has a second set of holding chambers 890, 892, 894, 896, 898, 900, 902, 904, 906, 908, 910, 912, 914, 916, and 918. These are termed the group B holding chambers.

Further referring to FIG. 37, input line 856 supplies the flow of blood to a distribution line 920 which in turn supplies blood to input lines 922, 924, and 926. Input line 922 supplies blood to chambers 860, 862, 864, 866 and 868. Input line 924 supplies blood to chambers 870, 872, 874, 876, and 878. Input line 926 supplies blood to chambers 880, 882, 884, 886, and 888. Input line 858 supplies blood to distribution line 928 which in turn provides blood to input lines 930, 932, and 934. Input line 930 provides blood to the holding chambers 890, 892, 894, 896 and 898. Input line 932 provides blood to the holding chambers 900, 902, 904, 906 and 908. Input line 934 provides blood to the holding chambers 910, 912, 914, 916 and 918.

Output line 936 receives blood leaving the chambers 860, 862, 864, 866 and 868 and supplies this blood to collection line 948. Output line 938 receives blood leaving the chambers 870, 872, 874, 876, and 878 and supplies this blood to collection line 948. Output line 940 receives blood leaving the chambers 880, 882, 884, 886, and 888 and supplies this blood to the collection line 948. Output line 942 receives blood leaving the chambers 890, 892, 894, 896 and 898 and supplies this blood to the collection line 948. Output line 944 receives blood leaving the chambers 900, 902, 904, 906 and 908 and supplies this blood to the collection line 948. Output line 946 receives blood leaving the chambers 910, 912, 914, 916 and 918 and supplies this blood to the collection line 948.

In the cassette 850, the collection line 948 is connected to a return line 950 which is in turn connected to the blood return line 24. The blood supplied by the pump 62 through line 22 is alternately routed by the valve 852 to either the group A holding chambers or to the group B holding chambers. By switching the valve between its two positions, the cassette 850 is provided with a continuous flow of blood.

The lines 920, 922, 924 and 926 comprise an input manifold for the group A holding chambers of cassette 850. The lines 928, 930, 932 and 934 comprise the input manifold for the group B holding chambers of cassette 850. The lines 936, 938, 940, 942, 944, 946, 948 and 950 comprise the output manifold for cassette 850.

The processing operation using the cassette 850 (FIG. 37) is described in reference to the logic flow in FIGS. 38A, 38B, 38C, 38D and the timing diagram in FIG. 39. This processing operation uses the following processing parameters:

These processing parameters, with sample values, are as follows:
 1. Processing time—8 hours
 2. Pump speed—60% of maximum
 3. Visible light generation time—800 ins
 4. Pixel light collection time—400 ins
 5. UV light generation time—200 ins
 6. Alignment data for each sensor array
 7. Image library of pathogen cells and normal blood cells
 8. Cycle time—8 sec These parameters differ somewhat from those used with the processing operation described in FIG. 30. There is no pump run time because the pump runs continuously. There is a cycle time which is the time for filling and processing all of the chambers in groups A and B of cassette 850. This processing operation has processing overlapping with filling. While the blood in one group of chambers is being processed, the chambers in the other group are being filled. Optionally, the Processing time can be replaced with a Processed Pathogen Cell Count (PPCC) value, as described above.

Referring to FIGS. 37, 38A, 38B, 38C, 38D and 39, the operation starts at step 960 with a command from the system controller to start the continuous flow blood processing operation. In the next step, 962, the command to start the processing and the processing parameters, as listed above, are downloaded to the master controller 434.

The master controller 434, at step 964 receives the command to start and the processing parameters. At step 966, the image library is downloaded to each of the processors. The alignment data for each sensor array is sent to each of the corresponding processors in step 968 by the master controller 434. The master controller then sets valve 852 for supplying blood to the group A chambers in step 970. At step 972 the master controller starts the pump 62. The pump 62 runs until the group A chambers are filled in step 974.

At step 976, the master controller changes the cassette valve 852 to begin filling the group B chambers of the cassette 850. Step 976 is the start of the repetitive processing cycle. The master controller starts a half cycle timer in step 978. This is a time that is one half of the cycle time in the processing parameters. The group A chambers and group B chambers blood flow is shown in waveforms 1050 and 1052 in FIG. 39A. The high level is blood flow, the low level is no blood flow. Note that there is overall continuous blood flow.

The master controller 434 resets all of the pixels in the group A sensor arrays in step 979 and waveform 1054. At step 980, the master controller opens all of the LCD shutters for group A, see also waveform 1056 in FIG. 39A. At step 982, the master controller activates the light source 54 to generate visible light for the specified time, step 984. See waveform 1058 in FIG. 39A. The pixels in the group A sensor arrays are activated, step 984, for the specified time to collect light that has passed through the group A chambers of the cassette 850. This timing is shown in waveform 1060 in FIG. 39A. After the pixel light collection has ended, the master controller 434, in step 986, commands the group A sensor arrays to transfer the collected pixel data to the corresponding memory. See waveform 1062 in FIG. 39A.

After the pixel data has been transferred to the corresponding memories, the master controller 434, in step 988, commands each of the group A processors to perform pattern recognition and image location with the pixel data. The timing of this step is shown in waveform 1064 in FIG. 39A.

In step 990 each of the processors in group A performs pattern recognition with the pixel data using the images in the downloaded image library. In step 992, the processors identify and locate pathogen images in the pixel data and determine the location in the sensor array, and with the alignment table, determines for each location the corresponding LCD shutter and prepares an LCD shutter list.

The master controller, in step 994, collects the LCD shutter lists from all of the processors in group A. See timing waveform 1066 in FIG. 39A. Next, in step 996, the master controller 434 activates (opens) all of the shutters of the LCD shutter array 56 that are in the lists received from the processors, see waveform 1068 in FIG. 39B. These shutters correspond the locations of located pathogen cells in the cassette 850 holding chambers in group A. In step 998, the master controller activates the light source 54 to produce UV light for the specified UV light generation time. See waveform 1084 in FIG. 39B at time $t_{14}$ to $t_{15}$. After termination of the UV light generation, the master controller records and reports to the system controller 14 in step 1000 the number of shutter activations, which corresponds to the number of identified pathogen cells in the group A chambers of the cassette 850.

Question step 1002 (FIG. 38C) determines if the half cycle time has expired. This is the time required to fill the other group of chambers. If not, there is a time delay, step 1004, such as, for example, 100 milliseconds. This is repeated until the half cycle time has expired and the other group of chambers has been filled. This is exit "YES". When the half cycle time has expired, in step 1006, the master controller 434 commands the valve 852 to switch the blood flow to the group A chambers of cassette 850. See waveform 1052 in FIG. 39A. After this switchover is performed, the master controller 434 resets all of the pixels in the group B sensor arrays in step 1007. See also waveform 1070 in FIG. 39B.

The following processing steps repeat, for the group B chambers and associated components, the same processing described above for the group A chambers.

Figure 39A:
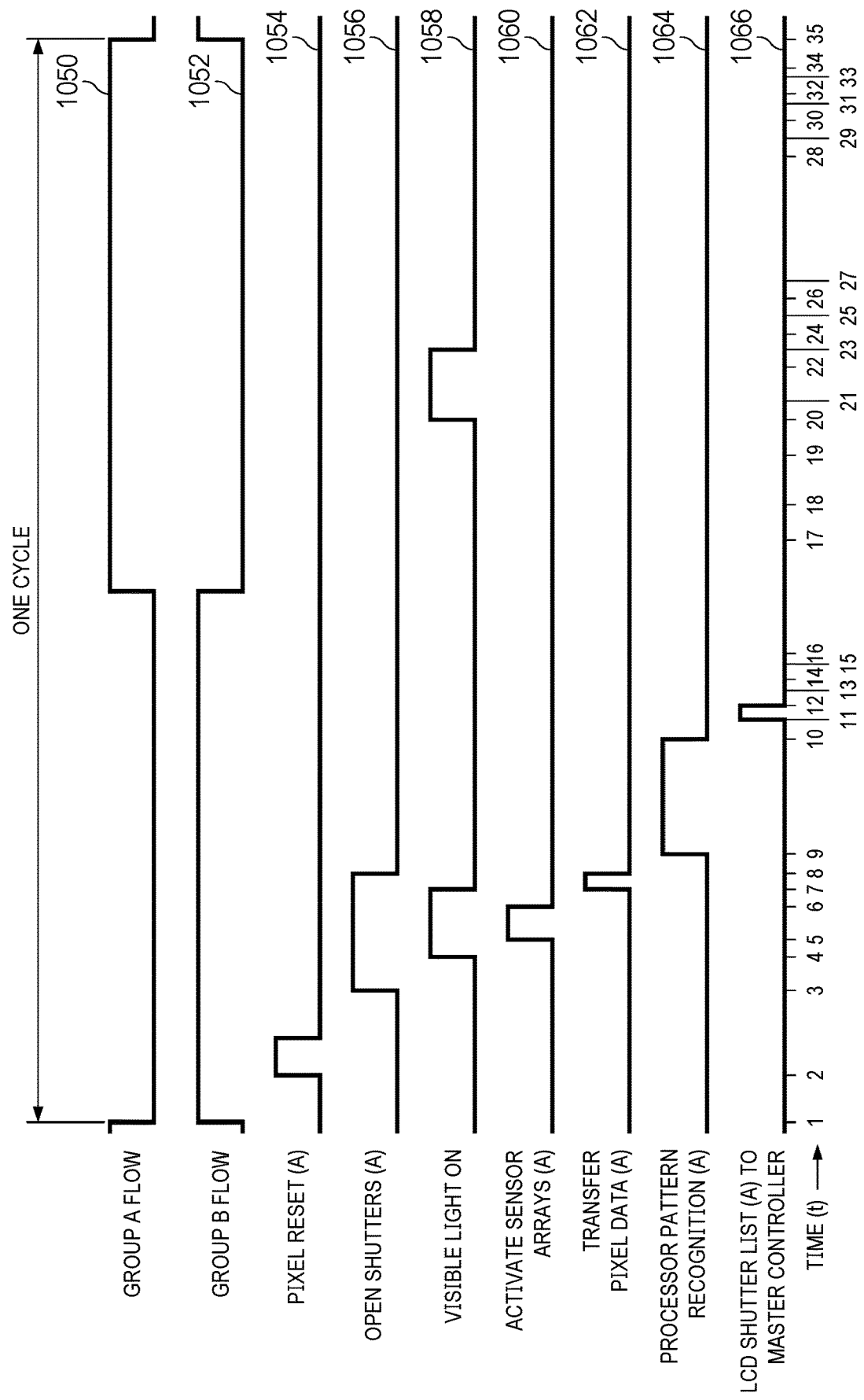
FIGS. 39A and 39B illustrate timing diagrams for the processing operation shown in the logic steps in FIGS. 38A, 38B, 38C and 38D.
Figure 39B:
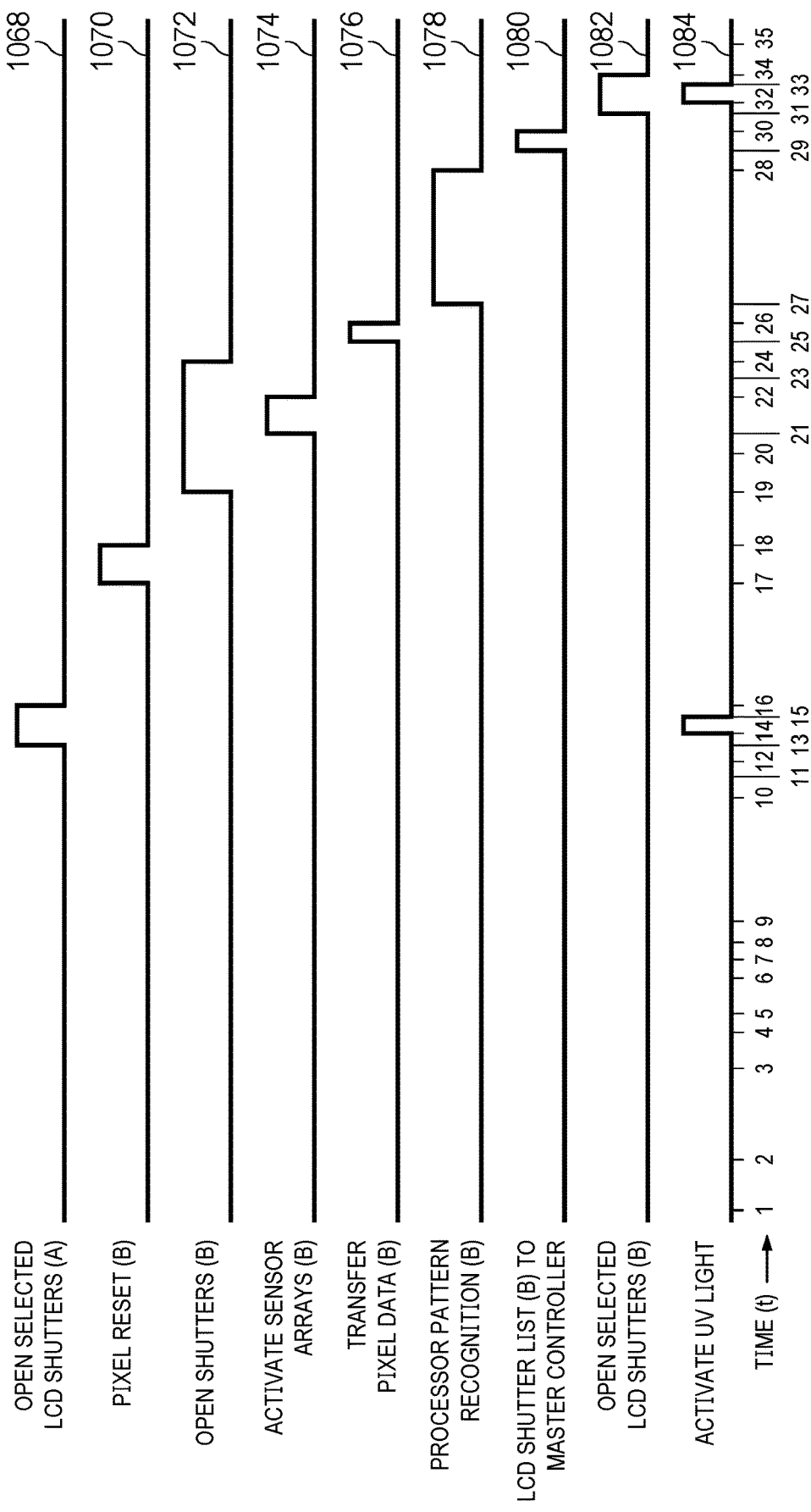

In step 1008, the master controller 434 opens all of the group B shutters of the LCD shutter array 56 and see waveform 1072 in FIG. 39B. At step 1010, the master controller activates the light source 54 to produce visible light for the specified time. See waveform 1058 in FIG. 39A. While the visible light is being produced, the master controller, in step 1012, activates all of the pixels in the group B sensor arrays for the specified time to collect light that has passed through the cassette 850 group B chambers and shadowed cells in the blood held in these chambers to produce shadow images in the light sensor arrays. See waveform 1074 in FIG. 39B. Next in sequence, in step 1014, the pixel data is transferred from the sensor arrays to the corresponding memories, also see waveform 1076 in FIG. 39B. In step 1016, the master controller commands the processors in group B to process the pixel data.

The processors in group B, in step 1018, perform pattern recognition as described above for the group A processors. See timing waveform 1078 in FIG. 39B. In step 1020, the processors identify and locate the pathogen images using the image library and produce a list of LCD shutters corresponding to the image locations.

In step 1022, the master controller 434 collects the LCD shutter lists from all of the group B processors. See waveform 1080 in FIG. 39B. In step 1024, the master controller 434 activates all of the listed shutters in the LCD shutter array 56. See waveform 1082 in FIG. 39B. Next, in step 1026, the master controller activates the light source 54 to produce UV light for the specified time. This UV light is directed into the cassette 850 group B holding chambers at the locations found for the identified pathogen cells, waveform 1084 in FIG. 39B. Next, the master controller reports the number of shutter activations to the system controller 14 in step 1028.

Question step 1030 determines if the half cycle time has elapsed. If "no", there is a time delay at step 1032 and this is repeated until the half cycle time has elapsed. See FIG. 38D. When the response is "YES", the question step 1034 determines if the overall processing time has expired. If the response is "NO", then control is returned to step 976 and another cycle is performed. If the response is "YES", the processing operation is finished and the master controller reports the completion to the system controller in step 1036 and operations terminate at the stop step 1038.

The processing described above can be continued, for multiple hours if required, to reduce the count of pathogen cells in the patient blood to a low enough level to assist the patient in recovering from the infection. Further, the embodiments described herein can be scaled to provide a desired blood throughput rate.

Alternatively, for step 1034, the master controller compares the total count of LCD shutter activations to the Process Pathogen Cell Count (PPCC). If the total count of shutter activations is less than the PPCC value, the "NO" exit is taken from step 1034. If the total count of shutter activations is more than the PPCC value, the "YES" exit is taken from step 1034.

After a treatment process has been completed with a patient, the cassette, such as 58 and 850, used in the treatment is preferably disposed of and a new cassette installed in the operational unit 10 (FIG. 1) for use with the next patient.

One embodiment described above has 30 chambers in a single cassette with a sensor, a chamber processor and memory for each chamber. However, embodiments can be implemented having different configurations which operate as described above. Further, the embodiments can be scaled by the number of chambers and/or flow rate through a chamber and/or data processing speed to provide a desired overall flow rate for blood processing. Non-limiting example embodiments are as follows:

1. 10 chambers each 2.0 cm×2.0 cm, each chamber having a corresponding light sensor with a single processor and memory serving all 10 chambers.
2. 10 chambers each 4.0 cm×4.0 cm, each chamber having a corresponding light sensor, processor and memory.
3. 30 chambers 2.0 cm×2.0 cm, each chamber having a corresponding light sensor, and a single processor and memory serving all 30 chambers.
4. 30 chambers divided into a separate 15 chamber Group A and 15 chamber Group B with a sensor for each chamber and a single processor and single memory for each group.
5. 40 chambers each 2.0 cm×2.0 cm and each chamber having a corresponding light sensor, and a processor and memory for each set of 10 chambers.
6. 100 chambers 2.0 cm×2.0 cm, each chamber having a corresponding light sensor, processor and memory.
7. 100 chambers 2.0 cm×2.0 cm, each chamber having a corresponding light sensor and having one memory and one processor for each 10 chambers.

Although several embodiments of the invention have been illustrated in the accompanying drawings and described in the foregoing Detailed Description, it will be understood that the invention is not limited to the embodiments disclosed but is capable of numerous rearrangements, modifications and substitutions without departing from the scope of the invention.

What is claimed is:

1. An apparatus for processing blood which has cells therein, comprising:
   at least one planar chamber having an input port for receiving said blood and an output port for evacuating said blood from said chamber, said chamber having opposing transparent walls,
   a first light source and a second light source both positioned on a first side of said chamber and oriented to direct light to said chamber, said first light source produces light having a first wavelength, said second light source produces light having a second wavelength which is different from said first wavelength,
   an image sensor having an array of pixels, said image sensor positioned on a second side of said chamber opposite said light sources,
   an electronic storage,
   a planar light control comprising an array of selectively operable light shutters, said light control positioned between said light sources and said at least one chamber, said light control positioned parallel to said chamber, and
   a processor coupled to said image sensor, to said electronic storage and to said light control.

2. The apparatus as recited in claim 1, wherein said light control includes an array of individually controlled LCD shutters which pass light selectively through said light control.

3. The apparatus as recited in claim 1, wherein said first and second light sources comprises an array of individual light generators.

4. The apparatus as recited in claim 3, wherein each of said light generators includes at least one light emitter and a light reflector.

5. The apparatus as recited in claim 1, including an input flow line coupled to said input port of said chamber, an output flow line coupled to said output of said chamber, said input flow line and said output flow line are coplanar.

6. The apparatus as recited in claim 1, wherein said chamber includes a plurality of parallel flow channels extending from proximate a first edge of said chamber at said input port thereof to proximate a second edge of said chamber at said output port thereof.

7. The apparatus as recited in claim 1, wherein interior surfaces of said chamber opposing transparent walls are spaced apart by a plurality of parallel ridges which form flow channels between said input and output ports of said chamber.

8. An apparatus for processing blood which has cells therein, comprising:
   a cassette having therein a plurality of planar chambers each having an input port for receiving said blood and an output port for evacuating said blood from said chamber, each said chamber having opposing transparent walls,
   said cassette having an input port and an output port,
   a distribution manifold within said cassette, said distribution manifold having an input connected to said cassette input port and a plurality of outputs connected respectively to the input ports of said plurality of chambers,
   a collection manifold within said cassette, said collection manifold having a plurality of inputs connected respectively to the output ports of said plurality of chambers and said collection manifold having an output connected to the output port of said cassette,
   said distribution manifold and said collection manifold are coplanar with said plurality of planar chambers,
   a light source external to said cassette,
   a plurality of image sensors corresponding respectively to said plurality of said chambers, each said image sensor having an array of pixels, each of said image sensors positioned in parallel with and aligned with a respective one of said chambers, said image sensors external to said cassette,
   an electronic storage,
   at least one processor coupled to said image sensors and said electronic storage, and
   a planar light control having a plurality of selectively operable shutters for passing light selectively therethrough to said chambers, said light control coupled to said at least one processor and positioned between said light source and said chambers.

9. The apparatus as recited in claim 8, wherein said light source includes a first light generator that produces a first wavelength of light and a second light generator which produces a second wavelength of light which is different from said first wavelength.

10. The apparatus as recited in claim 8, wherein said input port and said output port of each said chamber are substantially equal in length to the width of the corresponding chamber.

11. The apparatus as recited in claim 8, wherein said light source comprises an array of individual light generators.

12. The apparatus as recited in claim 8, wherein each of said chambers includes a plurality of parallel flow channels extending from a first edge proximate the input port of each said chamber to a second edge proximate the output port of each said chamber.

13. The apparatus as recited in claim 8, wherein each of said image sensors is rectangular and is aligned with a corresponding one of said chambers which is also rectangular.

14. The apparatus as recited in claim 8, wherein interior surfaces of said opposing walls of each of said chambers are spaced apart by a plurality of parallel ridges.

15. An apparatus for processing blood which has pathogen cells therein, comprising:
- a planar cassette having therein a plurality of chambers each having an input port for receiving said blood and an output port for evacuating said blood from said chamber, each said chamber having parallel opposing transparent walls, said cassette having an input port and an output port,
- each of said chambers having a plurality of parallel ridges which space apart said opposing transparent walls,
- each of said chambers having a plurality of parallel flow channels between the input port and the output port thereof, said flow channels formed by said parallel ridges,
- a distribution manifold within said cassette, said distribution manifold having an input connected to said cassette input port and a plurality of outputs connected respectively to the input ports of said plurality of chambers,
- a collection manifold within said cassette, said collection manifold having a plurality of inputs connected respectively to the output ports of said plurality of chambers and said collection manifold having an output connected to said cassette output port,
- a light source external to said cassette,
- a plurality of image sensors each having an array of pixels, said image sensors positioned on the opposite side of said cassette from said light source, said image sensors corresponding respectively to said chambers in said cassette,
- an electronic storage, and
- a planar light control, said light control including an array of selectively operable light shutters, said light control positioned between said light source and said plurality of chambers.

16. The apparatus as recited in claim 15, wherein each of said shutters is an LCD shutter.

17. The apparatus as recited in claim 15, wherein said distribution manifold and said collection manifold are coplanar.

18. The apparatus as recited in claim 15, wherein the width of the input port of each said chamber is substantially equal in length to the width of the corresponding chamber.

19. The apparatus as recited in claim 15, wherein each of said input port said light source comprises an array of individual light generators.

20. The apparatus as recited in claim 15, including an operational unit for mounting therein said cassette, said light source, said image sensors, said light control and one or more processors electrically coupled to said light source, said image sensors and said light control.

* * * * *